US007141410B2

(12) United States Patent
Rajgarhia et al.

(10) Patent No.: US 7,141,410 B2
(45) Date of Patent: Nov. 28, 2006

(54) **METHODS AND MATERIALS FOR THE PRODUCTION OF ORGANIC PRODUCTS IN CELLS OF *CANDIDA* SPECIES**

(75) Inventors: Vineet Rajgarhia, Hopkins, MN (US); Merja Penttilä, Helsinki (FI); Laura Ruohonen, Helsinki (FI); Marja Ilmén, Helsinki (FI); Kari Koivuranta, Helsinki (FI); Pirkko Suominen, Maple Grove, MN (US)

(73) Assignee: Natureworks LLC, Minneapolis, MN (US)

( * ) Notice: Subject to any disclaimer, the term of this patent is extended or adjusted under 35 U.S.C. 154(b) by 307 days.

(21) Appl. No.: 10/154,460

(22) Filed: May 23, 2002

(65) Prior Publication Data

US 2003/0190630 A1    Oct. 9, 2003

Related U.S. Application Data

(63) Continuation-in-part of application No. 09/992,430, filed on Nov. 23, 2001.

(60) Provisional application No. 60/252,541, filed on Nov. 22, 2000.

(51) Int. Cl.
*C12P 21/04* (2006.01)
*C12N 5/00* (2006.01)
*C12N 9/04* (2006.01)
*C12N 15/74* (2006.01)
*C07H 21/02* (2006.01)
*C07H 21/04* (2006.01)

(52) U.S. Cl. .................. 435/254.22; 435/71.1; 435/320.1; 435/190; 435/471; 536/23.1; 536/24.1

(58) Field of Classification Search .............. 435/190, 435/254.22, 320.1, 440, 71.1, 6; 536/23.2
See application file for complete search history.

(56) References Cited

U.S. PATENT DOCUMENTS

| 4,275,234 | A |   | 6/1981 | Baniel et al. |
| 4,683,195 | A |   | 7/1987 | Mullis et al. |
| 4,859,596 | A |   | 8/1989 | Hollenberg et al. |
| 4,943,529 | A |   | 7/1990 | Van den Berg et al. |
| 5,510,526 | A |   | 4/1996 | Baniel et al. |
| 5,641,406 | A |   | 6/1997 | Sarhaddar et al. |
| 5,831,122 | A |   | 11/1998 | Eyal |
| 5,849,524 | A | * | 12/1998 | Kondo et al. ............. 435/69.1 |
| 6,485,947 | B1 | * | 11/2002 | Rajgarhia et al. ........... 435/139 |

FOREIGN PATENT DOCUMENTS

| WO | WO 93/00440 A1 |   | 7/1993 |
| WO | WO99/14335 | * | 3/1999 |

OTHER PUBLICATIONS

Skory, Isolation and Expression of Lactate Dehydrogenase Genes from *Rhizopus oryzae*, Applied and Environmental Microbiology, Jun. 2000, vol. 66 (6) 2343-2348.*
Savijoki and Palva, Molecular Genetic Characterization of the I-Lactate Dehydrogenase Gene (IdhL) of *Lactobacillus helveticus* and Biochemical Characterization of the Enzyme, Applied and Environmental Microbiology, Jul. 1997, vol. 63(7) pp. 2850-2856.*
Verduyn et al, Effects of Benzoic Acid on Metabolic Fluxes in Yeasts: A Continuous-Culture Study on the Regulation of Respiration and Aloholic Fermentation, Yeast, 1992, vol. 8, pp. 501-517.*
Backer et al. "Transformation of *Candida albicans* by Electroporation", 1999, *Yeast 15*: 1609-1618.
Becker and Guarente, "High-Efficiency Transformation of Yeast by Electroporation" *Methods in Enzymology* 194:182-187 (1991).
Chen et al., "Sequence Organization of the Circular Plasmid pKD1 from the yeast *Kluyveromyces drosophilarum*", 1986, *Nucleic Acids Res. 14*: 4471-4481.
Chien et al. "The two-hybrid system: A method to identify and clone genes for proteins that interact with a protein of interest", (*Proc. Natl Acad. Sci.*, 88:9578-9582 (1991).
Danner et al. Applied Biochemistry and Biotechnology vol. 70-72 (1998).
Datta et al., "Technological and economic potential of poly (lactic acid) and lactic acid derivatives", 1995, *FEMS Microbiol. Rev.* 16: 221-231.
Durrens et al., "Expression of the avian gag-myc oncogene in *Saccharomyces cerevisiae*", *Curr Genet*. 18:7-12 (1990).
Franzblau & Sinclair, "Induction of fermentation in Crabtree-Negative Yeasts", 1983, *Mycopathologia* 82: 185-190.
Gellissen and Hollenberg,"Application of yeast in gene expression studies: a comparison of *Saccharomyces cerevisiae*, *Hansenula polymoroha* and *Kluyveromyces lactis*- a review", Gene, 19-:87-97.
Gietz et al., "Improved Method for High Efficiency Transformation of Intact Yeast Cells". 1992, *Nucleic Acids Res.* 20:1425.
Gune and Kitada, *J. Epidemiol.*,4:409-414 (1988).
Gunge et al., "Isolation and Characterization of Linear Deoxyribonucleic Acid Plasmids from *Kluyveromyces lactis* and the Plasmid-Associated Killer Character", *J. Bacteriol.* I45:382-390 1981.
Holdsworth et al. "Enzyme Activities in Oleoginous Yeasts Accumulating and Utilizing Exogenous or Endogenous Lipids", *J. Gen. Microbiol.*, 134:2907-2915(1998).
Hwang et al., "Characterization of the transcription activation function and the DNA binding domain of transcriptional enhancer factor-1" 1993, *EMBO J.* 12:2337-2348.

(Continued)

Primary Examiner—Dave Trong Nguyen
Assistant Examiner—Maria Marvich
(74) Attorney, Agent, or Firm—McDonnell Boehnen Hulbert & Berghoff

(57) ABSTRACT

The present invention relates to biocatalysts that are cells, optimally of the Crabtree-negative phenotype, comprising expression vectors encoding genes heterologous to the cell that enable increased production of organic products. More specifically, the invention relates to genetically modified *Candida* cells, methods for making the *Candida* cells, and their use in production of organic products, particularly lactic acid.

8 Claims, 33 Drawing Sheets

OTHER PUBLICATIONS

Ito et al., *J. Bacterol.* 153:163-168 (1983).

Kelly et al., "Affinity Chromatography of Bacterial Lactate Dehydrogenases" Biochem J., 171:543-7.

Kiers et al., "Regulation of Alcoholic Fermentation in Batch and Chemostat Cultures of *Kluyveromyces lactis* CBS 2359" *Yeast*, 14, 459-469 (1998).

Kurtzman and Fell, (1998) "*The Yeasts, A Taxonomic Study*" pp. 240-241.

Mach et al. "Transformation of *Trichoderma reesei* based on Hygromycin B resistance using homologous expression signals", 1994, *Curr. Genet.* 25, 567-570.

Bunch et al., "IdhA gene encoding the fermentative lactate Dehydrogenase of *Escherichia coli*", *Microbiology*, 143:187-95.

Morsomme et al. "Single point mutation in various domains of a plant plasma membrane H+-ATPase Expressed in *Saccharomyces cerevisie* H+-pumping and permit growth at low pH", (*EMBO J.* 15:5513-5526 1996.

Naumov et al., 1990, *MGG 224*:119-128.

Postma et al., "Enzymic Analysis of the Crabtree Effect in Glucose-Limited Chemostaat Cultures of *Saccharomyces cerevisiae*", *Appl Environ. Microbiol.* 53, 468-477 (1989).

Sambrook et al., 1989, Molecular Cloning, 2$^{nd}$ Ed., Cold Spring Harbor Laboratory, NY.

Subden et al. "An L-lactic acid dehydrogenase based method for detecting microbial colonies performing a malo-lactic fermentation", (*Canadian J. Microbiol.*, 28:883-886 (1982).

Thomas et al., "Biocatalysis:applications and potentials for the chemistry industry", 2002, *Trends Biotechnol. 20*:238-42.

Turakainen et al., "Consideration of the Evolution of the *Saccharomyces cerevisiae* MEL Gene Family of the Basis of the Nucleotide Sequences of the Genes and Their Flanking Regions", 1994, *Yeast 10*: 1559-1568.

Ullhrich, "Yeast Pyruvate Decarboxylase (2-Oxoacid Carboxylyase, EC 4.1.1.1) Assay of Thiamine Pyrophosphate" *Methods in Enzymology* 18:109-115 (1970).

Vickroy, "Lactic Acid", 1985, *Comprehensive Biotechnology*, (Moo-Young, ed.), vol. 3, Chapter 38 Pergamon Press, Oxford.

Wesolowski-Louvel et al. "*Kluyveromyces lactis*", (Nonconventional Yeasts in Biotechnology: *Kluyveromyces lactis*, ed. Klaus Wolf, Springer Verlag, Berlin, p. 138-201 (1996).

Witte et al. (*J. Basic Microbial.* 29:707-7 16 (1989).

\* cited by examiner

FIG. 1: G418 resistance vector pMI260.
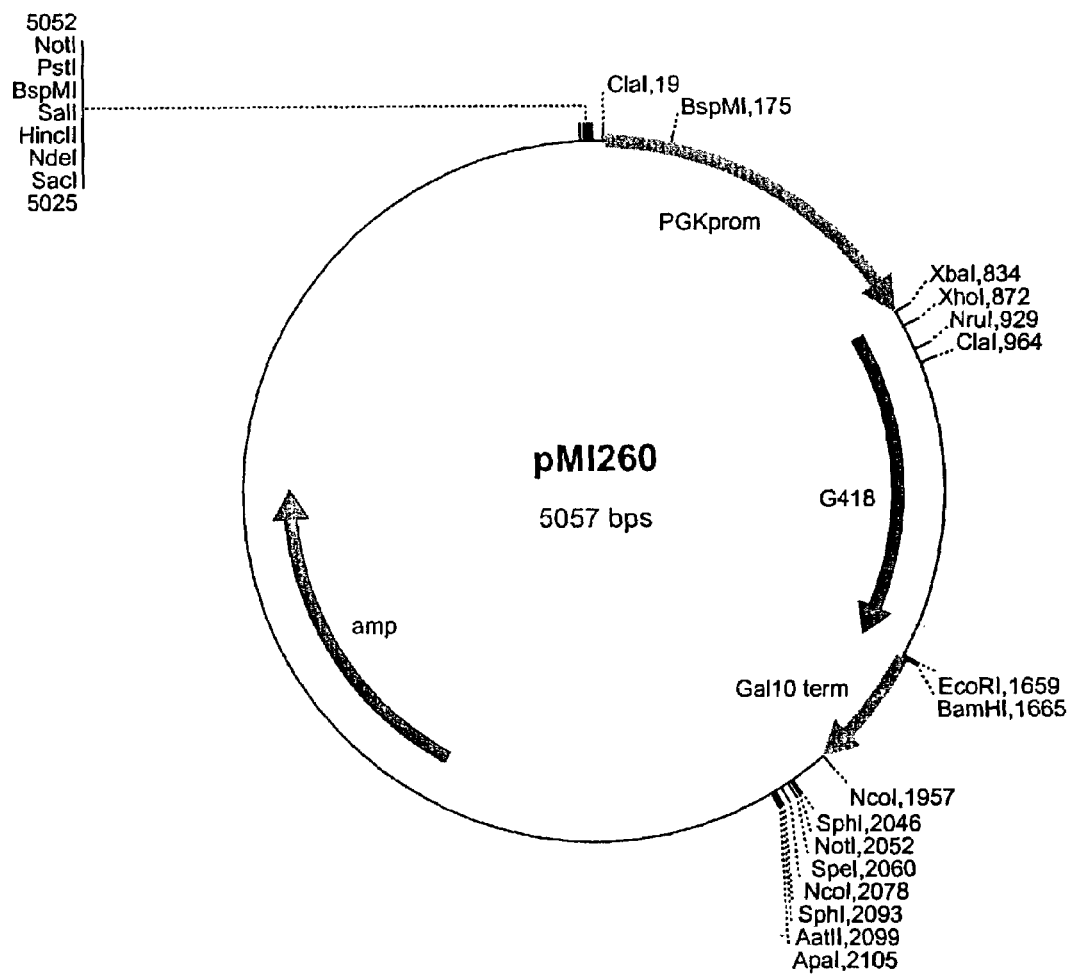

FIG. 2: G418 resistance vector pMI268.
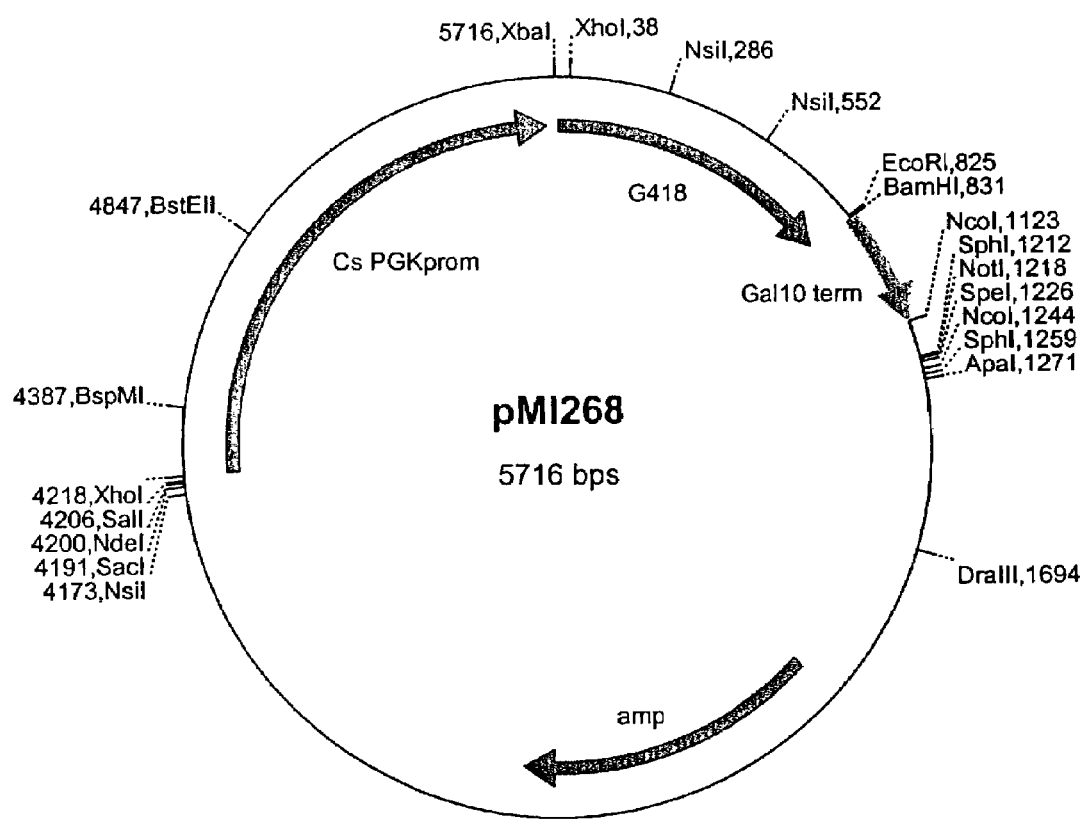

FIG. 3: G418 resistance vector pMI269.
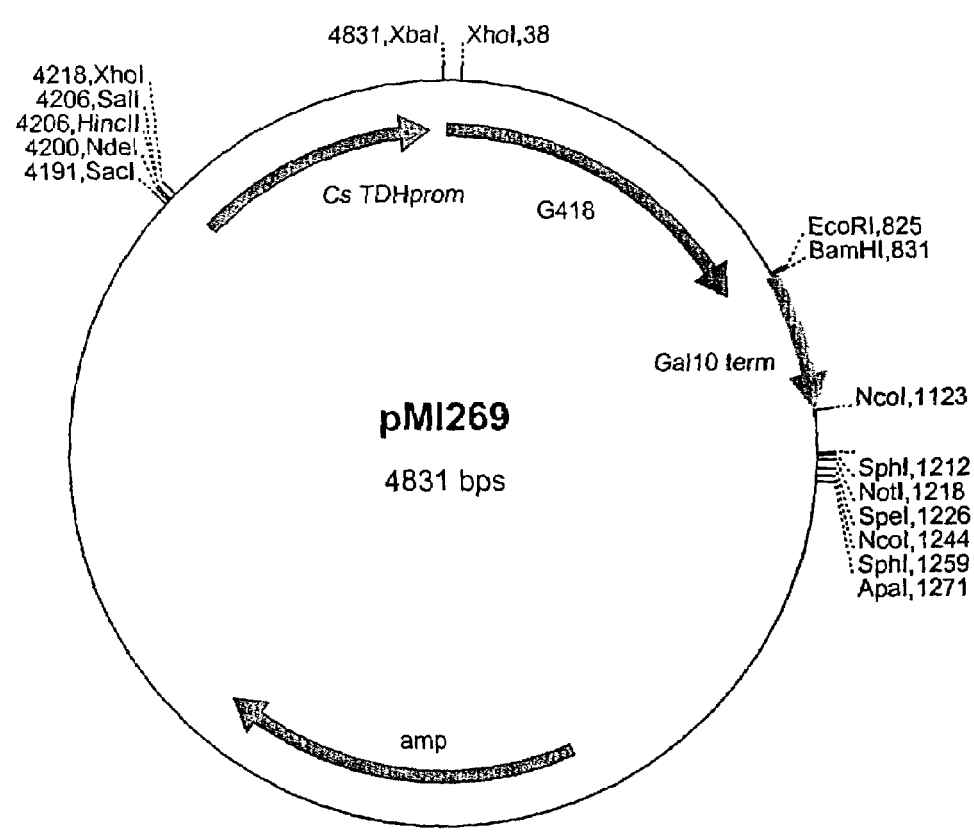

FIG. 4: Hygromycin resistance vector pMI270.
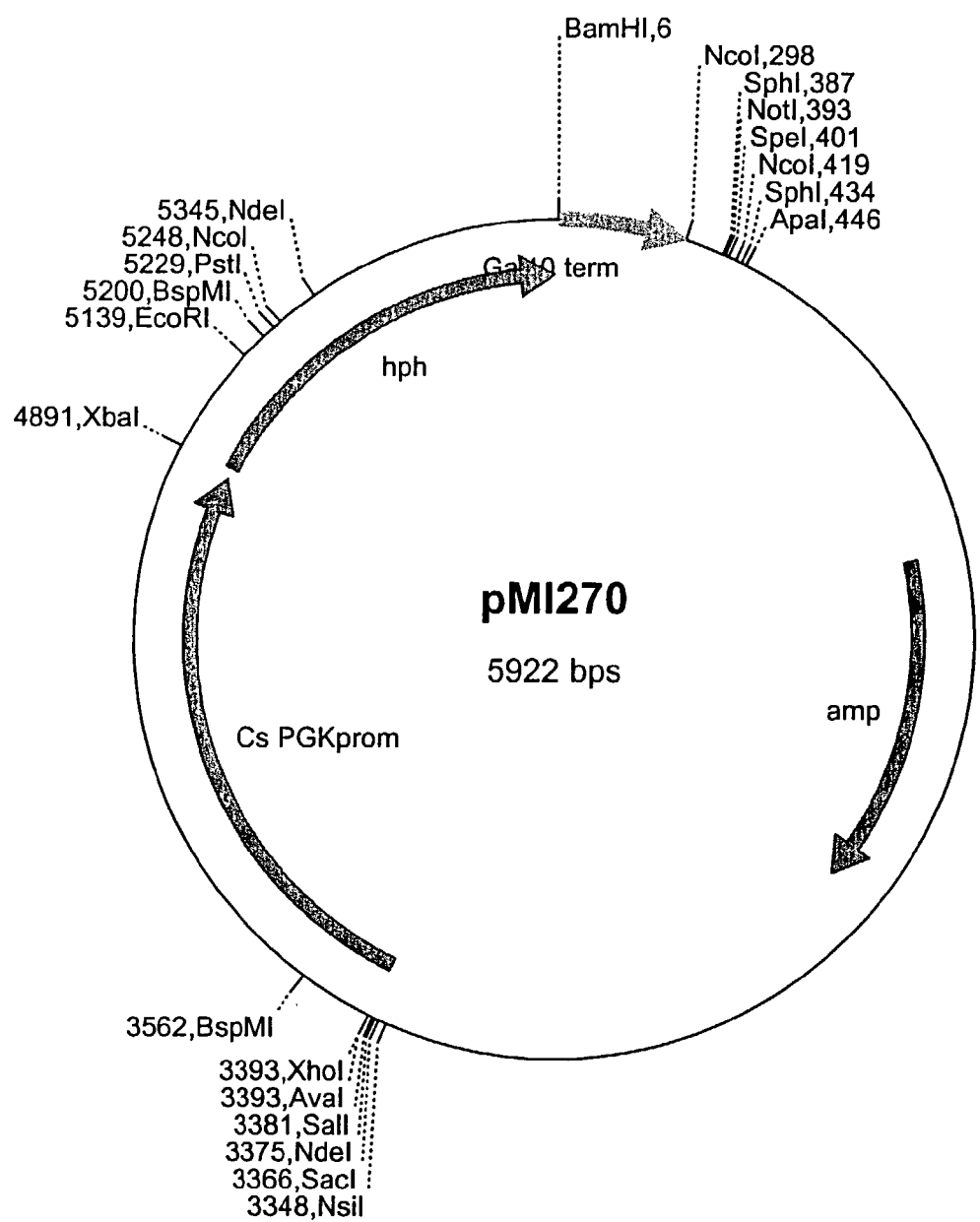

**FIG. 5: Vector pMI234 for expression of *MEL5*.**
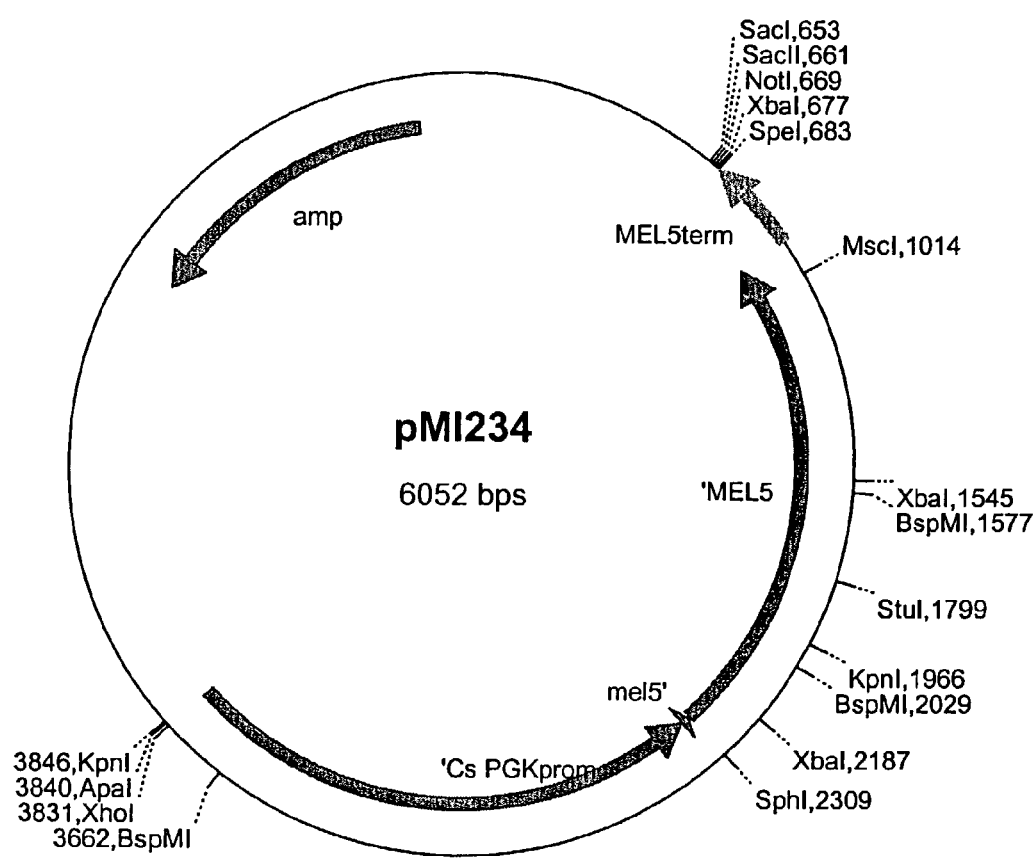

FIG. 6: Vector pMI238 for expression of *MEL5*.
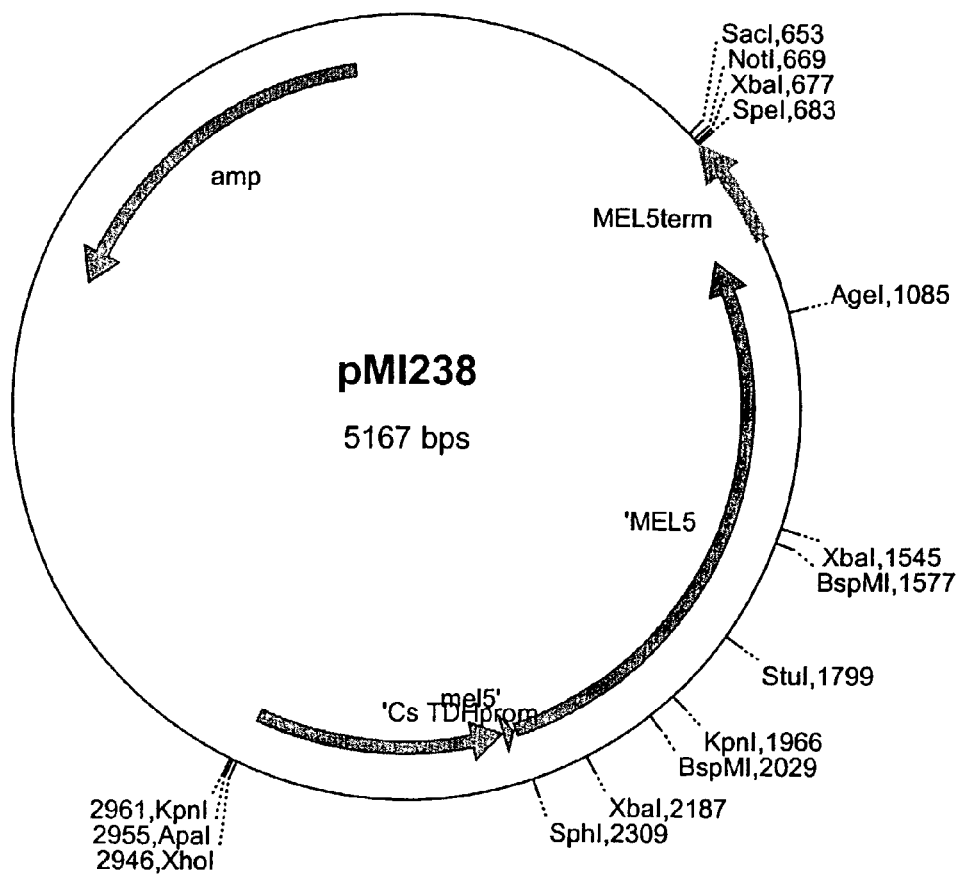

FIG. 7: Hygromycin resistance vector pMI271.
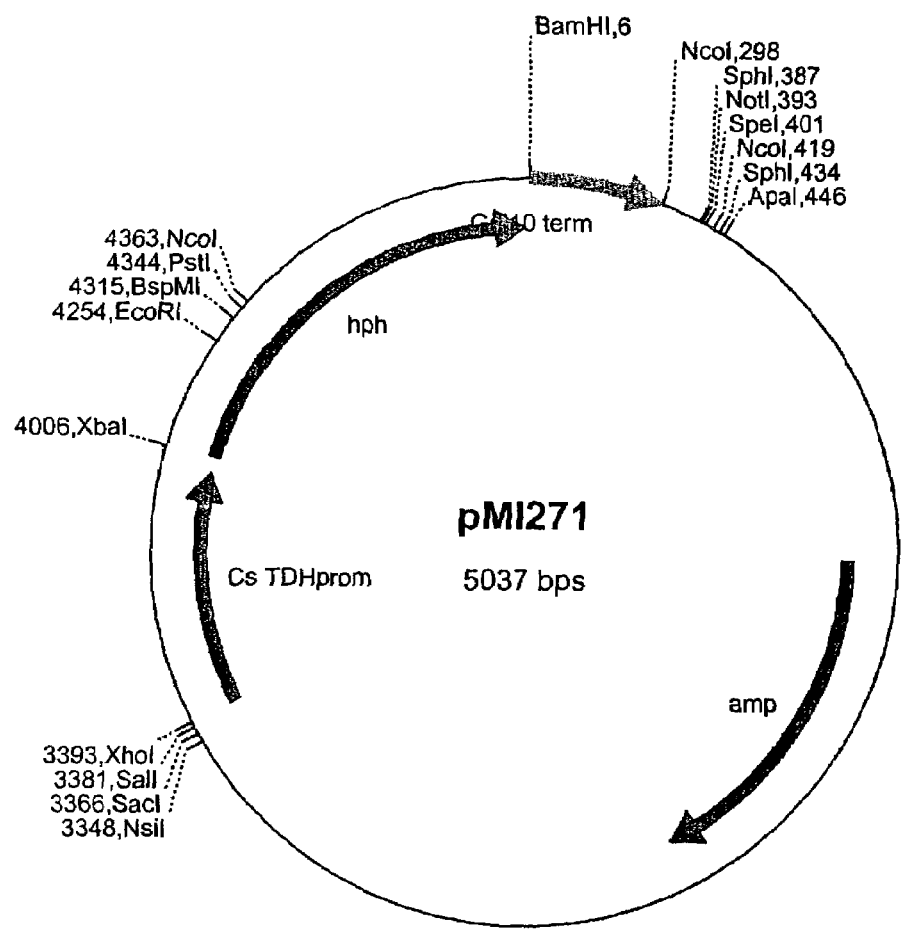

FIG. 8: Vector pMI246 for expression of *L. helveticus* LDH.
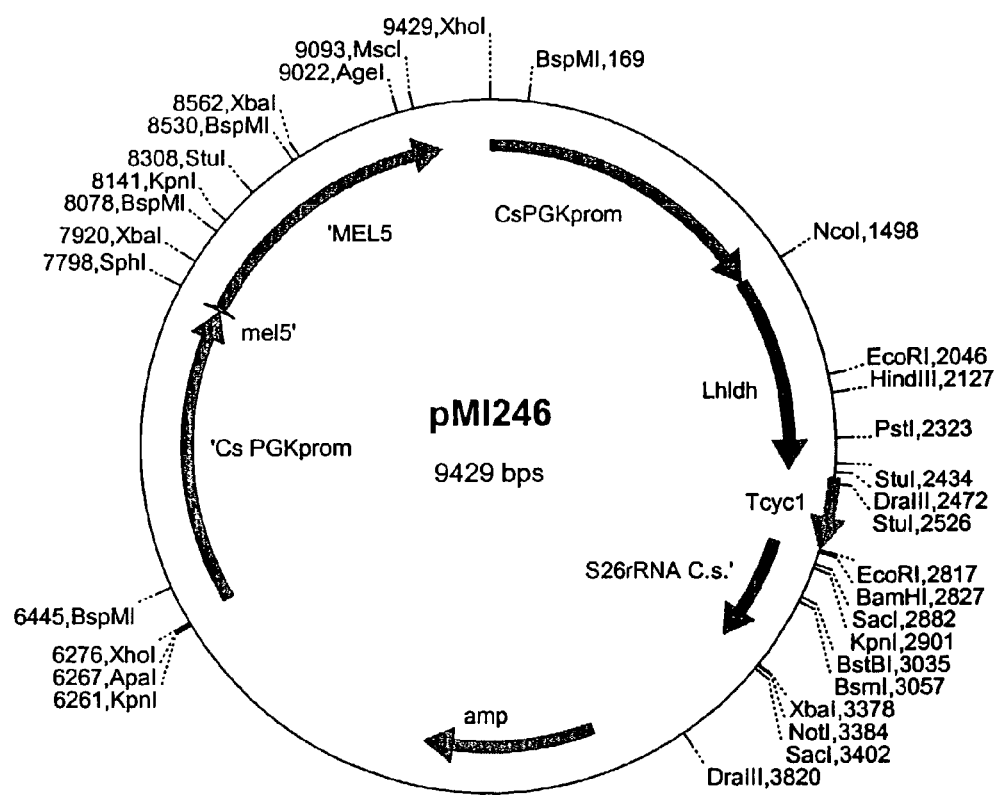

FIG. 9: Vector pMI247 for expression of *L. helveticus* LDH.
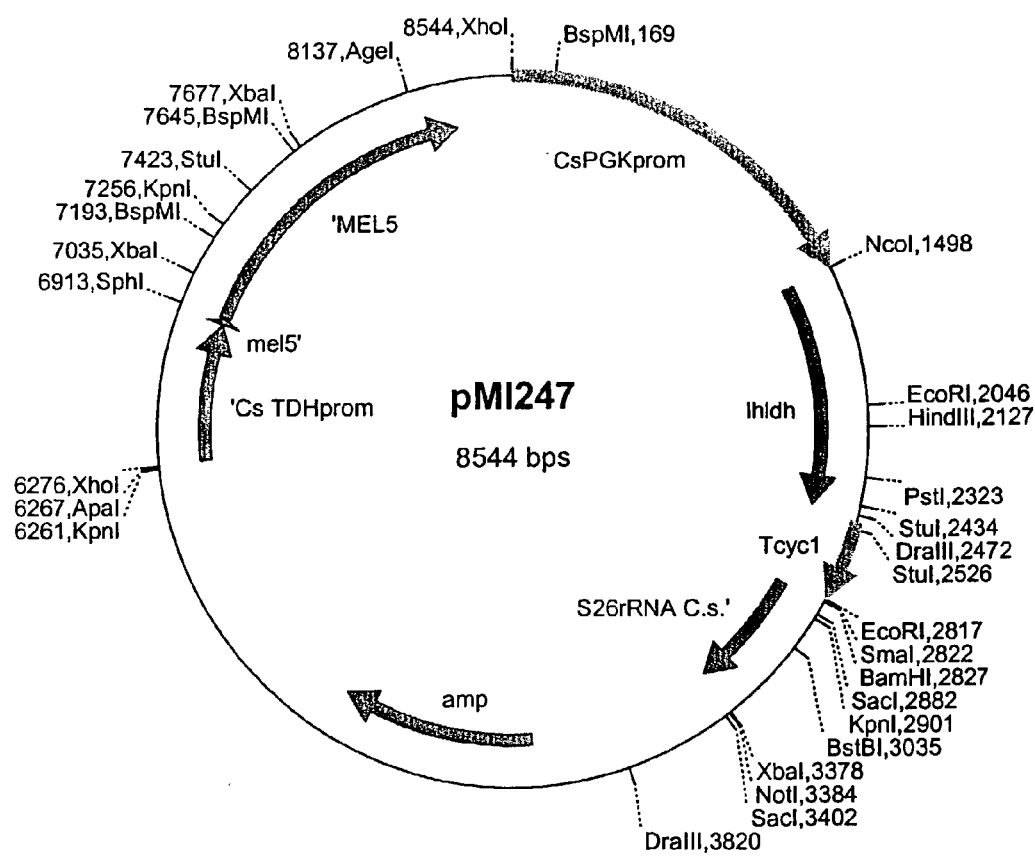

FIG. 10: Vector pMI257 for expression of *L. helveticus* LDH and for integration into the *PDC1* locus.
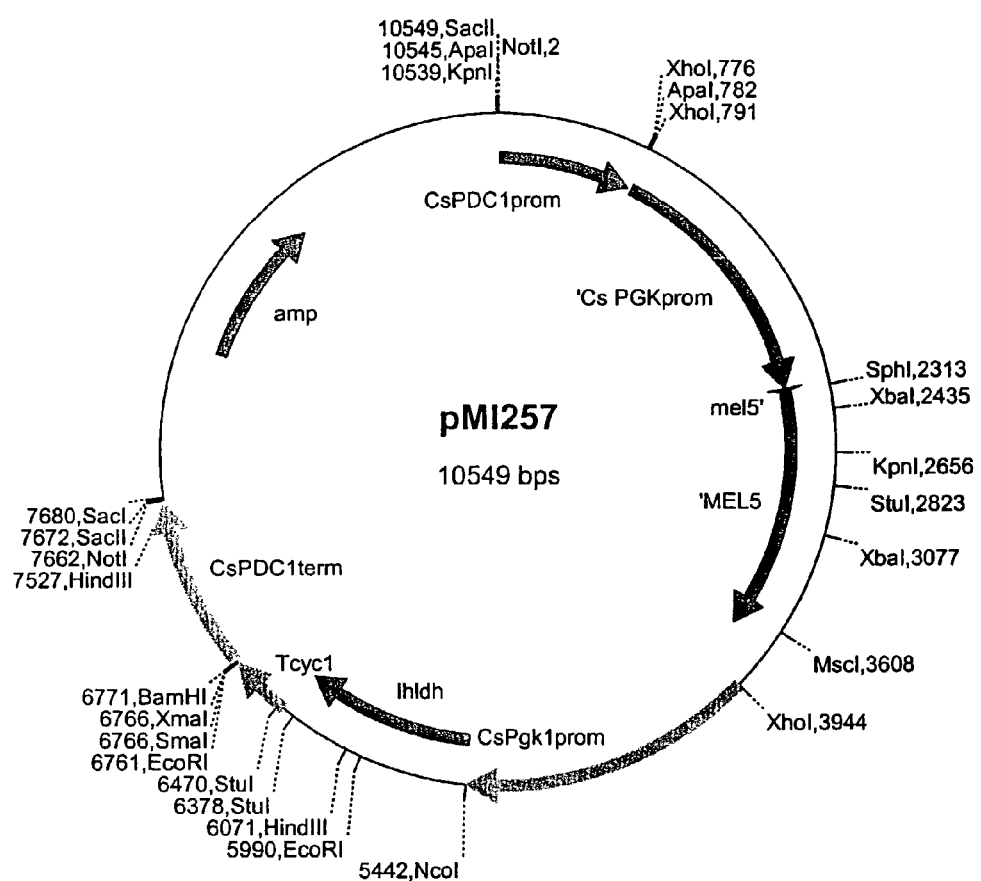

FIG. 11: Vector pMI265 for expression of *B. megaterium* LDH and for integration into the *PDC1* locus.
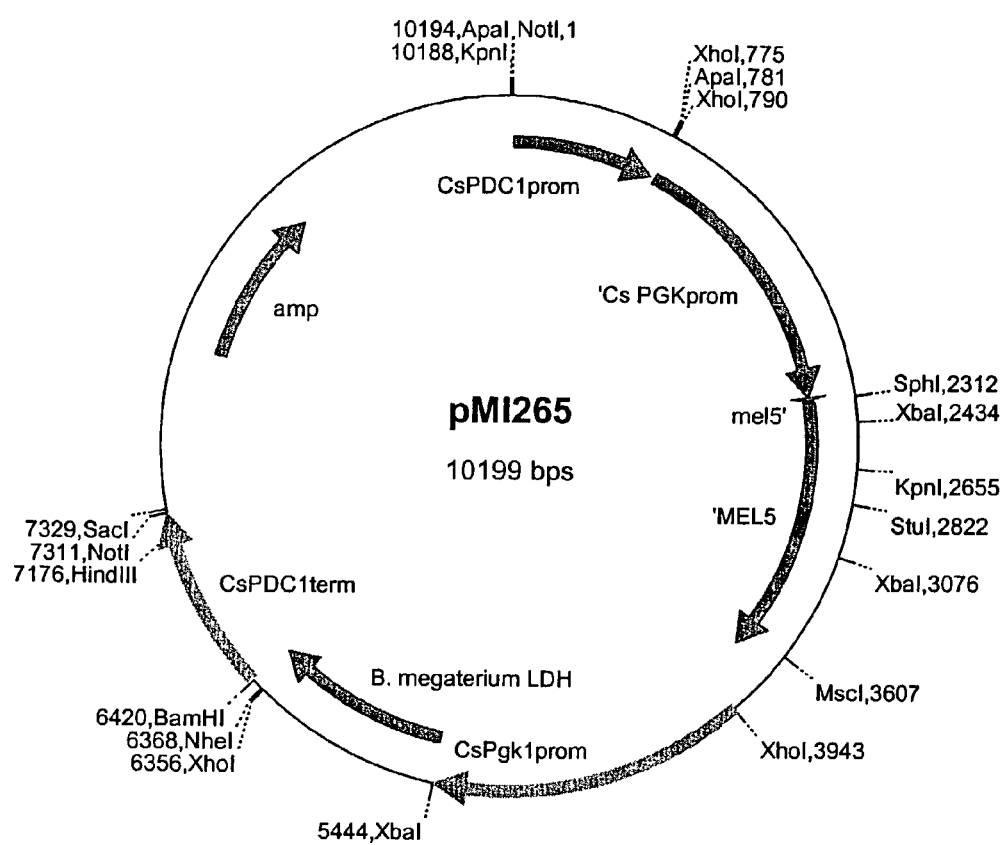

FIG. 12: Vector pMI266 for expression of *R. oryzae* LDH and for integration into the *PDC1* locus.
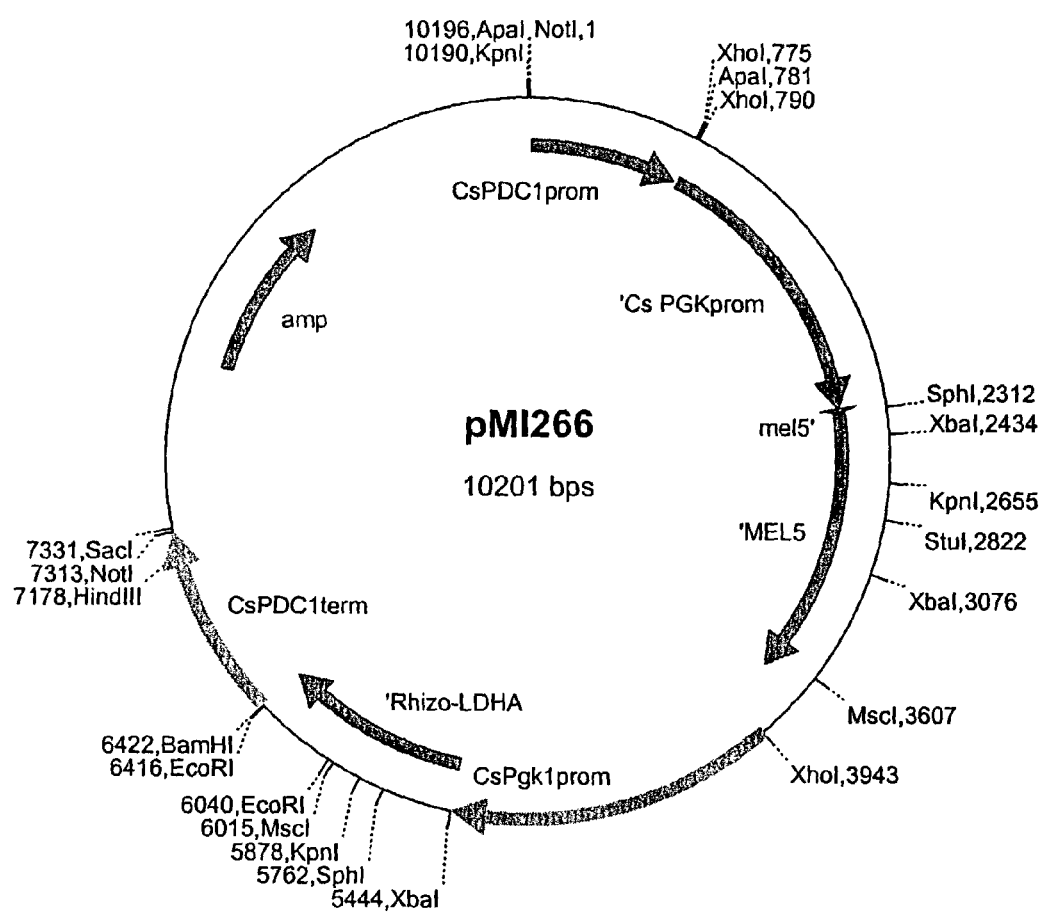

FIG. 13: Vector pMI267 for replacement of the *PDC1* locus.
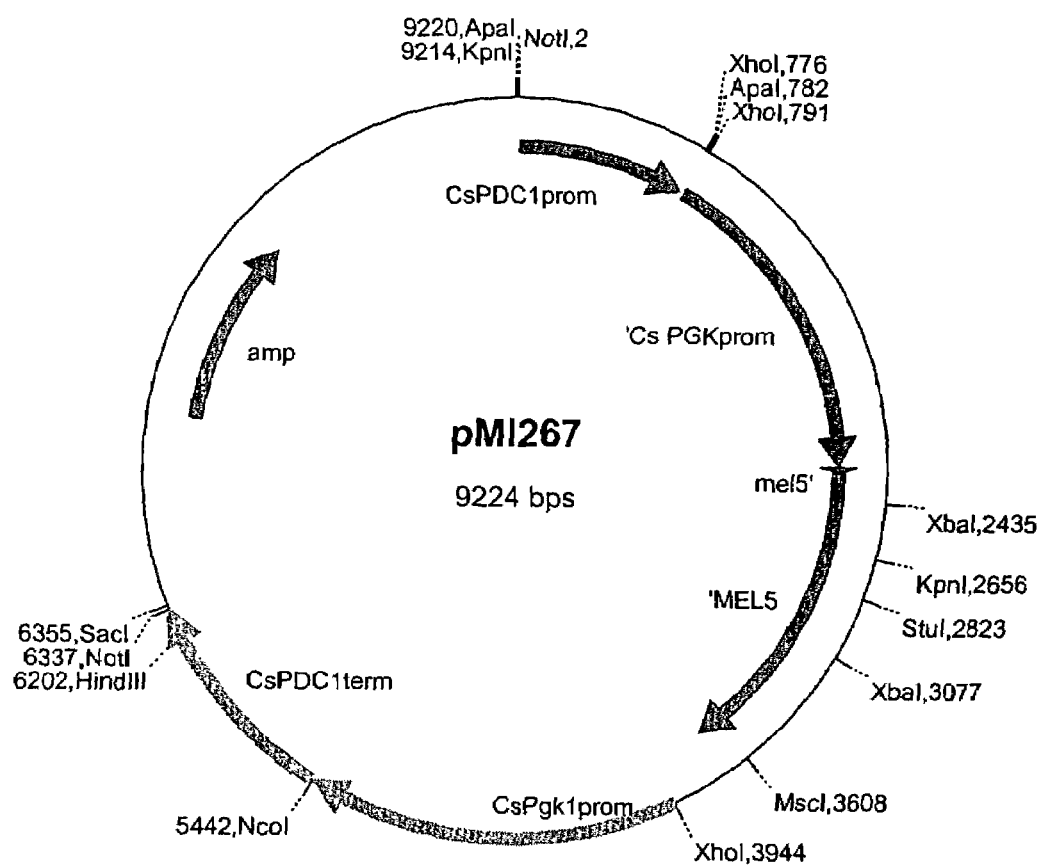

FIG. 14: Vector pMI278 for expression of *B. megaterium* LDH.
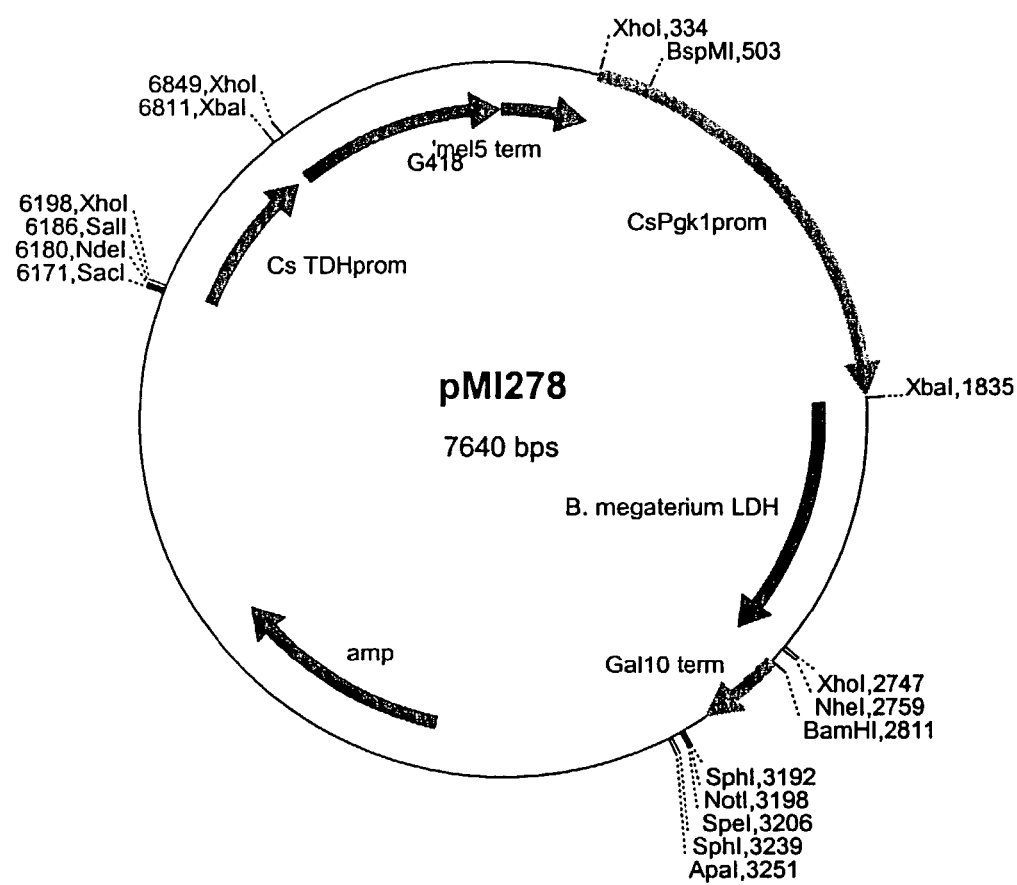

FIG. 15: Vector pMI286 for expression of *B. megaterium* LDH and for integration into the *PDC2* locus.
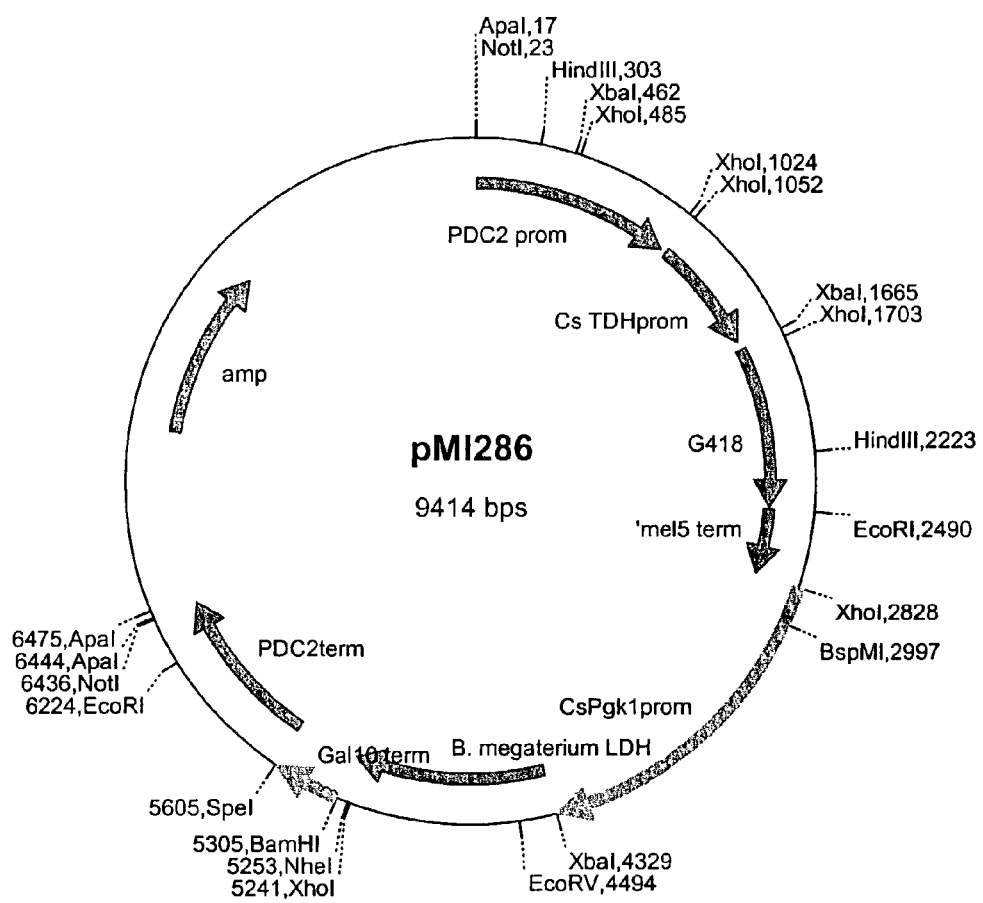

FIG. 16: Vector pMI287 for integration into the *PDC2* locus.
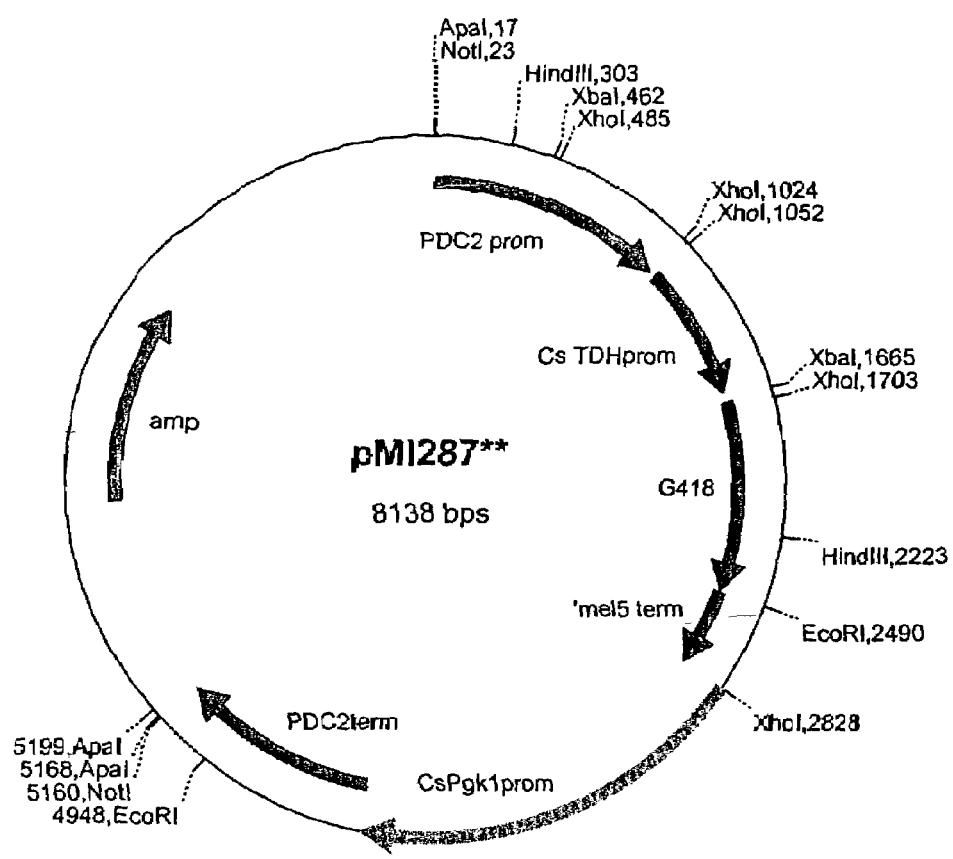

FIG. 17: Vector pMI288 for expression of *L. helveticus* LDH and for integration into the *PDC2* locus
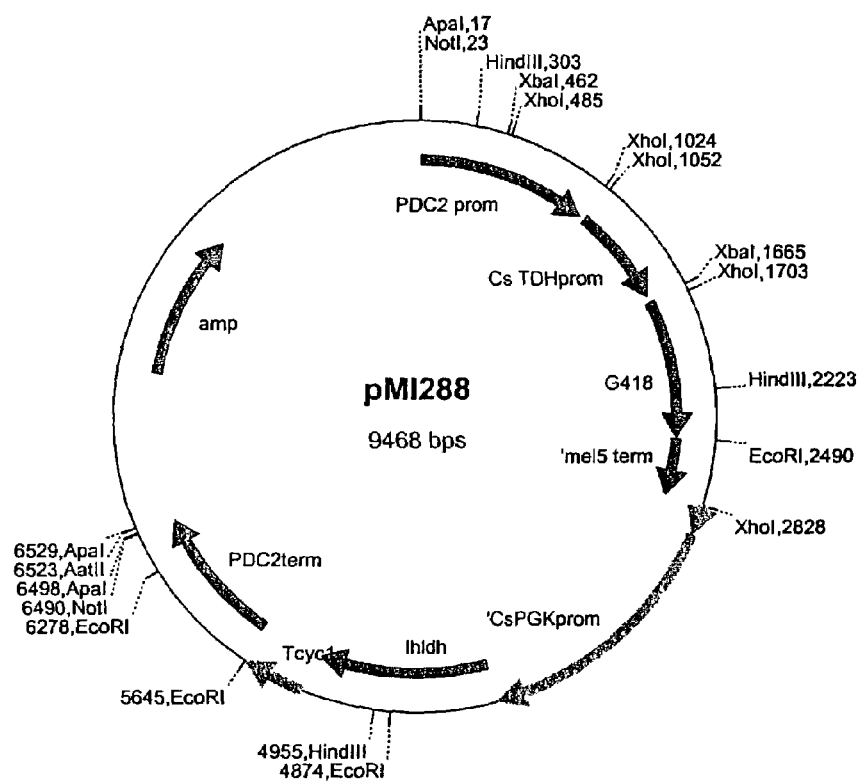

FIG. 18: Vector pMI256 for expression of *L. helveticus* LDH with *S. cerevisiae* MEL5 for integration into the *PDC1* locus
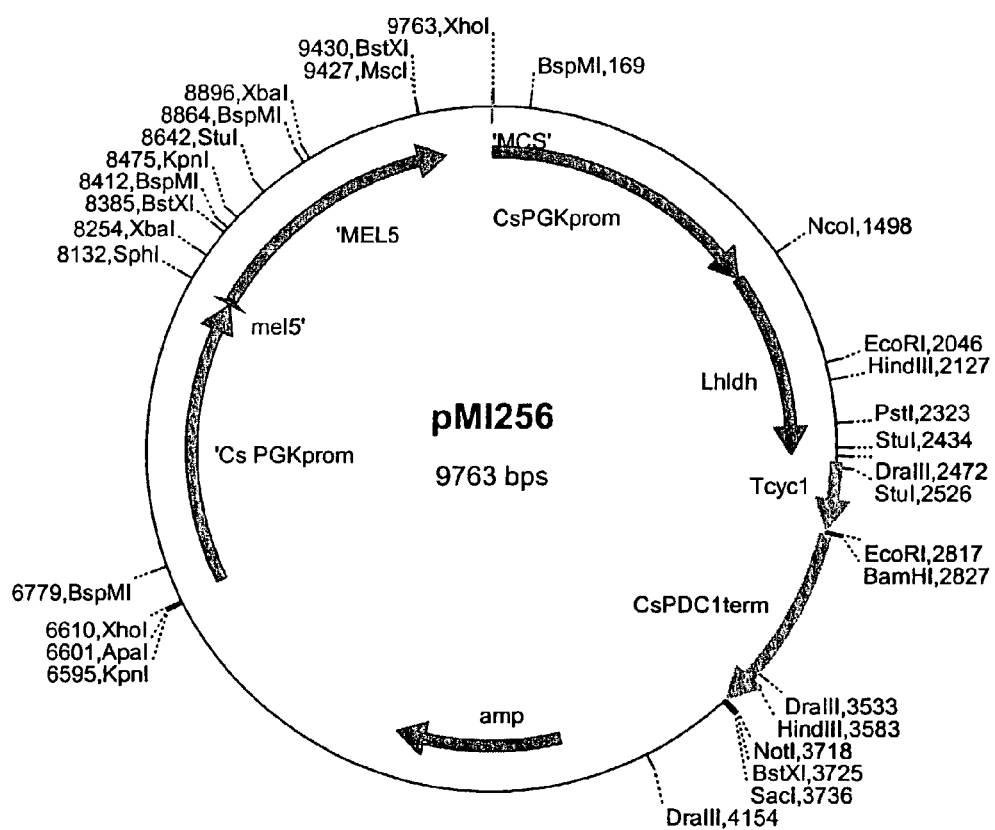

FIG. 19: Vector pMI277 containing the *PDC2* (*C. sonorensis*) promoter
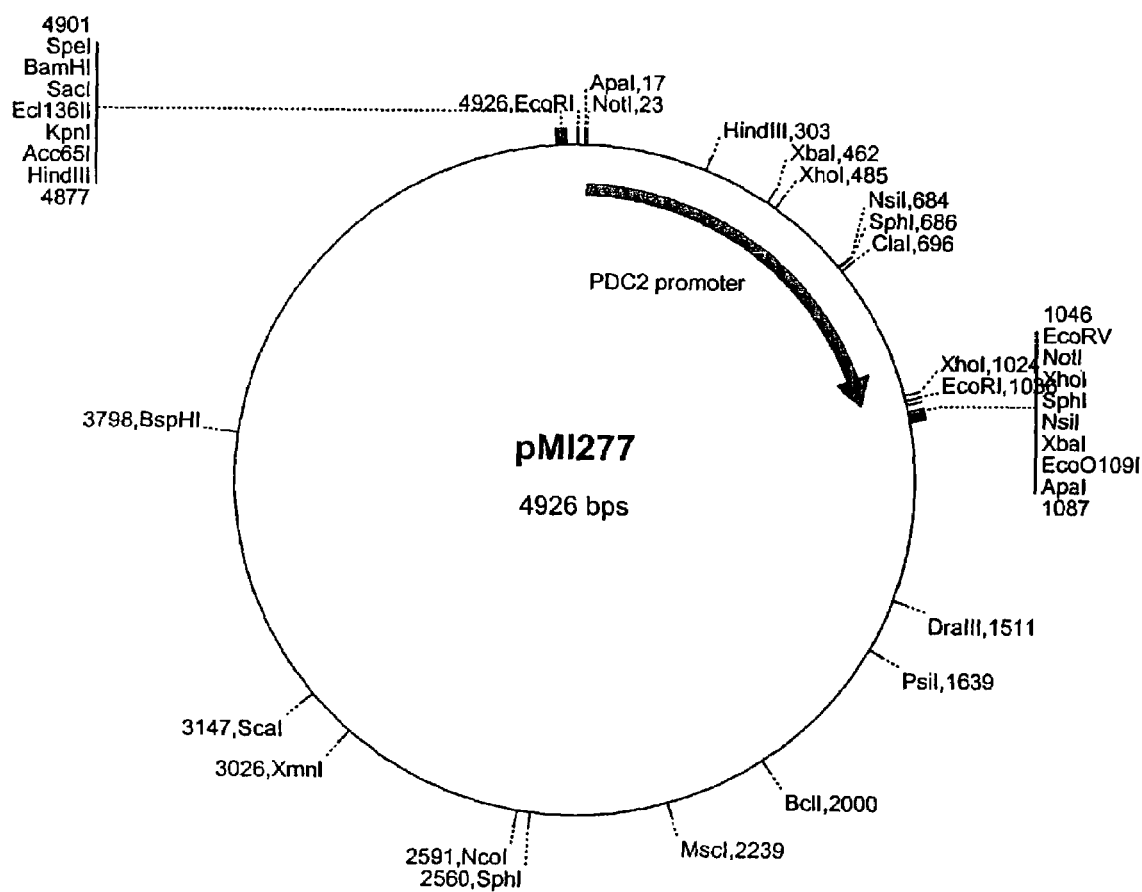

FIG. 20: Vector pMI279 for expression of LDH (*B. megaterium*) containing the G418 resistance-coding gene for integration at the *PDC2* locus
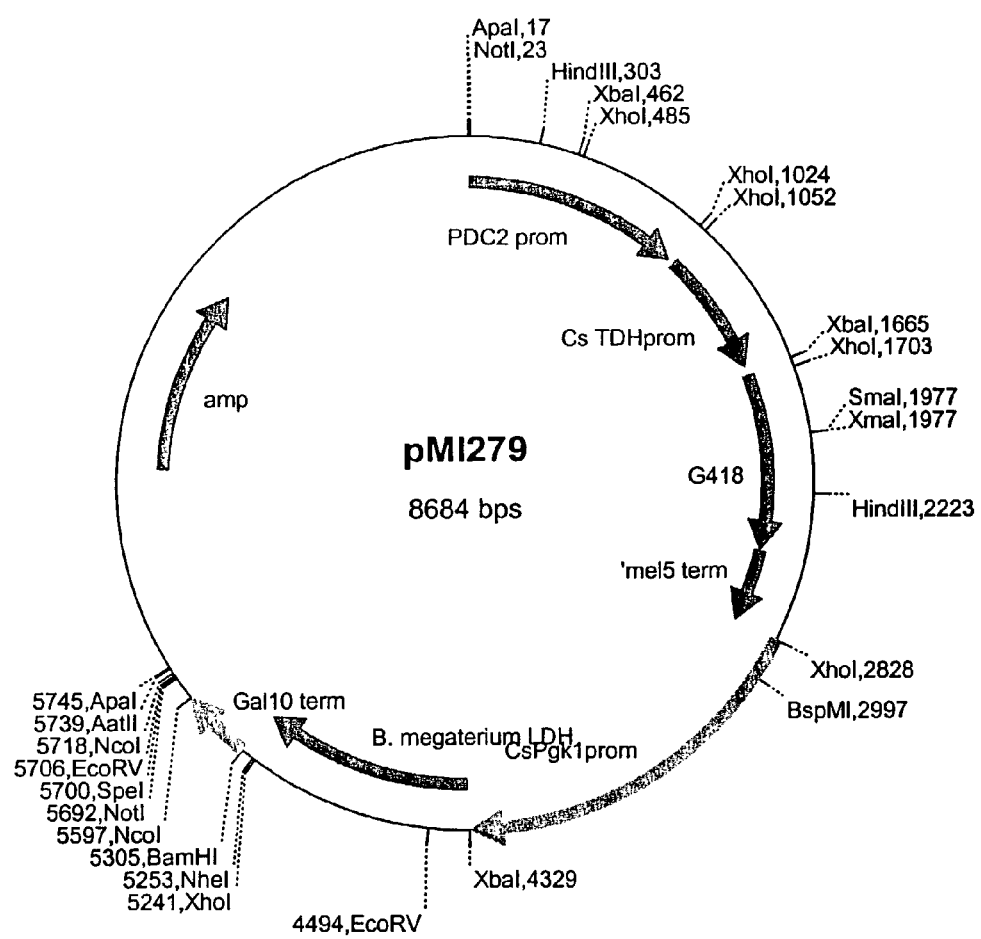

FIG. 21: Vector pVR24
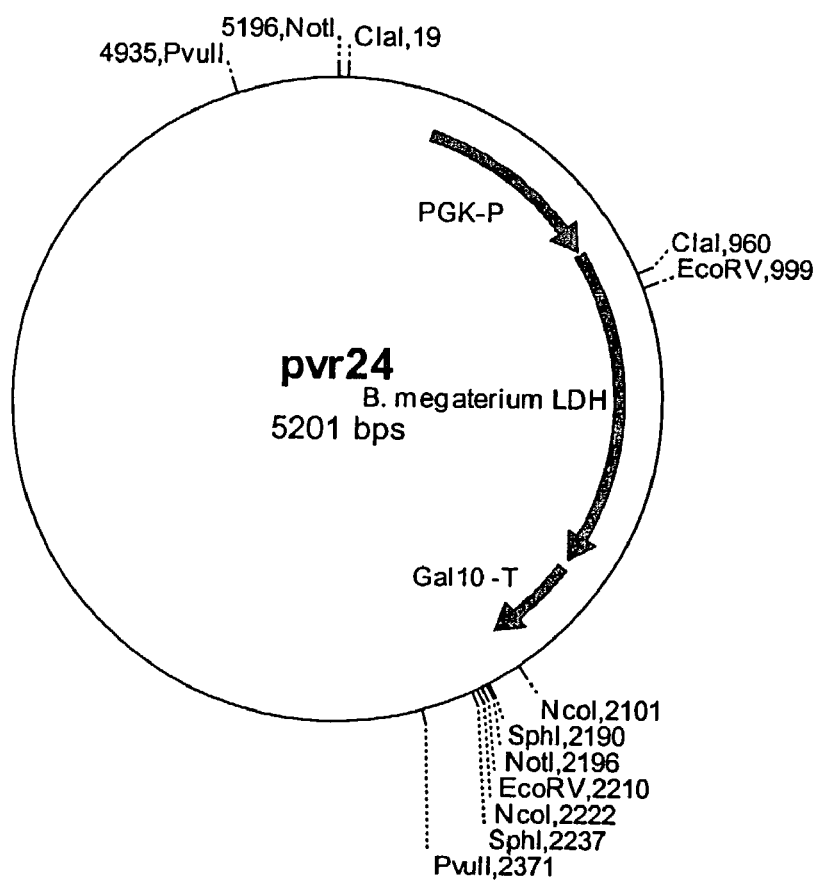

FIG. 22: Vector pVR27
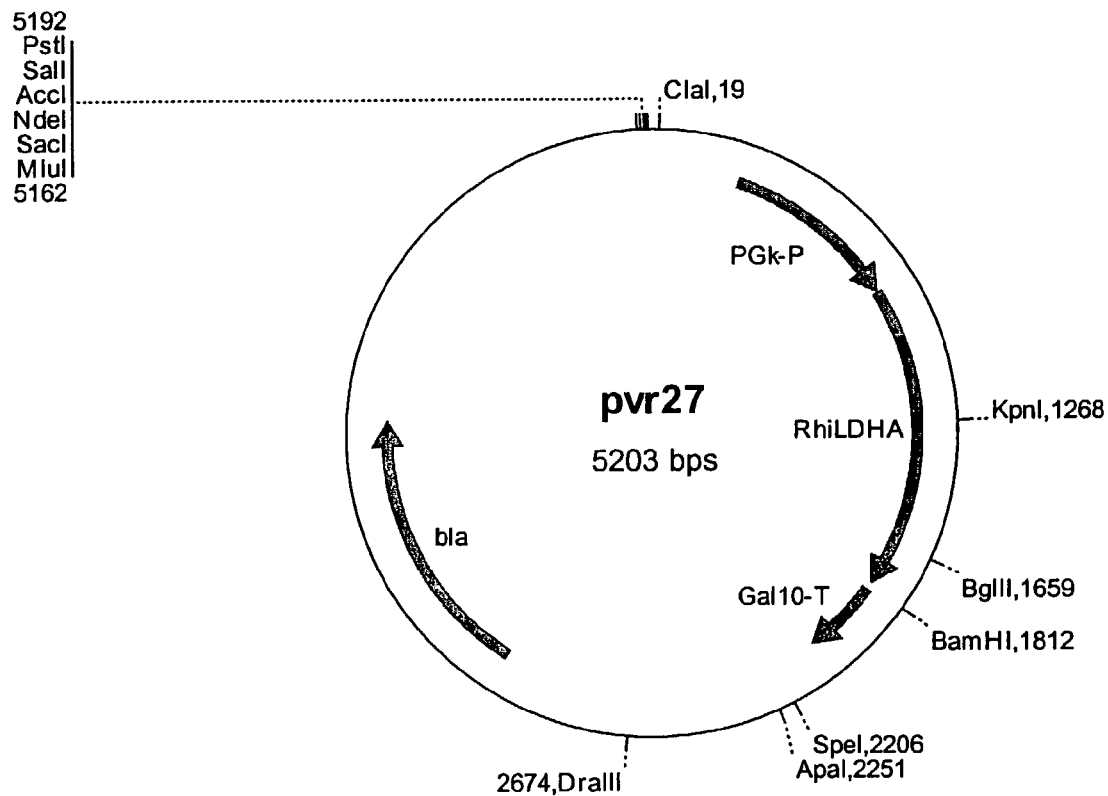

SEQUENCE LISTING

<160> NUMBER OF SEQ ID NOS: 50

<210> SEQ ID NO 1
<211> LENGTH: 37
<212> TYPE: DNA
<213> ORGANISM: Artificial Sequence
<220> FEATURE:
<223> OTHER INFORMATION: Primer for G418 resistance gene

<400> SEQUENCE: 1
ctagtctaga acaatgagcc atattcaacg ggaaacg            37

<210> SEQ ID NO 2

```
<211> LENGTH: 42
<212> TYPE: DNA
<213> ORGANISM: Artificial Sequence
<220> FEATURE:
<223> OTHER INFORMATION: Primer for G418 resistance gene (3')

<400> SEQUENCE: 2
cgcggatccg aattcttaga aaaactcatc gagcatcaaa tg                42

<210> SEQ ID NO 3
<211> LENGTH: 34
<212> TYPE: DNA
<213> ORGANISM: Artificial Sequence
<220> FEATURE:
<223> OTHER INFORMATION: Primer for TDH1 promoter (C. sonorensis)

<400> SEQUENCE: 3
gcgatctcga gaaaatgtta ttataacact acac                        34

<210> SEQ ID NO 4
<211> LENGTH: 42
<212> TYPE: DNA
<213> ORGANISM: Artificial Sequence
<220> FEATURE:
<223> OTHER INFORMATION: Primer for TDH1 promoter (C. sonorensis)

<400> SEQUENCE: 4
ctagtctaga tttgtttgat ttgtttgttt tgttttttgtt tg              42

<210> SEQ ID NO 5
<211> LENGTH: 36
<212> TYPE: DNA
<213> ORGANISM: Artificial Sequence
<220> FEATURE:
<223> OTHER INFORMATION: Primer for PGK1 promoter (C. sonorensis)

<400> SEQUENCE: 5
gcgatctcga gaaagaaacg acccatccaa gtgatg                      36

<210> SEQ ID NO 6
<211> LENGTH: 35
<212> TYPE: DNA
<213> ORGANISM: Artificial Sequence
<220> FEATURE:
<223> OTHER INFORMATION: Promoter for PGK1 promoter (C. sonorensis)

<400> SEQUENCE: 6
ctagtctaga tgtatatagt cttttctatt attag                       35

<210> SEQ ID NO 7
<211> LENGTH: 38
<212> TYPE: DNA
<213> ORGANISM: Artificial Sequence
<220> FEATURE:
<223> OTHER INFORMATION: Hygromycin gene resistance primer (E. coli)

<400> SEQUENCE: 7
ccggactagt tggtacagag aacttgtaaa caattcgg                    38

<210> SEQ ID NO 8
<211> LENGTH: 23
<212> TYPE: DNA
<213> ORGANISM: Artificial Sequence
<220> FEATURE:
<223> OTHER INFORMATION: Hygromycin gene resistance primer (E. coli)

<400> SEQUENCE: 8
```
tataaatact tatcatttcc tcc                                          23

<210> SEQ ID NO 9
<211> LENGTH: 50
<212> TYPE: DNA
<213> ORGANISM: Artificial Sequence
<220> FEATURE:
<223> OTHER INFORMATION: Primer for PDC1 terminator (C. sonorensis)

<400> SEQUENCE: 9
gggactagtg gatccttgaa gtgagtcagc cataaggact taaattcacc              50

<210> SEQ ID NO 10
<211> LENGTH: 52
<212> TYPE: DNA
<213> ORGANISM: Artificial Sequence
<220> FEATURE:
<223> OTHER INFORMATION: Primer for PDC1 terminator (C. sonorensis)

<400> SEQUENCE: 10
aaggccttgt cgacgcggcc gcttggttag aaaaggttgt gccaatttag cc           52

<210> SEQ ID NO 11
<211> LENGTH: 42
<212> TYPE: DNA
<213> ORGANISM: Artificial Sequence
<220> FEATURE:
<223> OTHER INFORMATION: Primer for PDC1 promoter (C. sonorensis)

<400> SEQUENCE: 11
gggacgggcc cgcggccgct acaagtgatt cattcattca ct                     42

<210> SEQ ID NO 12
<211> LENGTH: 45
<212> TYPE: DNA
<213> ORGANISM: Artificial Sequence
<220> FEATURE:
<223> OTHER INFORMATION: Primer for PDC1 promoter (C. sonorensis)

<400> SEQUENCE: 12
ccctgggccc ctcgaggatg atttagcaag aataaattaa aatgg                  45

<210> SEQ ID NO 13
<211> LENGTH: 43
<212> TYPE: DNA
<213> ORGANISM: Artificial Sequence
<220> FEATURE:
<223> OTHER INFORMATION: Primer for PDC2 promoter (C. sonorensis)

<400> SEQUENCE: 13
gggacgggcc cgcggccgct tacagcagca aacaagtgat gcc                    43

<210> SEQ ID NO 14
<211> LENGTH: 43
<212> TYPE: DNA
<213> ORGANISM: Artificial Sequence
<220> FEATURE:
<223> OTHER INFORMATION: Primer for PDC2 promoter (C. sonorensis)

<400> SEQUENCE: 14
ccctgggccc ctcgagtttg atttatttgc tttgtaaaga gaa                    43

<210> SEQ ID NO 15
<211> LENGTH: 51
<212> TYPE: DNA

```
<213> ORGANISM: Artificial Sequence
<220> FEATURE:
<223> OTHER INFORMATION: Primer for PDC2 terminator (C. sonorensis)

<400> SEQUENCE: 15
tggactagtt agatagcaat tcttacttga aaaattaatt gaagcattac c            51

<210> SEQ ID NO 16
<211> LENGTH: 45
<212> TYPE: DNA
<213> ORGANISM: Artificial Sequence
<220> FEATURE:
<223> OTHER INFORMATION: Primer for PDC2 terminator (C. sonorensis)

<400> SEQUENCE: 16
ggcccgcggc cgctaaatat aattatcgct tagttattaa aatgg                  45

<210> SEQ ID NO 17
<211> LENGTH: 20
<212> TYPE: DNA
<213> ORGANISM: Artificial Sequence
<220> FEATURE:
<223> OTHER INFORMATION: Primer for TDH (S. cerevisiae)

<400> SEQUENCE: 17
tgtcatcact gctccatctt                                              20

<210> SEQ ID NO 18
<211> LENGTH: 20
<212> TYPE: DNA
<213> ORGANISM: Artificial Sequence
<220> FEATURE:
<223> OTHER INFORMATION: Primer for TDH (S. cerevisiae)

<400> SEQUENCE: 18
ttaagccttg gcaacatatt                                              20

<210> SEQ ID NO 19
<211> LENGTH: 37
<212> TYPE: DNA
<213> ORGANISM: Artificial Sequence
<220> FEATURE:
<223> OTHER INFORMATION: Primer for PGK1 (C. albicans)

<400> SEQUENCE: 19
gcgatctcga ggtcctagaa tatgtatact aatttgc                           37

<210> SEQ ID NO 20
<211> LENGTH: 39
<212> TYPE: DNA
<213> ORGANISM: Artificial Sequence
<220> FEATURE:
<223> OTHER INFORMATION: Primer for PGK1 (C. albicans)

<400> SEQUENCE: 20
cgcgaattcc catggttagt ttttgttgga aagagcaac                         39

<210> SEQ ID NO 21
<211> LENGTH: 32
<212> TYPE: DNA
<213> ORGANISM: Artificial Sequence
<220> FEATURE:
<223> OTHER INFORMATION: Primer for 26 S rRNA (C. sonorensis)

<400> SEQUENCE: 21
tggactagta aaccaacagg gattgcctta gt                                32
```

<210> SEQ ID NO 22
<211> LENGTH: 33
<212> TYPE: DNA
<213> ORGANISM: Artificial Sequence
<220> FEATURE:
<223> OTHER INFORMATION: Primer for 26 S rRNA (C. sonorensis)

<400> SEQUENCE: 22
ctagtctaga gatcattacg ccagcatcct agg                              33

<210> SEQ ID NO 23
<211> LENGTH: 44
<212> TYPE: DNA
<213> ORGANISM: Artificial sequence
<220> FEATURE:
<223> OTHER INFORMATION: Primers for isolating PDC

<400> SEQUENCE: 23
ccggaattcg atatctgggc wggkaatgcc aaygarttra atgc                  44

<210> SEQ ID NO 24
<211> LENGTH: 44
<212> TYPE: DNA
<213> ORGANISM: Artificial Sequence
<220> FEATURE:
<223> OTHER INFORMATION: Primer for isolating PDC
<220> FEATURE:
<221> NAME/KEY: misc_feature
<222> LOCATION: (21)..(21)
<223> OTHER INFORMATION: n stands for any nucleotide
<220> FEATURE:
<221> NAME/KEY: misc_feature
<222> LOCATION: (33)..(33)
<223> OTHER INFORMATION: n stands for any nucleotide

<400> SEQUENCE: 24
cgcggattca ggcctcagta ngaraawgaa ccngtrttra artc                  44

<210> SEQ ID NO 25
<211> LENGTH: 10
<212> TYPE: PRT
<213> ORGANISM: Artificial Sequence
<220> FEATURE:
<223> OTHER INFORMATION: Conserved PDC region in yeasts

<400> SEQUENCE: 25

Trp Ala Gly Asn Ala Asn Glu Leu Asn Ala
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Conserved PDC region in yeasts

<400> SEQUENCE: 26

Asp Phe Asn Thr Gly Ser Phe Ser Tyr Ser
1               5                   10

<210> SEQ ID NO 27
<211> LENGTH: 18
<212> TYPE: DNA
<213> ORGANISM: Artificial Sequence
<220> FEATURE:
<223> OTHER INFORMATION: Primer for ADH genes

```
<400> SEQUENCE: 27
tctgttmcct acrtaaga                                                 18

<210> SEQ ID NO 28
<211> LENGTH: 20
<212> TYPE: DNA
<213> ORGANISM: Artificial Sequence
<220> FEATURE:
<223> OTHER INFORMATION: Primer for ADH genes

<400> SEQUENCE: 28
gtyggtggtc acgaaggtgc                                               20

<210> SEQ ID NO 29
<211> LENGTH: 32
<212> TYPE: DNA
<213> ORGANISM: Artificial Sequence
<220> FEATURE:
<223> OTHER INFORMATION: Primer for 26 S rRNA (C. sonorensis)

<400> SEQUENCE: 29
tggactagta aaccaacagg gattgcctta gt                                 32

<210> SEQ ID NO 30
<211> LENGTH: 33
<212> TYPE: DNA
<213> ORGANISM: Artificial Sequence
<220> FEATURE:
<223> OTHER INFORMATION: Primer for 26 S rRNA (C. sonorensis)

<400> SEQUENCE: 30
ctagtctaga gatcattacg ccagcatcct agg                                33

<210> SEQ ID NO 31
<211> LENGTH: 37
<212> TYPE: DNA
<213> ORGANISM: Artificial Sequence
<220> FEATURE:
<223> OTHER INFORMATION: Primer for PGK1 sequence (C. albicans)

<400> SEQUENCE: 31
gcgatctcga ggtcctagaa tatgtatact aatttgc                            37

<210> SEQ ID NO 32
<211> LENGTH: 36
<212> TYPE: DNA
<213> ORGANISM: Artificial Sequence
<220> FEATURE:
<223> OTHER INFORMATION: Primer for PGK1 sequence (C. albicans)

<400> SEQUENCE: 32
acttggccat ggtgatagtt attcttctgc aattga                             36

<210> SEQ ID NO 33
<211> LENGTH: 1235
<212> TYPE: DNA
<213> ORGANISM: Artificial Sequence
<220> FEATURE:
<223> OTHER INFORMATION: 1,235 kbp NotI digested fragment comprising the
      S. cerevisiae PGK promoter, multiple cloning site, and the Gal10
      terminator.

<400> SEQUENCE: 33
ggccgcggat cgctcttccg ctatcgatta attttttttt ctttcctctt tttattaacc   60
ttaattttta ttttagattc ctgacttcaa ctcaagacgc acagatatta taacatctgc  120
```

```
acaataggca tttgcaagaa ttactcgtga gtaaggaaag agtgaggaac tatcgcatac      180
ctgcatttaa agatgccgat ttgggcgcga atcctttatt ttggcttcac cctcatacta      240
ttatcagggc cagaaaaagg aagtgtttcc ctccttcttg aattgatgtt accctcataa      300
agcacgtggc ctcttatcga gaaagaaatt accgtcgctc gtgatttgtt tgcaaaaaga      360
acaaaactga aaaacccag acacgctcga cttcctgtct tcctattgat tgcagcttcc       420
aatttcgtca cacaacaagg tcctagcgac ggctcacagg ttttgtaaca agcaatcgaa      480
ggttctggaa tggcgggaaa gggtttagta ccacatgcta tgatgcccac tgtgatctcc      540
agagcaaagt tcgttcgatc gtactgttac tctctctctt tcaaacagaa ttgtccgaat      600
cgtgtgacaa caacagcctg ttctcacaca ctcttttctt ctaaccaagg gggtggttta      660
gtttagtaga acctcgtgaa acttacattt acatatatat aaacttgcat aaattggtca      720
atgcaagaaa tacatatttg gtcttttcta attcgtagtt tttcaagttc ttagatgctt      780 tcttttctc tttttttacag atcatcaagg aagtaattat ctacttttta caacaaatct      840
agaattcgga tccggtagat acattgatgc tatcaatcaa gagaactgga agattgtgt       900 aaccttgaaa acggtgaaa cttacgggtc caagaccctc tacagatttt cctgatttgc      960
cagcttacta tccttcttga aaatatgcac tctatatctt ttagttctta attgcaacac     1020
atagatttgc tgtataacga atttatgct attttttaaa tttggagttc agtgataaaa      1080
gtgtcacagc gaatttcctc acatgtagga ccgaattgtt tacaagttct ctgtaccacc     1140
atggagacat caaagattga aaatctatgg aaagatatgg acggtagcaa caagaatata    1200
gcacgagccg cggatttatt tcgttacgca tgcgc                                1235

<210> SEQ ID NO 34
<211> LENGTH: 21
<212> TYPE: DNA
<213> ORGANISM: Artificial Sequence
<220> FEATURE:
<223> OTHER INFORMATION: Primer for LDH isolation (B. megaterium)

<400> SEQUENCE: 34
cctgagtcca cgtcattatt c                                                 21

<210> SEQ ID NO 35
<211> LENGTH: 22
<212> TYPE: DNA
<213> ORGANISM: Artificial Sequence
<220> FEATURE:
<223> OTHER INFORMATION: Primer for LDH isolation (B. megaterium)

<400> SEQUENCE: 35
tgaagctatt tattcttgtt ac                                                22

<210> SEQ ID NO 36
<211> LENGTH: 27
<212> TYPE: DNA
<213> ORGANISM: Artificial Sequence
<220> FEATURE:
<223> OTHER INFORMATION: Primer to introduce restriction sites

<400> SEQUENCE: 36
gctctagatg aaaacacaat ttacacc                                           27

<210> SEQ ID NO 37
<211> LENGTH: 28
<212> TYPE: DNA
```

```
<213> ORGANISM: Artificial Sequence
<220> FEATURE:
<223> OTHER INFORMATION: Primer to introduce restriction sites

<400> SEQUENCE: 37
atggatcctt acacaaaagc tctgtcgc                                      28

<210> SEQ ID NO 38
<211> LENGTH: 26
<212> TYPE: DNA
<213> ORGANISM: Artificial Sequence
<220> FEATURE:
<223> OTHER INFORMATION: Primer for LDH isolation (R. oryzae)

<400> SEQUENCE: 38
ctttattttt ctttacaata taattc                                        26

<210> SEQ ID NO 39
<211> LENGTH: 19
<212> TYPE: DNA
<213> ORGANISM: Artificial Sequence
<220> FEATURE:
<223> OTHER INFORMATION: Primer for LDH isolation (R. oryzae)

<400> SEQUENCE: 39
actagcagtg caaaacatg                                                19

<210> SEQ ID NO 40
<211> LENGTH: 29
<212> TYPE: DNA
<213> ORGANISM: Artificial Sequence
<220> FEATURE:
<223> OTHER INFORMATION: Primer for introduction of restriction sites

<400> SEQUENCE: 40
gctctagatg gtattacact caaaggtcg                                     29

<210> SEQ ID NO 41
<211> LENGTH: 30
<212> TYPE: DNA
<213> ORGANISM: Artificial Sequence
<220> FEATURE:
<223> OTHER INFORMATION: Primer for introduction of restriction sites

<400> SEQUENCE: 41
gctctagatc aacagctact tttagaaaag                                    30

<210> SEQ ID NO 42
<211> LENGTH: 68
<212> TYPE: DNA
<213> ORGANISM: Artificial Sequence
<220> FEATURE:
<223> OTHER INFORMATION: Primer for PGK1 promoter (C. sonorensis)

<400> SEQUENCE: 42
tggactagta catgcatgcg gtgagaaagt agaaagcaaa cattgtatat agtcttttct   60
attattag                                                            68

<210> SEQ ID NO 43
<211> LENGTH: 75
<212> TYPE: DNA
<213> ORGANISM: Artificial Sequence
<220> FEATURE:
<223> OTHER INFORMATION: Primer for TDH1 promoter (C. sonorensis)

<400> SEQUENCE: 43
```

-continued

```
tggactagta catgcatgcg gtgagaaagt agaaagcaaa cattttgttt gatttgtttg      60
ttttgttttt gtttg                                                      75
```

<210> SEQ ID NO 44
<211> LENGTH: 35
<212> TYPE: DNA
<213> ORGANISM: Artificial Sequence
<220> FEATURE:
<223> OTHER INFORMATION: Primer for PGK1 promoter (C. sonorensis)

<400> SEQUENCE: 44

```
acttggccat ggtatatagt cttttctatt attag                                35
```

<210> SEQ ID NO 45
<211> LENGTH: 957
<212> TYPE: DNA
<213> ORGANISM: Bacillus megaterium
<220> FEATURE:
<221> NAME/KEY: CDS
<222> LOCATION: (1)..(957)
<223> OTHER INFORMATION: B. megaterium LDH protein

<400> SEQUENCE: 45

```
atg aaa aca caa ttt aca cca aaa aca cga aaa gtt gcc gtt atc gga       48
Met Lys Thr Gln Phe Thr Pro Lys Thr Arg Lys Val Ala Val Ile Gly
1               5                   10                  15 act ggt ttt gtt ggc tca agc tac gct ttt tca atg gtg aat caa ggt       96
Thr Gly Phe Val Gly Ser Ser Tyr Ala Phe Ser Met Val Asn Gln Gly
            20                  25                  30 att gcc aat gaa tta gtg tta atc gat atg aac aaa gaa aaa gca gaa      144
Ile Ala Asn Glu Leu Val Leu Ile Asp Met Asn Lys Glu Lys Ala Glu
        35                  40                  45 ggt gaa gca cgt gat atc aat cat gga atg cca ttt gcc aca ccg atg      192
Gly Glu Ala Arg Asp Ile Asn His Gly Met Pro Phe Ala Thr Pro Met
    50                  55                  60 aaa atc tgg gct gga gat tat aaa gac tgt gct gac gct gat tta gca      240
Lys Ile Trp Ala Gly Asp Tyr Lys Asp Cys Ala Asp Ala Asp Leu Ala
65                  70                  75                  80 gtt att aca gcg ggc gct aat caa gct cca ggg gaa aca cgc tta gat      288
Val Ile Thr Ala Gly Ala Asn Gln Ala Pro Gly Glu Thr Arg Leu Asp
                85                  90                  95 cta gtt gaa aaa aac gtt aaa att ttc gaa tgc att gta aaa gat att      336
Leu Val Glu Lys Asn Val Lys Ile Phe Glu Cys Ile Val Lys Asp Ile
            100                 105                 110 atg aac agc gga ttt gac ggc atc att tta gtg gca aca aat cca gtt      384
Met Asn Ser Gly Phe Asp Gly Ile Ile Leu Val Ala Thr Asn Pro Val
        115                 120                 125 gat att ctc gca cac gtt aca caa aaa gta tca gga tta cca aac gga      432
Asp Ile Leu Ala His Val Thr Gln Lys Val Ser Gly Leu Pro Asn Gly
    130                 135                 140 cgg gta att ggt tca gga acg att ctt gac aca gct cgc ttc cgc tac      480
Arg Val Ile Gly Ser Gly Thr Ile Leu Asp Thr Ala Arg Phe Arg Tyr
145                 150                 155                 160 ttg tta agc gac tat ttc gaa gta gat tct cgc aac gtc cac gct tat      528
Leu Leu Ser Asp Tyr Phe Glu Val Asp Ser Arg Asn Val His Ala Tyr
                165                 170                 175 att atg ggg gaa cat gga gat acg gaa ttt cct gtt tgg agc cac gcg      576
Ile Met Gly Glu His Gly Asp Thr Glu Phe Pro Val Trp Ser His Ala
            180                 185                 190 caa att ggc ggt gtg aag ctc gaa cat ttt atc aat act gcc gct att      624
Gln Ile Gly Gly Val Lys Leu Glu His Phe Ile Asn Thr Ala Ala Ile
```

```
                195                 200                 205
gaa aaa gaa ccg gat atg cag cat cta ttc gaa caa acc cgc gat gcg     672
Glu Lys Glu Pro Asp Met Gln His Leu Phe Glu Gln Thr Arg Asp Ala
    210                 215                 220 gct tac cat att att aat cga aaa gga gcg act tat tac gga att gca     720
Ala Tyr His Ile Ile Asn Arg Lys Gly Ala Thr Tyr Tyr Gly Ile Ala
225                 230                 235                 240 atg ggg ctt gta cgc att acc aag gct att tta gat gat gaa aat tct     768
Met Gly Leu Val Arg Ile Thr Lys Ala Ile Leu Asp Asp Glu Asn Ser
                245                 250                 255 att tta aca gta tct gct tta tta gaa gga caa tac ggt att tct gat     816
Ile Leu Thr Val Ser Ala Leu Leu Glu Gly Gln Tyr Gly Ile Ser Asp
            260                 265                 270 gtg tat atc ggc gta cca gct atc att aat aaa aac ggc gtg cgt caa     864
Val Tyr Ile Gly Val Pro Ala Ile Ile Asn Lys Asn Gly Val Arg Gln
        275                 280                 285 att att gaa ttg aat tta act cct cac gaa cag cag cag ctc gag cac     912
Ile Ile Glu Leu Asn Leu Thr Pro His Glu Gln Gln Gln Leu Glu His
    290                 295                 300 tct gct agc att ctt aag caa act cgc gac aga gct ttt gtg taa         957
Ser Ala Ser Ile Leu Lys Gln Thr Arg Asp Arg Ala Phe Val
305                 310                 315
```

<210> SEQ ID NO 46
<211> LENGTH: 318
<212> TYPE: PRT
<213> ORGANISM: Bacillus megaterium

<400> SEQUENCE: 46

```
Met Lys Thr Gln Phe Thr Pro Lys Thr Arg Lys Val Ala Val Ile Gly
1               5                   10                  15

Thr Gly Phe Val Gly Ser Ser Tyr Ala Phe Ser Met Val Asn Gln Gly
                20                  25                  30

Ile Ala Asn Glu Leu Val Leu Ile Asp Met Asn Lys Glu Lys Ala Glu
            35                  40                  45

Gly Glu Ala Arg Asp Ile Asn His Gly Met Pro Phe Ala Thr Pro Met
        50                  55                  60

Lys Ile Trp Ala Gly Asp Tyr Lys Asp Cys Ala Asp Ala Asp Leu Ala
65                  70                  75                  80

Val Ile Thr Ala Gly Ala Asn Gln Ala Pro Gly Glu Thr Arg Leu Asp
                85                  90                  95

Leu Val Glu Lys Asn Val Lys Ile Phe Glu Cys Ile Val Lys Asp Ile
            100                 105                 110

Met Asn Ser Gly Phe Asp Gly Ile Ile Leu Val Ala Thr Asn Pro Val
        115                 120                 125

Asp Ile Leu Ala His Val Thr Gln Lys Val Ser Gly Leu Pro Asn Gly
    130                 135                 140

Arg Val Ile Gly Ser Gly Thr Ile Leu Asp Thr Ala Arg Phe Arg Tyr
145                 150                 155                 160

Leu Leu Ser Asp Tyr Phe Glu Val Asp Ser Arg Asn Val His Ala Tyr
                165                 170                 175

Ile Met Gly Glu His Gly Asp Thr Glu Phe Pro Val Trp Ser His Ala
            180                 185                 190

Gln Ile Gly Gly Val Lys Leu Glu His Phe Ile Asn Thr Ala Ala Ile
        195                 200                 205

Glu Lys Glu Pro Asp Met Gln His Leu Phe Glu Gln Thr Arg Asp Ala
    210                 215                 220
```

```
Ala Tyr His Ile Ile Asn Arg Lys Gly Ala Thr Tyr Tyr Gly Ile Ala
225                 230                 235                 240

Met Gly Leu Val Arg Ile Thr Lys Ala Ile Leu Asp Asp Glu Asn Ser
                245                 250                 255

Ile Leu Thr Val Ser Ala Leu Leu Glu Gly Gln Tyr Gly Ile Ser Asp
                260                 265                 270

Val Tyr Ile Gly Val Pro Ala Ile Ile Asn Lys Asn Gly Val Arg Gln
            275                 280                 285

Ile Ile Glu Leu Asn Leu Thr Pro His Glu Gln Gln Gln Leu Glu His
        290                 295                 300

Ser Ala Ser Ile Leu Lys Gln Thr Arg Asp Arg Ala Phe Val
305                 310                 315
```

<210> SEQ ID NO 47
<211> LENGTH: 963
<212> TYPE: DNA
<213> ORGANISM: Rhizopus oryzae
<220> FEATURE:
<221> NAME/KEY: CDS
<222> LOCATION: (1)..(963)
<223> OTHER INFORMATION: R. oryzae LDH protein

<400> SEQUENCE: 47

```
atg gta tta cac tca aag gtc gcc atc gtt gga gct ggt gca gta gga        48
Met Val Leu His Ser Lys Val Ala Ile Val Gly Ala Gly Ala Val Gly
1               5                   10                  15 gcc tcc act gct tat gca ctt atg ttt aaa aac att tgt aca gaa atc        96
Ala Ser Thr Ala Tyr Ala Leu Met Phe Lys Asn Ile Cys Thr Glu Ile
            20                  25                  30 att att gtt gat gtt aat cct gac atc gtt caa gct caa gtc ctt gac       144
Ile Ile Val Asp Val Asn Pro Asp Ile Val Gln Ala Gln Val Leu Asp
        35                  40                  45 ctt gca gat gct gcc agt ata agt cac acg ccc atc cga gca ggt agc       192
Leu Ala Asp Ala Ala Ser Ile Ser His Thr Pro Ile Arg Ala Gly Ser
    50                  55                  60 gca gag gag gca ggg cag gca gat att gtt gtc atc acg gcc ggt gcg       240
Ala Glu Glu Ala Gly Gln Ala Asp Ile Val Val Ile Thr Ala Gly Ala
65                  70                  75                  80 aaa caa agg gaa ggt gag cct cgg aca aag ctc att gaa cga aac ttc       288
Lys Gln Arg Glu Gly Glu Pro Arg Thr Lys Leu Ile Glu Arg Asn Phe
                85                  90                  95 aga gtg ttg caa agt atc att ggt ggc atg caa ccc att cga cca gac       336
Arg Val Leu Gln Ser Ile Ile Gly Gly Met Gln Pro Ile Arg Pro Asp
            100                 105                 110 gca gtc atc ttg gtg gta gca aat cca gtc gat atc ttg aca cac att       384
Ala Val Ile Leu Val Val Ala Asn Pro Val Asp Ile Leu Thr His Ile
        115                 120                 125 gca aag acc ctc tct gga ctg cct cca aac cag gtc att ggc tcc ggt       432
Ala Lys Thr Leu Ser Gly Leu Pro Pro Asn Gln Val Ile Gly Ser Gly
    130                 135                 140 acc tac ctt gac acg acc cgt ctt cgc gtc cat ctt ggc gat gtc ttt       480
Thr Tyr Leu Asp Thr Thr Arg Leu Arg Val His Leu Gly Asp Val Phe
145                 150                 155                 160 gat gtc aat cct caa tcg gtc cat gct ttt gtc ttg ggt gaa cat ggg       528
Asp Val Asn Pro Gln Ser Val His Ala Phe Val Leu Gly Glu His Gly
                165                 170                 175 gat tcc cag atg atc gct tgg gag gct gct tcg att ggt ggc cag ccg       576
Asp Ser Gln Met Ile Ala Trp Glu Ala Ala Ser Ile Gly Gly Gln Pro
            180                 185                 190
```

```
ttg aca agt ttc ccg gaa ttc gca aag ctg gat aaa aca gca att tca    624
Leu Thr Ser Phe Pro Glu Phe Ala Lys Leu Asp Lys Thr Ala Ile Ser
        195                 200                 205 aaa gcg ata tca ggt aaa gcg atg gag atc att cgt ttg aaa gga gcc    672
Lys Ala Ile Ser Gly Lys Ala Met Glu Ile Ile Arg Leu Lys Gly Ala
210                 215                 220 acg ttt tat gga att ggt gcc tgt gca gcg gat tta gtg cac act atc    720
Thr Phe Tyr Gly Ile Gly Ala Cys Ala Ala Asp Leu Val His Thr Ile
225                 230                 235                 240 atg ttg aat agg aaa tca gta cat cca gtt tct gtt tat gtt gaa aag    768
Met Leu Asn Arg Lys Ser Val His Pro Val Ser Val Tyr Val Glu Lys
            245                 250                 255 tat gga gcc act ttt tct atg cct gct aaa ctt gga tgg aga ggt gtt    816
Tyr Gly Ala Thr Phe Ser Met Pro Ala Lys Leu Gly Trp Arg Gly Val
        260                 265                 270 gaa cag atc tat gaa gta cca ctg acg gaa gaa gaa gcg ttg ctt        864
Glu Gln Ile Tyr Glu Val Pro Leu Thr Glu Glu Glu Ala Leu Leu
    275                 280                 285 gta aaa tct gta gag gca ttg aaa tca gtt gaa tat tca tct aca aaa    912
Val Lys Ser Val Glu Ala Leu Lys Ser Val Glu Tyr Ser Ser Thr Lys
290                 295                 300 gtt cca gaa aaa aag gtt cat gct act tcc ttt tct aaa agt agc tgt    960
Val Pro Glu Lys Lys Val His Ala Thr Ser Phe Ser Lys Ser Ser Cys
305                 310                 315                 320 tga                                                                 963
```

<210> SEQ ID NO 48
<211> LENGTH: 320
<212> TYPE: PRT
<213> ORGANISM: Rhizopus oryzae

<400> SEQUENCE: 48

```
Met Val Leu His Ser Lys Val Ala Ile Val Gly Ala Gly Ala Val Gly
1               5                   10                  15

Ala Ser Thr Ala Tyr Ala Leu Met Phe Lys Asn Ile Cys Thr Glu Ile
            20                  25                  30

Ile Ile Val Asp Val Asn Pro Asp Ile Val Gln Ala Gln Val Leu Asp
        35                  40                  45

Leu Ala Asp Ala Ala Ser Ile Ser His Thr Pro Ile Arg Ala Gly Ser
    50                  55                  60

Ala Glu Glu Ala Gly Gln Ala Asp Ile Val Ile Thr Ala Gly Ala
65                  70                  75                  80

Lys Gln Arg Glu Gly Glu Pro Arg Thr Lys Leu Ile Glu Arg Asn Phe
                85                  90                  95

Arg Val Leu Gln Ser Ile Gly Gly Met Gln Pro Ile Arg Pro Asp
            100                 105                 110

Ala Val Ile Leu Val Val Ala Asn Pro Val Asp Ile Leu Thr His Ile
        115                 120                 125

Ala Lys Thr Leu Ser Gly Leu Pro Pro Asn Gln Val Ile Gly Ser Gly
    130                 135                 140

Thr Tyr Leu Asp Thr Thr Arg Leu Arg Val His Leu Gly Asp Val Phe
145                 150                 155                 160

Asp Val Asn Pro Gln Ser Val His Ala Phe Val Leu Gly Glu His Gly
                165                 170                 175

Asp Ser Gln Met Ile Ala Trp Glu Ala Ala Ser Ile Gly Gly Gln Pro
            180                 185                 190

Leu Thr Ser Phe Pro Glu Phe Ala Lys Leu Asp Lys Thr Ala Ile Ser
```

```
                195                 200                 205
Lys Ala Ile Ser Gly Lys Ala Met Glu Ile Ile Arg Leu Lys Gly Ala
        210                 215                 220

Thr Phe Tyr Gly Ile Gly Ala Cys Ala Ala Asp Leu Val His Thr Ile
225                 230                 235                 240

Met Leu Asn Arg Lys Ser Val His Pro Val Ser Val Tyr Val Glu Lys
                245                 250                 255

Tyr Gly Ala Thr Phe Ser Met Pro Ala Lys Leu Gly Trp Arg Gly Val
        260                 265                 270

Glu Gln Ile Tyr Glu Val Pro Leu Thr Glu Glu Glu Ala Leu Leu
    275                 280                 285

Val Lys Ser Val Glu Ala Leu Lys Ser Val Glu Tyr Ser Ser Thr Lys
        290                 295                 300

Val Pro Glu Lys Lys Val His Ala Thr Ser Phe Ser Lys Ser Cys
305                 310                 315                 320

<210> SEQ ID NO 49
<211> LENGTH: 972
<212> TYPE: DNA
<213> ORGANISM: Lactobacillus helveticus
<220> FEATURE:
<221> NAME/KEY: CDS
<222> LOCATION: (1)..(972)
<223> OTHER INFORMATION: L. helveticus LDH protein.

<400> SEQUENCE: 49 atg gca aga gag gaa aaa cct cgt aaa gtt att tta gtc ggt gat ggt        48
Met Ala Arg Glu Glu Lys Pro Arg Lys Val Ile Leu Val Gly Asp Gly
1               5                   10                  15 gct gta ggt tct acc ttt gca ttt tca atg gta caa caa ggt atc gct        96
Ala Val Gly Ser Thr Phe Ala Phe Ser Met Val Gln Gln Gly Ile Ala
                20                  25                  30 gaa gaa tta ggt att atc gat atc gct aag gaa cac gtt gaa ggt gac        144
Glu Glu Leu Gly Ile Ile Asp Ile Ala Lys Glu His Val Glu Gly Asp
            35                  40                  45 gca atc gat tta gct gac gca act cct tgg act tct cca aag aac att        192
Ala Ile Asp Leu Ala Asp Ala Thr Pro Trp Thr Ser Pro Lys Asn Ile
        50                  55                  60 tac gca gct gac tac cca gat tgt aag gat gct gac tta gtt gtt att        240
Tyr Ala Ala Asp Tyr Pro Asp Cys Lys Asp Ala Asp Leu Val Val Ile
65                  70                  75                  80 act gct ggt gct cca caa aag cca ggc gaa act cgt ctt gat ctt gtt        288
Thr Ala Gly Ala Pro Gln Lys Pro Gly Glu Thr Arg Leu Asp Leu Val
                85                  90                  95 aac aag aac ttg aag att tta tca tca atc gtt gaa cca gtt gtt gaa        336
Asn Lys Asn Leu Lys Ile Leu Ser Ser Ile Val Glu Pro Val Val Glu
            100                 105                 110 tca ggt ttt gaa ggt att ttc tta gta gtt gct aac cca gtt gat atc        384
Ser Gly Phe Glu Gly Ile Phe Leu Val Val Ala Asn Pro Val Asp Ile
        115                 120                 125 tta act cac gca act tgg aga atg tca ggc ttc cct aag gat cgt gtt        432
Leu Thr His Ala Thr Trp Arg Met Ser Gly Phe Pro Lys Asp Arg Val
130                 135                 140 atc ggt tca ggt act tca ctt gat act ggt cgt ctt caa aaa gtt att        480
Ile Gly Ser Gly Thr Ser Leu Asp Thr Gly Arg Leu Gln Lys Val Ile
145                 150                 155                 160 ggt aaa atg gaa aac gtt gac cca agt tca gtt aat gca tac atg ctt        528
Gly Lys Met Glu Asn Val Asp Pro Ser Ser Val Asn Ala Tyr Met Leu
                165                 170                 175
```

-continued

```
ggt gaa cac ggt gat act gaa ttc cca gca tgg agc tac aac aat gtt    576
Gly Glu His Gly Asp Thr Glu Phe Pro Ala Trp Ser Tyr Asn Asn Val
            180                 185                 190 gct ggc gta aag gtt gct gac tgg gtt aag gct cac aac atg cct gaa    624
Ala Gly Val Lys Val Ala Asp Trp Val Lys Ala His Asn Met Pro Glu
        195                 200                 205 tct aag ctt gaa gac atc cac caa gaa gtt aag gac atg gct tac gac    672
Ser Lys Leu Glu Asp Ile His Gln Glu Val Lys Asp Met Ala Tyr Asp
    210                 215                 220 att att aac aag aaa ggt gct acc ttc tac ggt atc ggt act gct tca    720
Ile Ile Asn Lys Lys Gly Ala Thr Phe Tyr Gly Ile Gly Thr Ala Ser
225                 230                 235                 240 gca atg atc gct aag gct atc ttg aac gat gaa cac cgt gta ctt cca    768
Ala Met Ile Ala Lys Ala Ile Leu Asn Asp Glu His Arg Val Leu Pro
                245                 250                 255 ctt tca gta cca atg gat ggt gaa tat ggt tta cac gat ctt cac atc    816
Leu Ser Val Pro Met Asp Gly Glu Tyr Gly Leu His Asp Leu His Ile
            260                 265                 270 ggt act cct gca gtt gtt ggc cgc aag ggt ctt gaa caa gtt atc gaa    864
Gly Thr Pro Ala Val Val Gly Arg Lys Gly Leu Glu Gln Val Ile Glu
        275                 280                 285 atg cca tta agc gat aag gaa caa gaa tta atg act gct tca gca gat    912
Met Pro Leu Ser Asp Lys Glu Gln Glu Leu Met Thr Ala Ser Ala Asp
    290                 295                 300 caa tta aag aag gtt atg gac aag gcc ttc aaa gaa act ggc gtt aag    960
Gln Leu Lys Lys Val Met Asp Lys Ala Phe Lys Glu Thr Gly Val Lys
305                 310                 315                 320 gtt cgt caa taa                                                    972
Val Arg Gln
```

<210> SEQ ID NO 50
<211> LENGTH: 323
<212> TYPE: PRT
<213> ORGANISM: Lactobacillus helveticus

<400> SEQUENCE: 50

```
Met Ala Arg Glu Glu Lys Pro Arg Lys Val Ile Leu Val Gly Asp Gly
1               5                   10                  15

Ala Val Gly Ser Thr Phe Ala Phe Ser Met Val Gln Gln Gly Ile Ala
            20                  25                  30

Glu Leu Gly Ile Ile Asp Ile Ala Lys Glu His Val Glu Gly Asp
        35                  40                  45

Ala Ile Asp Leu Ala Asp Ala Thr Pro Trp Thr Ser Pro Lys Asn Ile
    50                  55                  60

Tyr Ala Ala Asp Tyr Pro Asp Cys Lys Asp Ala Asp Leu Val Val Ile
65                  70                  75                  80

Thr Ala Gly Ala Pro Gln Lys Pro Gly Glu Thr Arg Leu Asp Leu Val
                85                  90                  95

Asn Lys Asn Leu Lys Ile Leu Ser Ser Ile Val Glu Pro Val Val Glu
            100                 105                 110

Ser Gly Phe Glu Gly Ile Phe Leu Val Val Ala Asn Pro Val Asp Ile
        115                 120                 125

Leu Thr His Ala Thr Trp Arg Met Ser Gly Phe Pro Lys Asp Arg Val
    130                 135                 140

Ile Gly Ser Gly Thr Ser Leu Asp Thr Gly Arg Leu Gln Lys Val Ile
145                 150                 155                 160

Gly Lys Met Glu Asn Val Asp Pro Ser Ser Val Asn Ala Tyr Met Leu
                165                 170                 175
```

```
Gly Glu His Gly Asp Thr Glu Phe Pro Ala Trp Ser Tyr Asn Asn Val
            180                 185                 190

Ala Gly Val Lys Val Ala Asp Trp Val Lys Ala His Asn Met Pro Glu
        195             200                 205

Ser Lys Leu Glu Asp Ile His Gln Glu Val Lys Asp Met Ala Tyr Asp
    210             215                 220

Ile Ile Asn Lys Lys Gly Ala Thr Phe Tyr Gly Ile Gly Thr Ala Ser
225             230                 235                 240

Ala Met Ile Ala Lys Ala Ile Leu Asn Asp Glu His Arg Val Leu Pro
            245                 250                 255

Leu Ser Val Pro Met Asp Gly Glu Tyr Gly Leu His Asp Leu His Ile
            260                 265                 270

Gly Thr Pro Ala Val Val Gly Arg Lys Gly Leu Glu Gln Val Ile Glu
            275                 280                 285

Met Pro Leu Ser Asp Lys Glu Gln Glu Leu Met Thr Ala Ser Ala Asp
    290                 295                 300

Gln Leu Lys Lys Val Met Asp Lys Ala Phe Lys Glu Thr Gly Val Lys
305                 310                 315                 320

Val Arg Gln
```

METHODS AND MATERIALS FOR THE PRODUCTION OF ORGANIC PRODUCTS IN CELLS OF *CANDIDA* SPECIES

This application is a continuation-in-part of U.S. patent application Ser. No. 09/992,430, filed Nov. 23, 2001, which claims priority to U.S. Provisional Application Ser. No. 60/252,541, filed Nov. 22, 2000.

BACKGROUND OF THE INVENTION

The use of microorganisms for synthesizing industrially important organic products is well known. Biosynthetic approaches for producing organic products can be extremely efficient when compared to large-scale chemical synthesis. Advantages a biosynthetic approach may have over a chemical synthetic approach for manufacturing an organic product include more rapid and more efficient product yield, isomeric purity, and reduced cost (see Thomas et al., 2002, *Trends Biotechnol.* 20: 238–42).

Lactic acid has wide industrial applicability, including uses in chemical processing and synthesis, cosmetics, pharmaceuticals, plastics, and food production. Lactic acid is a relatively simple organic molecule, and can be produced either by chemical synthesis or by fermentation in microorganisms (biosynthesis). As genetic manipulation of microorganisms has become more advanced, fermentation processes for lactic acid production have become commercially preferred over chemical synthesis. One reason for this preference is that using genetically modified microorganisms enables production of optically pure (i.e., either the L(+) or D(−) isomer) product. Such methods obviate the need for separating racemic product mixtures, thereby reducing cost.

Nevertheless, the use of microorganisms for producing organic products has certain limitations. For example, bacteria can produce large quantities of organic products under fermentation conditions, but the accumulation of organic products within the bacteria itself and in the growth medium can inhibit proliferation of the bacteria, or cause cell death. Even when more robust organisms are engineered and used for production, such as the acidophilic yeast *Saccharomyces cerevisiae*, organic products can lead to cell growth suppression, reducing overall yield of organic product. Thus, there remains a need in the art for robust microorganisms that are amenable to genetic manipulation, for use in bioreactors and with other biosynthetic methods for producing industrially important organic products.

SUMMARY OF THE INVENTION

This invention provides methods and reagents, particularly cells and recombinant cells, for producing organic products by biosynthesis. The invention specifically provides recombinant nucleic acid constructs encoding at least one protein useful for the synthesis of an organic product, cells comprising said constructs, particularly Crabtree-negative cells, methods for making such cells, methods for culturing such cells, and methods and reagents for synthesizing numerous organic products in vivo.

In one aspect, the invention provides recombinant nucleic acid constructs comprising a sequence encoding at least one protein useful for the synthesis of an organic product. In a preferred embodiment, the recombinant nucleic acid construct encodes lactate dehydrogenase. In one embodiment of this aspect, the recombinant nucleic acid construct comprises a promoter operably linked to the nucleic acid encoding a protein useful for synthesis of an organic product, wherein the promoter is a promoter from a *Candida* species, preferably the *Candida* species that comprises the recombinant nucleic acid construct.

In another aspect, the invention provides a transformed Crabtree-negative cell from the genera *Candida*, comprising the recombinant nucleic acid construct encoding at least one protein useful for the synthesis of an organic product. In a preferred embodiment, the recombinant nucleic acid construct encodes lactate dehydrogenase. In one embodiment of this aspect, the recombinant nucleic acid construct comprises a promoter operably linked to the nucleic acid encoding a protein useful for synthesis of an organic product, wherein the promoter is a promoter from a *Candida* species, preferably the *Candida* species that comprises the recombinant nucleic acid construct. In another aspect, the invention provides a cell of a *Candida* species genetically manipulated so that it has reduced efficiency in metabolizing pyruvate to ethanol. In preferred embodiments of this aspect of the invention, the cell further comprises a recombinant nucleic acid construct of the invention encoding at least one protein useful for the synthesis of an organic product. In a preferred embodiment, the recombinant nucleic acid construct encodes lactate dehydrogenase. In one embodiment of this aspect, the recombinant nucleic acid construct comprises a promoter operably linked to the nucleic acid encoding a protein useful for synthesis of an organic product, wherein the promoter is a promoter from a *Candida* species, preferably the *Candida* species that comprises the recombinant nucleic acid construct.

In another aspect, the invention provides methods for producing organic products comprising fermenting a Crabtree-negative cell from the genera *Candida* comprising a recombinant nucleic acid construct of the invention under conditions that allow for the biosynthesis of said organic products. In preferred embodiments of this aspect of the invention, the organic product is lactic acid. In a preferred embodiment, the recombinant nucleic acid construct encodes lactate dehydrogenase. In one embodiment of this aspect, the recombinant nucleic acid construct comprises a promoter operably linked to the nucleic acid encoding a protein useful for synthesis of an organic product, wherein the promoter is a promoter from a *Candida* species, preferably the *Candida* species that comprises the recombinant nucleic acid construct.

It is an advantage of this invention that the transformed cells provided herein exhibit the "Crabtree negative" phenotype. Crabtree-negative organisms are characterized by the ability to be induced into an increased fermentative state. Both naturally occurring organisms and genetically modified organisms can be characterized as Crabtree-negative. The Crabtree effect is defined as oxygen consumption inhibition in a microorganism when the microorganism is cultured under aerobic conditions in the presence of a high concentration of glucose (e.g. >5 mM glucose). Crabtree-positive organisms continue to ferment (rather than respire) irrespective of oxygen availability in the presence of glucose, while Crabtree-negative organisms do not exhibit glucose-mediated inhibition of oxygen consumption. This characteristic is useful for organic product synthesis, since it permits cells to be grown at high substrate concentrations but to retain the beneficial energetic effects of oxidative phosphorylation. Many yeasts and fungi have the Crabtree-negative phenotype including the non-limiting examples of genera *Kluyveromyces, Pichia, Hansenula, Torulopsis, Yamadazyma,* and *Candida*.

*Candida* species, which are variously characterized as yeasts and dimorphic fungi in the art, can exhibit the Crabtree-negative phenotype (Franzblau & Sinclair, 1983, *Mycopathologia* 82: 185–190). Certain species can ferment glucose, as well as alternative carbon sources, can grow at elevated temperatures (i.e., greater than 37° C.), and can tolerate low pH stress. *Candida* species have several of the desirable characteristics of an organism to be used in biosynthetic methods of organic product manufacture: amenability to genetic manipulation, ability to process a variety of carbon sources, Crabtree-negative phenotype, and ability to proliferate under various environmental stresses.

Specific preferred embodiments of the present invention will become evident from the following more detailed description of certain preferred embodiments and the claims.

BRIEF DESCRIPTION OF THE DRAWINGS

FIG. 1 is a schematic diagram of the vector described as pMI260, comprising the G418 resistance-coding gene driven by the PGK promoter (*S. cerevisiae*) and linked to the GAL10 (*S. cerevisiae*) terminator.

FIG. 2 is a schematic diagram of the vector described as pMI268, comprising the G418 resistance-coding gene driven by the PGK promoter (*C. sonorensis*) and linked to the GAL10 (*S. cerevisiae*) terminator.

FIG. 3 is a schematic diagram of the vector described as pMI269, comprising the G418 resistance-coding gene driven by the TDH promoter (*C. sonorensis*) and linked to the GAL10 (*S. cerevisiae*) terminator.

FIG. 4 is a schematic diagram of the vector described as pMI270, comprising the hygromycin resistance-coding gene driven by the PGK promoter (*C. sonorensis*) and linked to the GAL10 (*S. cerevisiae*) terminator.

FIG. 5 is a schematic diagram of the vector described as pMI234, comprising the MEL5 (*S. cerevisiae*) gene driven by the PGK promoter (*C. sonorensis*).

FIG. 6 is a schematic diagram of the vector described as pMI238, comprising the MEL5 (*S. cerevisiae*) gene driven by the TDH promoter (*C. sonorensis*).

FIG. 7 is a schematic diagram of the vector described as pMI271, comprising the hygromycin resistance-coding gene driven by the TDH promoter (*C. sonorensis*) and linked to the GAL10 (*S. cerevisiae*) terminator.

FIG. 8 is a schematic diagram of the vector described as pMI246, comprising the MEL5 (*S. cerevisiae*) and LDH (*L. helveticus*) genes each driven by the PGK promoter (*C. sonorensis*). The LDH gene is linked to the CYC1 terminator, which is upstream from an S26 rRNA (*C. sonorensis*) region.

FIG. 9 is a schematic diagram of the vector described as pMI247, comprising the MEL5 (*S. cerevisiae*) gene driven by the TDH promoter (*C. sonorensis*) and the LDH (*L. helveticus*) gene driven by the PGK promoter (*C. sonorensis*). The LDH gene is linked to the CYC1 terminator, which is upstream from an S26 rRNA (*C. sonorensis*) region.

FIG. 10 is a schematic diagram of the vector described as pMI257, comprising the MEL5 (*S. cerevisiae*) gene driven by the PGK promoter (*C. sonorensis*) and the LDH (*L. helveticus*) gene driven by the PGK promoter (*C. sonorensis*). The LDH gene is linked to the CYC1 terminator. This entire expression cassette is inserted between the PDC1 promoter and terminator (*C. sonorensis*).

FIG. 11 is a schematic diagram of the vector described as pMI265, comprising the MEL5 (*S. cerevisiae*) gene driven by the PGK promoter (*C. sonorensis*) and the LDH (*B. megaterium;* from vector pVR24) gene driven by the PGK promoter (*C. sonorensis*). The LDH gene is linked to the PDC1 (*C. sonorensis*) terminator. This entire expression cassette is inserted between the PDC1 promoter and terminator (*C. sonorensis*).

FIG. 12 is a schematic diagram of the vector described as pMI266, comprising the MEL5 (*S. cerevisiae*) gene driven by the PGK promoter (*C. sonorensis*) and the LDH (*R. oryzae;* from vector pVR27) gene driven by the PGK promoter (*C. sonorensis*). The LDH gene is linked to the PDC1 (*C. sonorensis*) terminator. This entire expression cassette is inserted between the PDC1 promoter and terminator (*C. sonorensis*).

FIG. 13 is a schematic diagram of the vector described as pMI267, comprising the MEL5 (*S. cerevisiae*) gene driven by the PGK promoter (*C. sonorensis*). This expression cassette is inserted between the PDC1 promoter and terminator (*C. sonorensis*).

FIG. 14 is a schematic diagram of the vector described as pMI278, comprising the G418 resistance-coding gene driven by the TDH promoter (*C. sonorensis*), operatively linked to the MEL5 terminator, and the LDH (*B. megaterium*) gene driven by the PGK promoter (*C. sonorensis*). The LDH gene is linked to the GAL10 (*S. cerevisiae*) terminator.

FIG. 15 is a schematic diagram of the vector described as pMI286, comprising the G418 resistance-coding gene driven by the TDH promoter (*C. sonorensis*), operatively linked to the MEL5 (*S. cerevisiae*) terminator, and the LDH (*B. megaterium*) gene driven by the PGK promoter (*C. sonorensis*). The LDH gene is linked to the GAL10 (*S. cerevisiae*) terminator. This entire expression cassette is inserted between the PDC2 promoter and terminator (*C. sonorensis*).

FIG. 16 is a schematic diagram of the vector described as pMI287, comprising the G418 resistance-coding gene driven by the TDH promoter (*C. sonorensis*), operatively linked to the MEL5 (*S. cerevisiae*) terminator. This expression cassette is inserted between the PDC2 promoter and terminator (*C. sonorensis*).

FIG. 17 is a schematic diagram of the vector described as pMI288, comprising the G418 resistance-coding gene driven by the TDH promoter (*C. sonorensis*), operatively linked to the MEL5 (*S. cerevisiae*) terminator, and the LDH (*L. helveticus*) gene driven by the PGK promoter (*C. sonorensis*). The LDH gene is linked to the CYC1 terminator. This entire expression cassette is inserted between the PDC2 promoter and terminator (*C. sonorensis*).

FIG. 18 is a schematic diagram of the vector described as pMI256, comprising the MEL5 (*S. cerevisiae*) gene driven by the PGK promoter (*C. sonorensis*) and the LDH (*L. helveticus*) gene driven by the PGK promoter (*C. sonorensis*). The LDH gene is linked to the CYC1 terminator. This entire expression cassette is inserted upstream of the PDC1 terminator (*C. sonorensis*).

FIG. 19 is a schematic diagram of the vector described as pMI277, comprising the PDC2 promoter (*C. sonorensis*).

FIG. 20 is a schematic diagram of the vector described as pMI279, comprising the G418 resistance-coding gene driven by the TDH promoter (*C. sonorensis*), operatively linked to the MEL5 (*S. cerevisiae*) terminator, and the LDH (*B. megaterium*) gene driven by the PGK promoter (*C. sonorensis*). The LDH gene is linked to the GAL10 terminator (*S. cerevisiae*). This entire expression cassette is inserted downstream of the PDC2 promoter (*C. sonorensis*).

FIG. 21 is a schematic diagram of the vector described as pVR24.

FIG. 22 is a schematic diagram of the vector described as pVR27.

DETAILED DESCRIPTION OF THE INVENTION

Figure 23A:
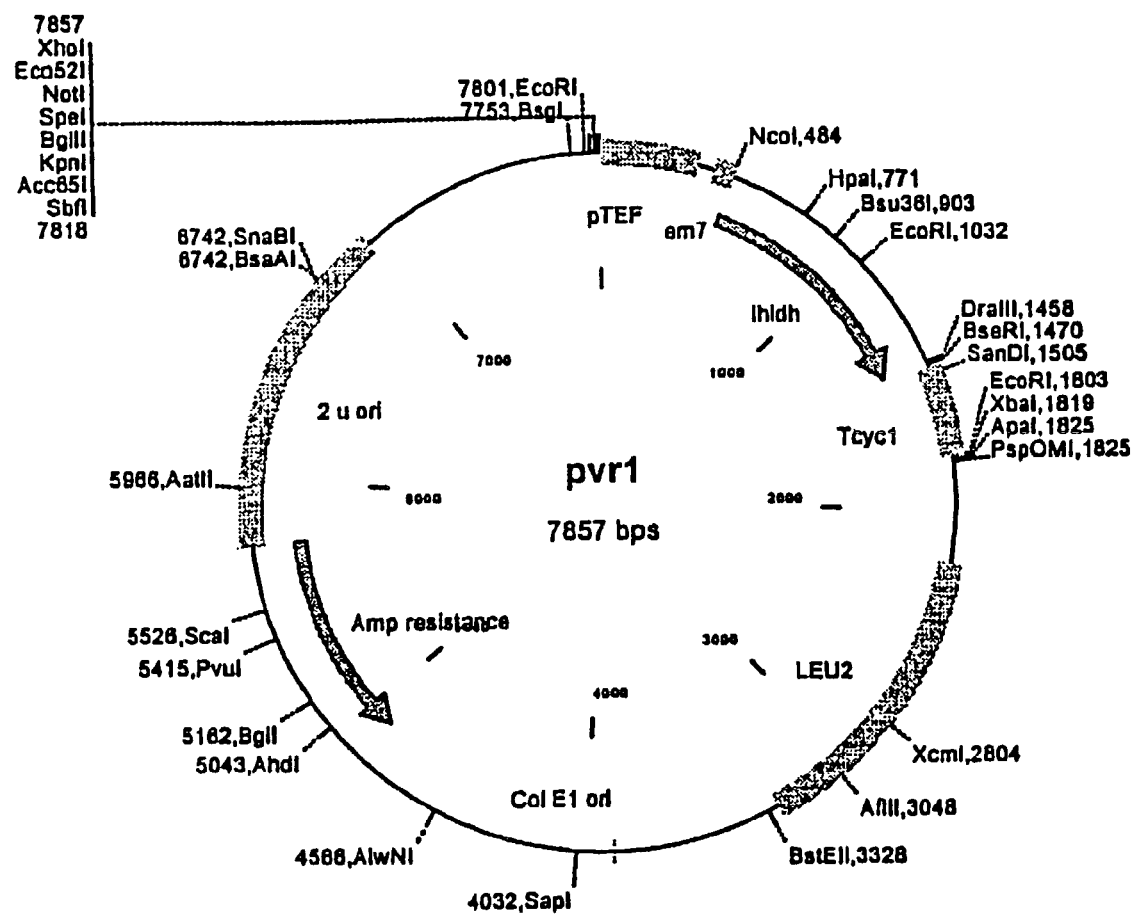
FIGS. 23A–C are schematic diagrams of the vectors including pMI214, pMI203, pMI205, pMI227, pMI233, and pMI234.
Figure 23A:
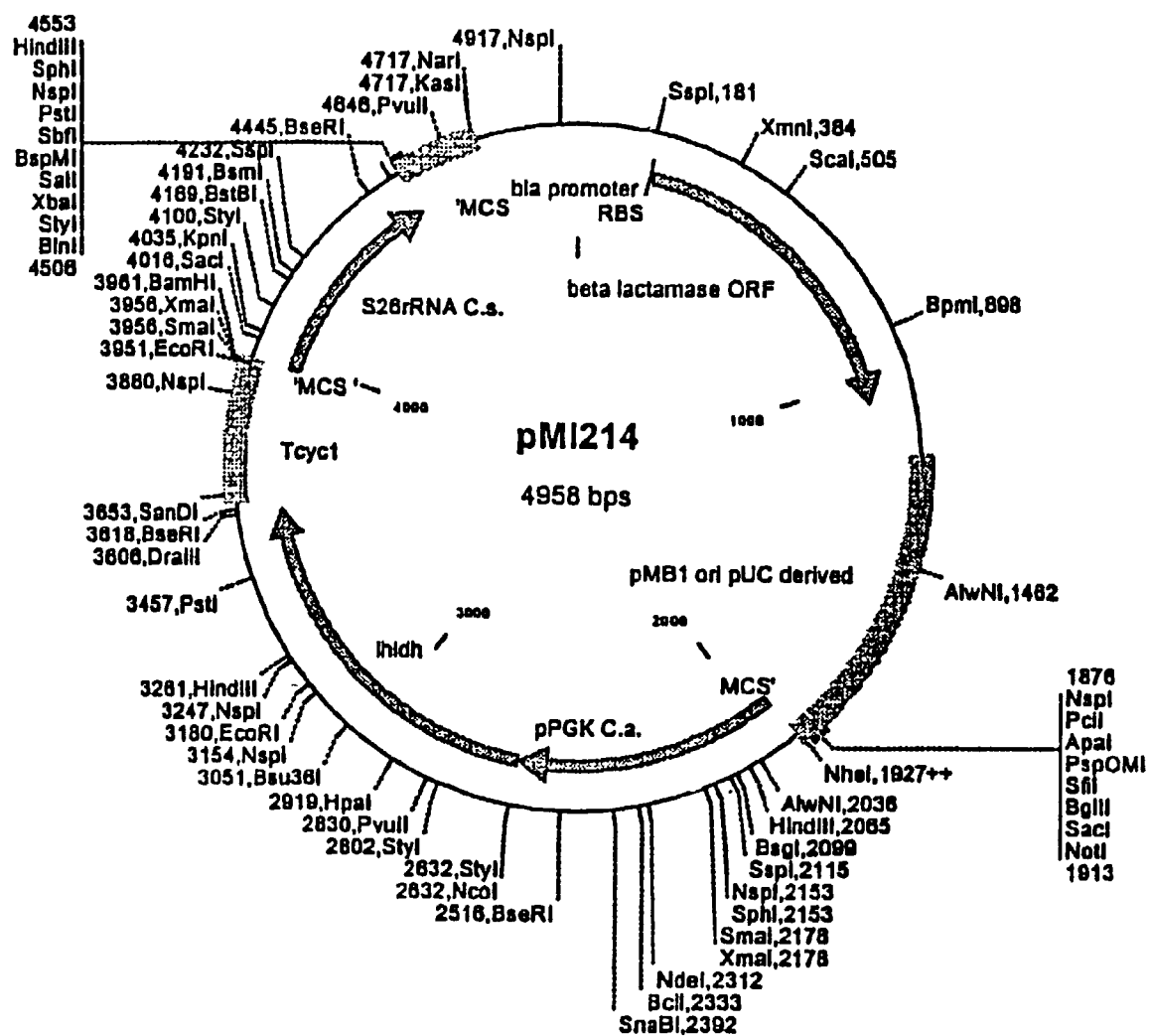
Figure 23A:
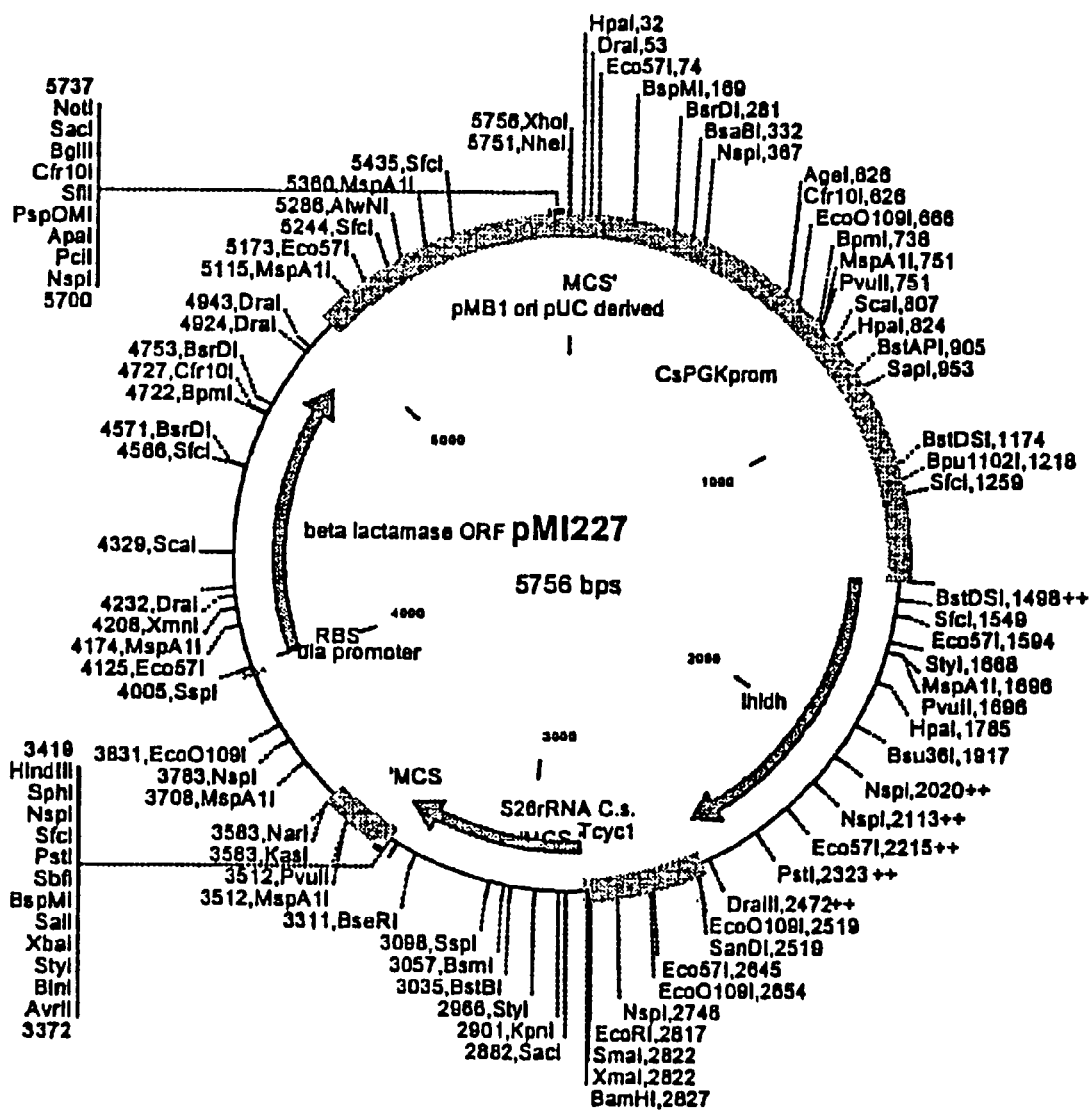
Figure 23A:
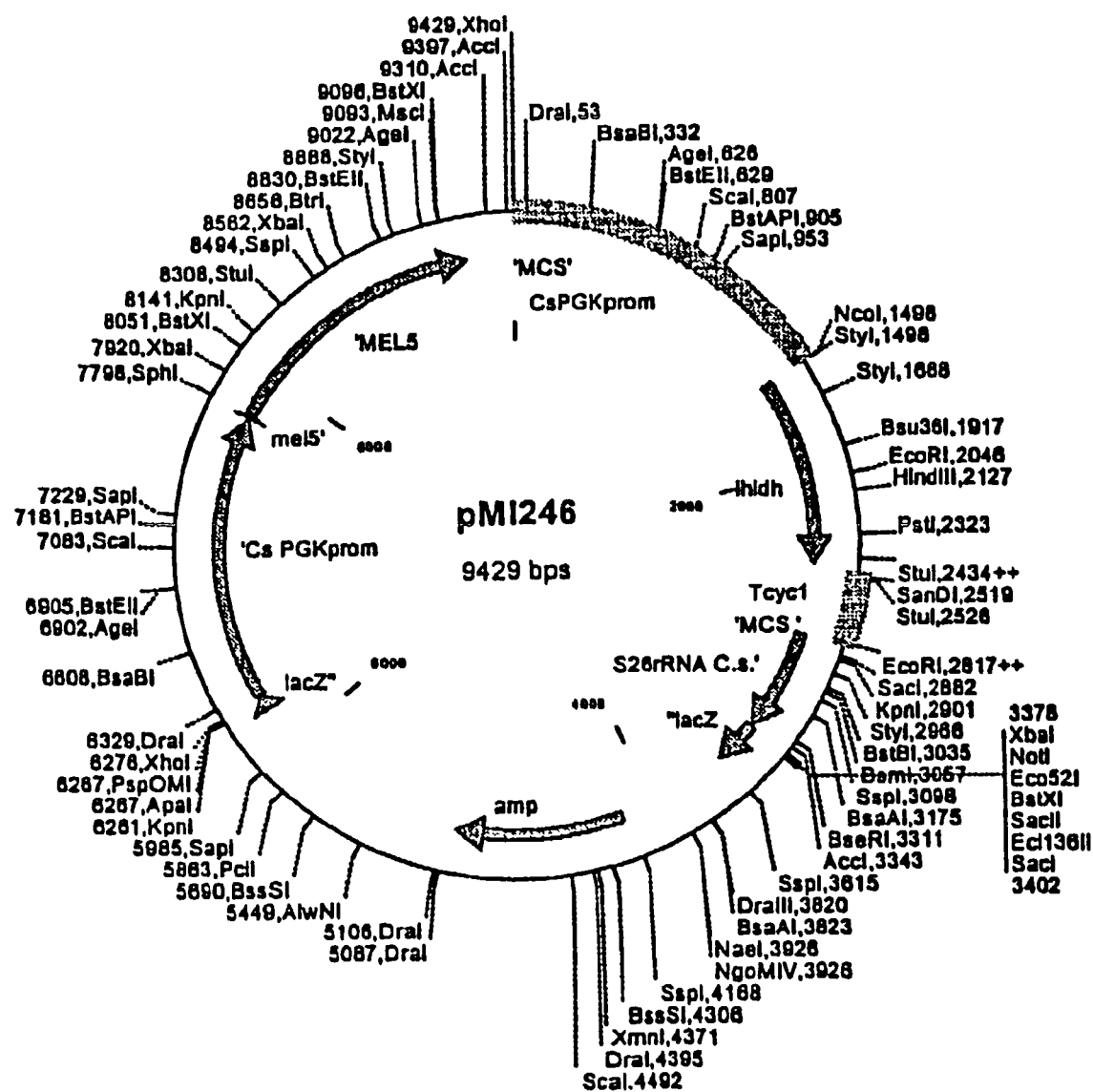
Figure 23A:
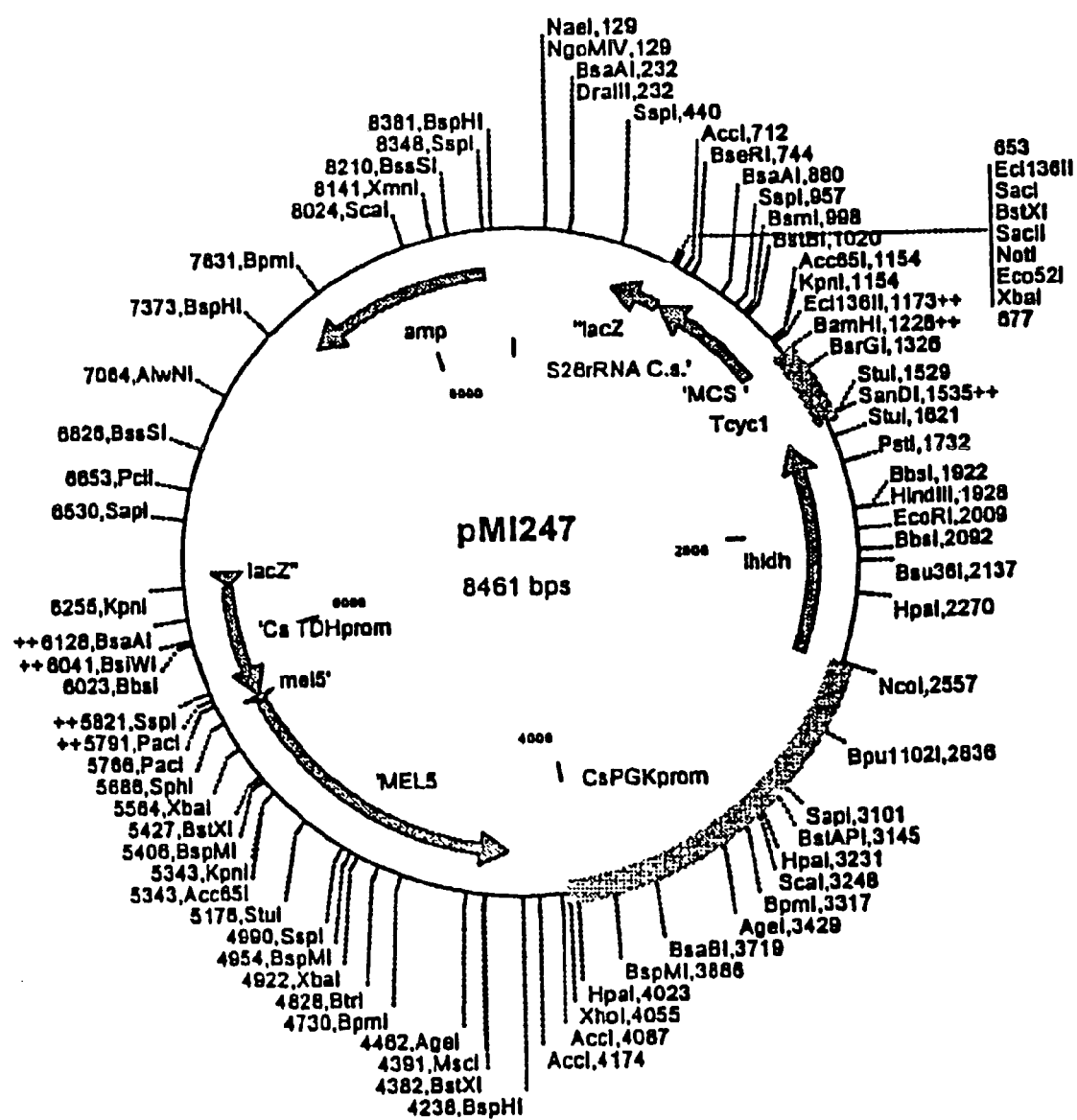

As used herein, "organic product" is any compound containing a carbon atom. Non-limiting examples of organic products include carboxylates (e.g. lactate, acrylate, citrate, isocitrate, alpha-ketoglutarate, succinate, fumarate, malate, oxaloacetate), carbohydrates (e.g. D-xylose), alditols (e.g. xylitol, arabitol, ribitol), amino acids (e.g. glycine, tryptophan, glutamate), lipids, esters, vitamins (e.g., L-ascorbate), polyols (e.g. glycerol, 1,3-propanediol, erythritol), aldehydes, alkenes, alkynes, and lactones. Thus, an organic product can contain one, two, three, four, five, six, seven, eight, nine, ten, or more carbon atoms. In addition, organic products can have a molecular weight that is less than about 1,000 (e.g. less than about 900, 800, 700, 600, 500, 400, 300, 200, or 100) daltons. For example, D-xylose ($C_5H_{10}O_5$) is an organic product that has a molecular weight of 150 daltons. Further, organic products can be fermentation products.

The term "fermentation product" as used herein refers to any organic compound that is produced by a fermentation process. Generally, a fermentation process can involve the anaerobic enzymatic conversion of organic compounds (e.g. carbohydrates) to compounds such as ethyl alcohol, producing energy in the form of ATP. Cellular fermentation differs from cellular respiration in that organic products rather than molecular oxygen are used as electron acceptors. Non-limiting examples of fermentation products are acetate, ethanol, butyrate, and lactate.

The organic products can also be derived from pyruvate. A "pyruvate-derived product," as used herein, refers to any compound that is synthesized from pyruvate within no more than fifteen enzymatic steps. One enzymatic step is considered to be any chemical reaction or series of reactions catalyzed by a polypeptide having enzymatic activity. Such polypeptides are any polypeptide that catalyzes a chemical reaction of other substances without itself being destroyed or altered upon completion of the reaction or reactions. These polypeptides can have any type of enzymatic activity including the non-limiting examples of activities associated with aconitase, isocitrate dehydrogenase, ketoglutarate dehydrogenase, succinate thiokinase, succinate dehydrogenase, fumarase, malate dehydrogenase, citrate synthase, 2,5-dioxovalerate dehydrogenase, 5-dehydro-4-deoxy-D-glucarate dehydrogenase, glucarate dehydratase, aldehyde dehydrogenase, glucuronolactone reductase, L-gulonolactone oxidase, 2-dehydro-3-deoxy-D-pentanoate aldolase, xylonate dehydratase, xylonolactonase, D-xylose dehydrogenase, lactate dehydrogenase, CoA-transferase, lacyl-CoA dehydratase, or acrylyl-CoA hydratase.

The carboxylate products of the invention can be in the free acid or salt form, and can be referred to interchangeably (e.g. "lactic acid" or "lactate"). Use of either of the terms is taken to encompass the other, unless specifically noted otherwise. In preferred embodiments, the invention provides the carboxylates in free acid form.

The term "nucleic acid sequence" or "nucleic acid molecule" refers to a DNA or RNA molecule. The term encompasses molecules formed from any of the known base analogs of DNA and RNA such as, but not limited to, 4-acetylcytosine, 8-hydroxy-N-6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5' methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "vector" is used to refer to any molecule (e.g., nucleic acid, plasmid, or virus) used to transfer protein-coding information to a host cell.

The term "expression vector" refers to a vector that is suitable for transformation of a host cell and contains nucleic acid sequences that direct and/or control expression of inserted heterologous nucleic acid sequences. Expression includes, but is not limited to, processes such as transcription, translation, and RNA splicing, if introns are present.

The term "operably linked" is used herein to refer to an arrangement of sequences wherein the sequences are joined together and configured or assembled so as to perform their usual function. Thus, a sequence operably linked to a sequence encoding a protein may flank the coding sequence and be capable of effecting replication and/or transcription of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "host cell" is used to refer to a cell into which has been introduced or transformed, or is capable of being transformed with a nucleic acid sequence and then of expressing a selected gene of interest. The term includes the progeny of the parent cell, whether or not the progeny is identical in morphology or in genetic make-up to the original parent.

The term "endogenous" as used herein refers to genomic material that is not exogenous, that is, which has not been introduced into the cell. Such endogenous genomic material usually develops within an organism, tissue, or cell and is not inserted or modified by recombinant technology. Endogenous genomic material encompasses naturally occurring variations.

The term "exogenous" or "heterologous" as used herein refers to genomic material that is not endogenous, that is, material that has been introduced into the cell. Typically such material is inserted or modified by recombinant technology.

As used herein, the term "genetically modified" refers to an organism whose genome has been modified by methods including the non-limiting examples of addition, substitution, or deletion of genetic material. Such methods of genetic manipulation are well known in the art and include, but are not limited to, random mutagenesis, point mutations, including insertions, deletions, and substitutions of one or a plurality of individual nucleotide residues, knock-out technology, and transformation of an organism with a nucleic acid sequence using recombinant technology, including both stable and transient transformants.

The terms "anaerobic" and "anaerobic conditions" are taken to mean that the amount of dissolved oxygen in a solution, typically a culture medium, is not detectable (i.e., about 0%), or alternatively the amount of oxygen in the atmosphere is from about 0% to 2%.

Vectors and Host Cells

A nucleic acid molecule encoding the amino acid sequence of a polypeptide useful for synthesis of organic products of interest is inserted into an appropriate cloning or expression vector using standard ligation techniques (see, for example, Sambrook et al., 2001, MOLECULAR CLONING: A LABORATORY MANUAL, 3$^{rd}$ ed., Cold Spring Harbor Laboratory Press, New York). The vector is typically selected to be functional in the particular host cell employed (i.e., the vector is compatible with the host cell machinery such that replication, amplification and/or expression of the gene can occur). A nucleic acid molecule encoding the amino acid sequence of a polypeptide useful for synthesis of organic products of interest can be amplified in any appropriate cell and expressed in any host cell, most preferably a Crabtree-negative host cell.

Preferred Crabtree-negative host cells include those from genera *Candida,* including the non-limiting examples of *C. sonorensis, C. methanosorbosa, C. diddensiae, C. parapsilosis, C. naeodendra, C. krusei, C. blankii* and *C. entomophila.*

Flanking sequences (including promoters and terminators) may be homologous (i.e., from the same species and/or strain as the host cell), heterologous (i.e., from a species other than the host cell species or strain), hybrid (i.e., a combination of flanking sequences from more than one source), or synthetic, or the flanking sequences may be native sequences that normally function to regulate expression of the gene of interest. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from a biological source using the appropriate restriction endonucleases. In some cases, the complete nucleotide sequence of a flanking sequence may be known. In such cases, the flanking sequence may be synthesized using methods well known to those of skill in the art, as well as those described herein, for nucleic acid synthesis or cloning.

Where all or only a portion of the flanking sequence is known, the full extent of the functional flanking sequence may be obtained using in vitro amplification technique such as polymerase chain reaction (PCR) and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

A selectable marker gene or element encodes a protein necessary for survival and growth of a host cell grown in a selective culture medium. Useful selection marker genes encode proteins that (a) confer resistance in host cells to antibiotics or other toxins, e.g., ampicillin, tetracycline, or kanamycin; (b) complement auxotrophic deficiencies of the host cell, such as Leu2 deficiency, or (c) supply critical nutrients not available from complex media. Preferred selectable markers include the non-limiting examples of zeocin resistance gene, G418 resistance gene, and the hygromycin resistance gene.

Other selection genes may be used to amplify the gene that will be expressed. Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and promoterless thymidine kinase. The mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is progressively increased, thereby leading to the amplification of both the selection gene and DNA that encodes a polypeptide useful for synthesizing an organic product.

Expression and cloning vectors of the present invention will typically contain a promoter that is recognized by the host organism and operably linked to the molecule encoding the polypeptide useful for synthesizing an organic product. Promoters are untranscribed sequences located upstream (i.e., 5') to the translation start codon of a structural gene (generally within about 100 to 1000 bp) and control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no regulation of gene expression. A large number of promoters of both promoter types, recognized by a variety of potential host cells, are well known in the art. A suitable promoter is operably linked to DNA encoding a polypeptide useful for synthesizing an organic product by removing the promoter from the source DNA by restriction enzyme digestion or producing a promoter fragment by in vitro amplification and inserting the desired promoter sequence into the vector. Native promoter sequences may be used to direct amplification and/or expression of a nucleic acid molecule that encodes a polypeptide useful for synthesizing an organic product. A heterologous promoter is preferred, however, if it permits greater transcription and higher yields of the expressed protein compared to the native promoter, and if it is compatible with the host cell system that has been selected for use.

Suitable promoters for use with yeast host cells are also well known in the art, and include the non-limiting examples of promoters from yeast genes including phosphoglycerate kinase (PGK), triose dehydrogenase (TDH), pyruvate decarboxylase (PDC), triose phosphate isomerase (TPI), and alcohol dehydrogenase (ADH). Preferred promoters of the invention include PGK and TDH promoters. Yeast enhancers, sequences that increase expression when placed in relative proximity to a promoter are advantageously used with yeast promoters.

Methods of transforming cells are well known in the art, and can include such non-limiting examples as electroporation and calcium chloride or lithium acetate based transformation methods.

Several of the vectors disclosed in the Examples of this invention have been previously constructed and are described in application PCT/US01/44041. Briefly vectors pMI234, pMI238, pMI246, pMI247, and the PDC2 in lambda were constructed as follows.

*C. sonorensis* gene isolation (PDC2 in lambda): Genomic DNA of *C. sonorensis* (ATCC Accession No. 32109) was isolated from cells grown overnight in YPD using the Easy DNA kit (Invitrogen). DNA was partially digested with Sau3A and size fractionated by sucrose gradient centrifugation (Sambrook et al. Id.,). DNA fragments of about 22 kb were ligated to BamHI digested, phosphatase treated lambda DASH™ vector arms (Stratagene) and the ligation mixture was packaged into lambda particles using Gigapack II Gold Packaging Extract (Stratagene). The lambda particles were used to infect *E. coli* MRA P2.

Probes used for isolation of *C. sonorensis* genes from the library were prepared by PCR amplification using the Dynazyme EXT polymerase (Finnzymes, Espoo, Finland), sequence specific primers and genomic DNA of *S. cerevisiae*, *C. albicans* or *C. sonorensis* as a template as follows. Oligonucleotides TGT CAT CAC TGC TCC ATC TT (SEQ ID No.17) and TTA AGC CTT GGC AAC ATA TT (SEQ ID No. 18) corresponding to the *S. cerevisiae* TDH1 gene were used to amplify a fragment of the TDH gene from genomic *S. cerevisiae* DNA.

Oligonucleotides GCG A<u>CTCGAG</u> G TCC TAG AAT ATG TAT ACT AAT TTG C (SEQ ID No. 19) and CGC GAA TTC <u>CCATGG</u> TTA GTT TTT GTT GGA AAG AGC AAC (SEQ ID No. 20) corresponding to the *C. albicans* PGK1 gene were used to amplify a fragment of the PGK1 gene from genomic *C. albicans* DNA.

Oligonucleotides TGG <u>ACTAGT</u> AAA CCA ACA GGG ATT GCC TTA GT (SEQ ID No. 21) and CTA G <u>TCTAGA</u> GA TCA TTA CGC CAG CAT CCT AGG (SEQ ID No. 22) corresponding to the *C. sonorensis* 26 S rRNA were used to amplify a fragment of the 26S rDNA gene from *C. sonorensis* genomic DNA.

Oligonucleotides CCG <u>GAATTCGATATC</u> TGG GCW GGK AAT GCC AAY GAR TTR AAT GC (SEQ ID No. 23) and CGC <u>GGATTCAGGCCT</u> CAG TAN GAR AAW GAA CCN GTR TTR AAR TC (SEQ ID No. 24) were designed based on portions of pyruvate decarboxylase amino acid sequence WAGNANELNA (SEQ ID No. 25) and DFNTGSFSYS (SEQ ID No. 26), that are conserved between *S. cerevisiae* PDC1, *Pichia stipitis* PDC1 and PDC2, and incomplete sequences of *Candida albicans* PDC1 and PDC3. These primers were used were used to amplify a fragment of the PDC gene(s) from *C. sonorensis* genomic DNA. PCR reaction with these primers produced two fragments of different nucleotide sequence termed PDC1 and PDC2.

Oligonucleotides TCTGTTMCCTACRTAAGA (SEQ ID No. 27) and GTYGGTGGTCACGAAGGTGC (SEQ ID No. 28) were designed based on conserved regions found in fungal alcohol dehydrogenase sequences. These primers were used to amplify a fragment of the ADH gene(s) from *C. sonorensis* genomic DNA. PCR reaction with these primers produced three fragments of different nucleotide sequences termed ADH1, ADH2, and ADH3.

The library was screened with PCR fragments produced as described above, and products were labeled with $^{32}P$ α-dCTP using the Random Primed Labeling Kit (Boehringer Mamiheim). Hybridization with the radioactive probes was performed by incubation overnight at 42° C. in a solution containing 50% formamide, 5× Denhardt's, 5×SSPE, 0.1% SDS, 100 µg/mL herring sperm DNA, 1 µg/mL polyA DNA. For TDH1, PGK1, and PDC1 probes, filters were washed after hybridization at room temperature in a solution of 2×SSC for 5 min and repeated, followed by two 30 min washes in a solution of 1×SSC—0.1% SDS at 68° C. The post hybridization washes for rDNA and PDC2 probes were performed twice for 5 min at room temperature in 2×SSC, followed by two 30 min. washes in 0.1×SSC –0.1% SDS at 68° C.

Positive plaques were isolated and purified according to manufacturers instructions (Stratagene). Bacteriophage were purified using conventional methods (Sambrook et al., Id.), modified by eliminating DNAseI treatment and precipitating phage particles released from lysed host cells using PEG6000. Said phage particles were then dissolved in SM buffer and extracted with chloroform, pelleted by centrifugation at 25,000 rpm in Kontron TST41.14 rotor for 2 h, and again dissolved in SM buffer. Lambda DNA was isolated by digesting the phage particles with proteinase K followed by phenol extraction and ethanol precipitation.

*C. sonorensis* genomic DNA inserts were partially sequenced using sequence-specific primers. The nucleotide sequences and the amino acid sequences deduced therefrom were compared against sequence databases in order to identify genes encoded in whole or part by the phage insert, using homology to known genes or proteins. The sequences obtained had significant similarity to fungal rDNA, phosphoglycerate kinases, glyceraldehyde-3-phosphate dehydrogenases, or pyruvate decarboxylases depending on the probe used for isolating each clone. The start and end points of the open reading frames encoding sequences of *C. sonorensis* PGK1, PDC1 and TDH1 were identified thereby.

"Building-block" vectors, pMI203, pMI205 (Zeocin resistance vectors for *C. sonorensis*), pVR24, and pVR27

These plasmids are used in the construction of the vectors described in the Examples and are described in PCT application PCT/US01/44041. Briefly, the construction of these vectors is described.

The plasmid pTEF1/Zeo (Invitrogen) containing the zeocin resistance marker under control of *S. cerevisiae* TEF1 promoter was modified by adding a *C. sonorensis* rDNA fragment to provide a target for homologous recombination. The following oligonucleotide primers:

(SEQ ID No. 29)
TGG <u>ACT AGT</u> AAA CCA ACA GGG ATT GCC TTA GT
and (SEQ ID No. 30)
CTA G<u>TC TAG A</u>GA TCA TTA CGC CAG CAT CCT AGG, which correspond to *C. sonorensis* 26 S rRNA (Genbank Accession No. U70185), were used to amplify *C. sonorensis* genomic DNA to provide a PCR-amplified fragment of the 26S rDNA gene. The resulting PCR product fragment was digested with restriction enzymes SpeI and XbaI and ligated with pTEF/Zseo plasmid digested with XbaI. The resulting plasmid was designated pMI203 (FIG. 23B).

Figure 23B:
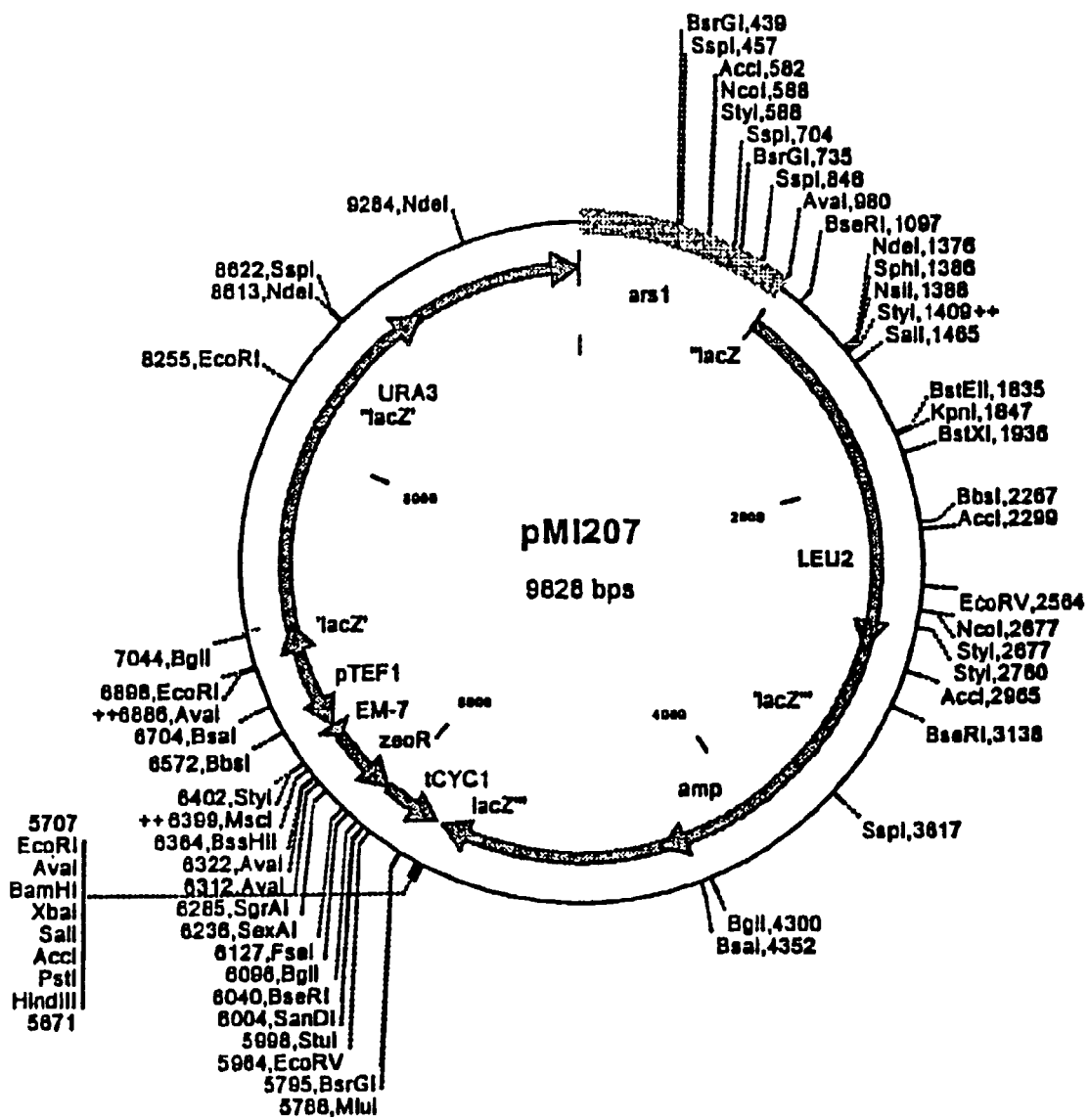
Figure 23B:
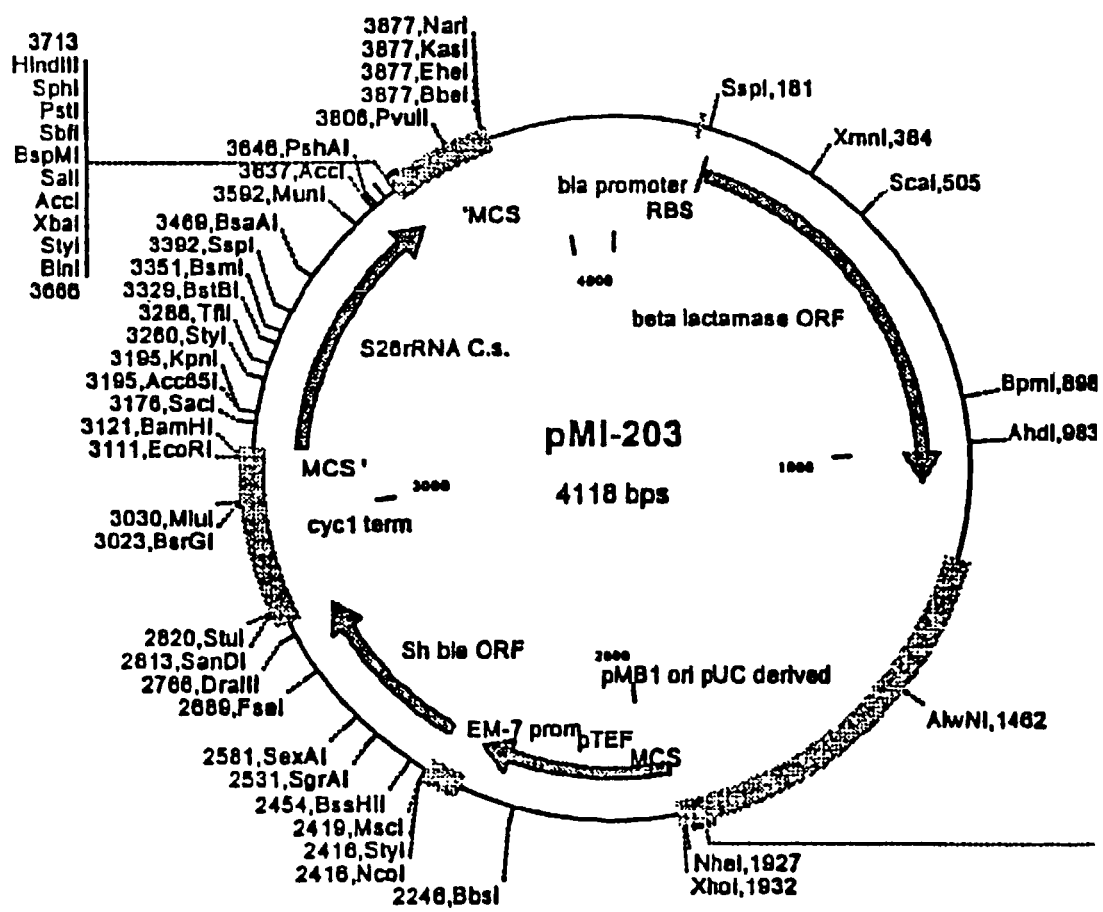
Figure 23B:
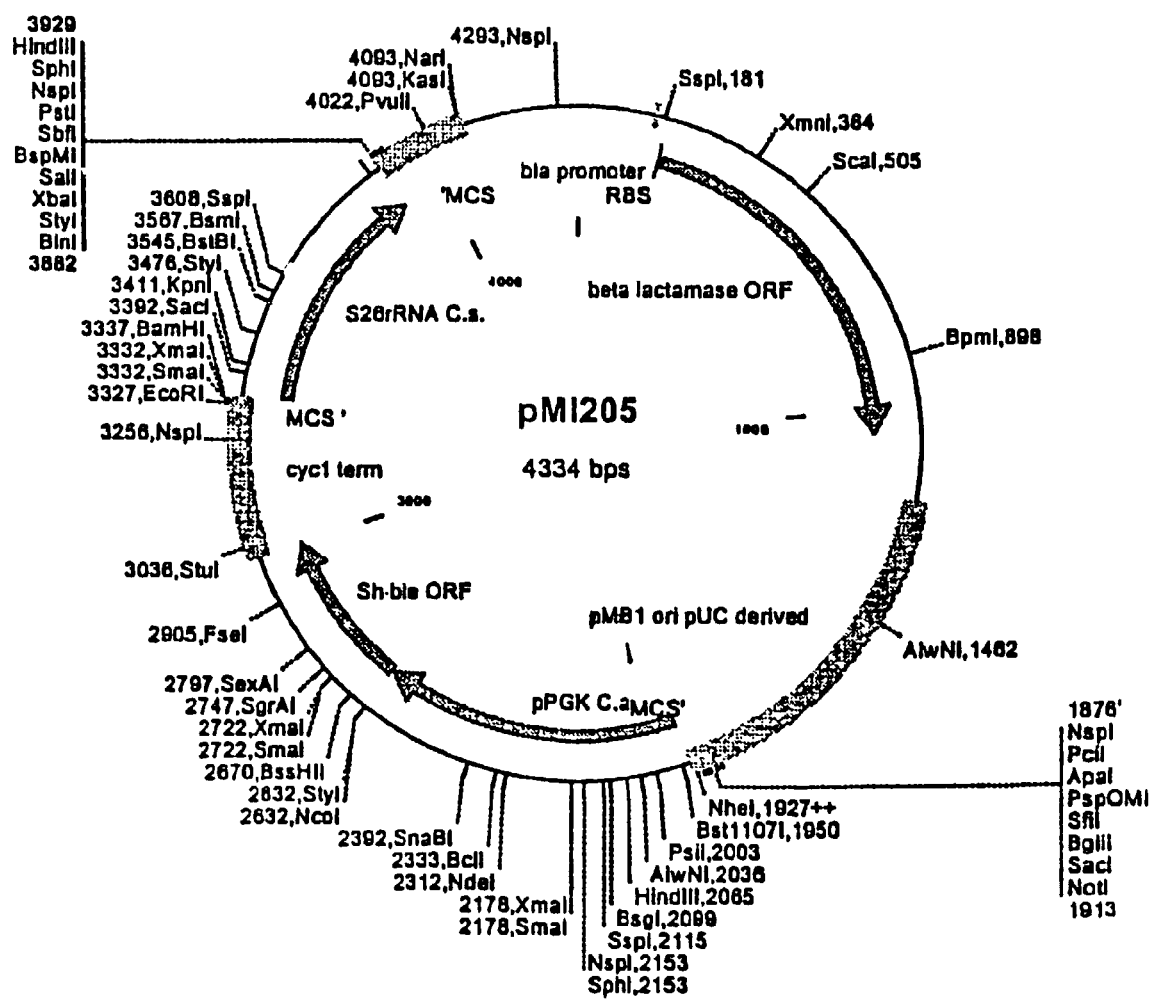

The TEF1 promoter contained in pMI203 was replaced by a promoter of a gene from another *Candida* species, the *C. albicans* PGK1 promoter. The following oligonucleotide primers:

```
                                       (SEQ ID No. 31)
GCG ATC TCG AGG TCC TAG AAT ATG TAT ACT AATTTGC
and (SEQ ID No. 32)
ACT TGG CCA TGG TGA TAG TTA TTC TTC TGC AATTGA
``` were designed based on the available *C. albicans* PGK1 sequence (Genbank Accession No. U25180). These primers were used to amplify a 700 bp fragment from the region upstream of the *C. albicans* PGK1 open reading frame, using *C. albicans* genomic DNA as the template. Restriction sites XbaI and SpeI (underlined above) were added to the primers to facilitate cloning of the fragment. After amplification, the fragment was isolated and digested with restriction enzymes XhoI and NcoI and then ligated to plasmid pMI203 digested with XhoI and NcoI. The resulting plasmid was designated pMI205 (FIG. 23B).

PVR24 and pVR27: Plasmid pBFY004 (proprietary, NREL) was digested with NotI restriction enzyme (Invitrogen), resulting in a 1235bp fragment (SEQ ID No: 33). The fragment was isolated and ligated to a NotI digested pGEM5zF(+) (Promega North, Madison, Wis.). *E. coli* (top10) (Invitrogen) was transformed with the ligation mixture using standard electroporation protocols (Sambrook, Id.). The resultant plasmid was designated pNC002.

*B. megaterinum* DNA encoding the LDH gene was isolated as follows. *B. megaterium* was obtained from the American Type Culture Collection (ATCC Accession #6458) and grown under standard conditions. Genomic DNA was purified from these cells using an Invitrogen "Easy-DNA" kit according to the manufacturer's protocol. Primers were designed on the basis of the available sequence in Genbank for the L-LDH from *B. megaterium* (Genbank accession # M22305). PCR amplification reactions were performed using standard techniques, with each reaction containing *B. megaterium* genomic DNA (6 ng/gL), the 4 dNTPs (0.2 mM), and the amplification primers BM1270 and BM179 (1 µM in each). The primers have the sequences:

```
BM1270   CCTGAGTCCACGTCATTATTC   (SEQ ID No: 34)
and

BM179    TGAAGCTATTTATTCTTGTTAC  (SEQ ID No: 35)
```

Reactions were performed according to the following themocycling conditions: an initial incubation for 10 min at 95° C., followed by 35 cycles consisting of 30 sec at 95° C., 30 sec. at 50° C., 60 sec at 72° C. A strong product fragment of 1100 base pairs (bp) was gel purified using conventional procedures, cloned, and sequenced. The resulting sequence could be translated into a polypeptide that exhibited excellent homology to known L-LDH-encoding genes.

The coding sequence for the *B. megaterium* LDH-encoding disclosed herein was operatively linked to a promoter from the PGK1 gene and a transcriptional terminator from the GAL10 gene, both from the yeast *Saccharomyces cerevisiae*. Two oligonucleotide primers, Bmeg5' and Bmeg3', were designed based on this sequence to introduce restriction sites at the ends of the coding sequence of the gene:

```
Bmeg5'
GCTCTAGATGAAAACACAATTTACACC   (SEQ ID No: 36)
and

Bmeg3'
ATGGATCCTTACACAAAAGCTCTGTCGC (SEQ ID No: 37)
```

This amplification reaction was performed using dNTP and primer concentrations described above using Pfu Turbo polymerase (Stratagene) in a buffer supplied by the manufacturer. Thermocycling was done by initially incubating the reaction mixture for 3 min at 95° C., then by 20 cycles of 30 sec at 95° C., 30 sec at 50° C., 60 sec at 72° C., followed by a final incubation for 9 min at 72° C. The product was digested with restriction enzymes XbaI and BamHI and then ligated into the XbaI and BamHI sites of plasmid pNC002. This ligation resulted in the PGK promoter and GAL10 terminator becoming operably linked to the *B. megaterium* LDH coding sequence (pVR24; FIG. 21).

Construction of pVR27 (FIG. 22) was performed to create a vector containing *R. oryzae* LDH for its expression under the control of the *S. cerevisiae* PGK1 promoter. LDH was isolated from Rhizopus oryzae from genomic DNA purified ("Easy-DNA" kit, Invitrogen) from cells (ATCC Accession #9363) grown under standard conditions. Primers were designed on the basis of the available sequence in Genbank for the LDH from *R. oryzae* (Genbank accession # AF226154). PCR amplification reactions were performed using standard techniques, with each reaction containing *R. oryzae* genomic DNA (6 ng/µL), each of 4 dNTPs (0.2 mM), and each of the amplification primers Ral-5' and Ral-3' (1 µM). The amplification primers had the sequence:

```
Ral-5'   CTTTATTTTTCTTTACAATATAATTC (SEQ ID No:38)
and

Ral-3'   ACTAGCAGTGCAAAACATG        (SEQ ID No:39)
```

Reactions were performed according to the following cycling conditions: an initial incubation for 10 min at 95° C., followed by 35 cycles consisting of 30 sec at 95° C., 30 sec. at 41° C., 60 sec at 72° C. A strong product fragment of 1100 bp was gel purified, cloned in TA vector (Invitrogen, Carlsbad, Calif.) and sequenced. The resulting sequence could be translated into a polypeptide that exhibited excellent homology to known *Rhizopus oryzae* LDH-encoding gene sequence in Genbank (Accession # AF226154).

The coding sequence for the *R. oryzae* LDH-encoding gene disclosed herein was operatively linked to a promoter from the PGK1 and a transcriptional terminator from the GAL10 gene, both from the yeast *S. cervisiae*. In making this construct, the following oligonucleotides were prepared and used to amplify the coding sequence from the plasmid containing the *Rhizopus* LDH insert. Two oligonucleotide primers, Rapgk5 and Papgk3', were designed based on this sequence to introduce restriction sites at the ends of the coding sequence of the gene.

```
Rapgk5
GCTCTAGATGGTATTACACTCAAAGGTCG    (SEQ ID No: 40)
and

Papgk3
GCTCTAGATCAACAGCTACTTTTAGAAAAG  (SEQ ID No: 41)
```

This amplification reaction was performed using dNTP and primer concentrations as described above using Pfu Turbo polymerase (Stratagene) in a buffer supplied by the manufacturer. Thermocycling was done by initially incubating the reaction mixture for 3 min at 95° C., then by 20 cycles of 30 sec at 95° C., 30 sec at 53° C., 60 digested with restriction enzymes XbaI and then ligated into the XbaI site of plasmid pNC002.

Figure 23C:
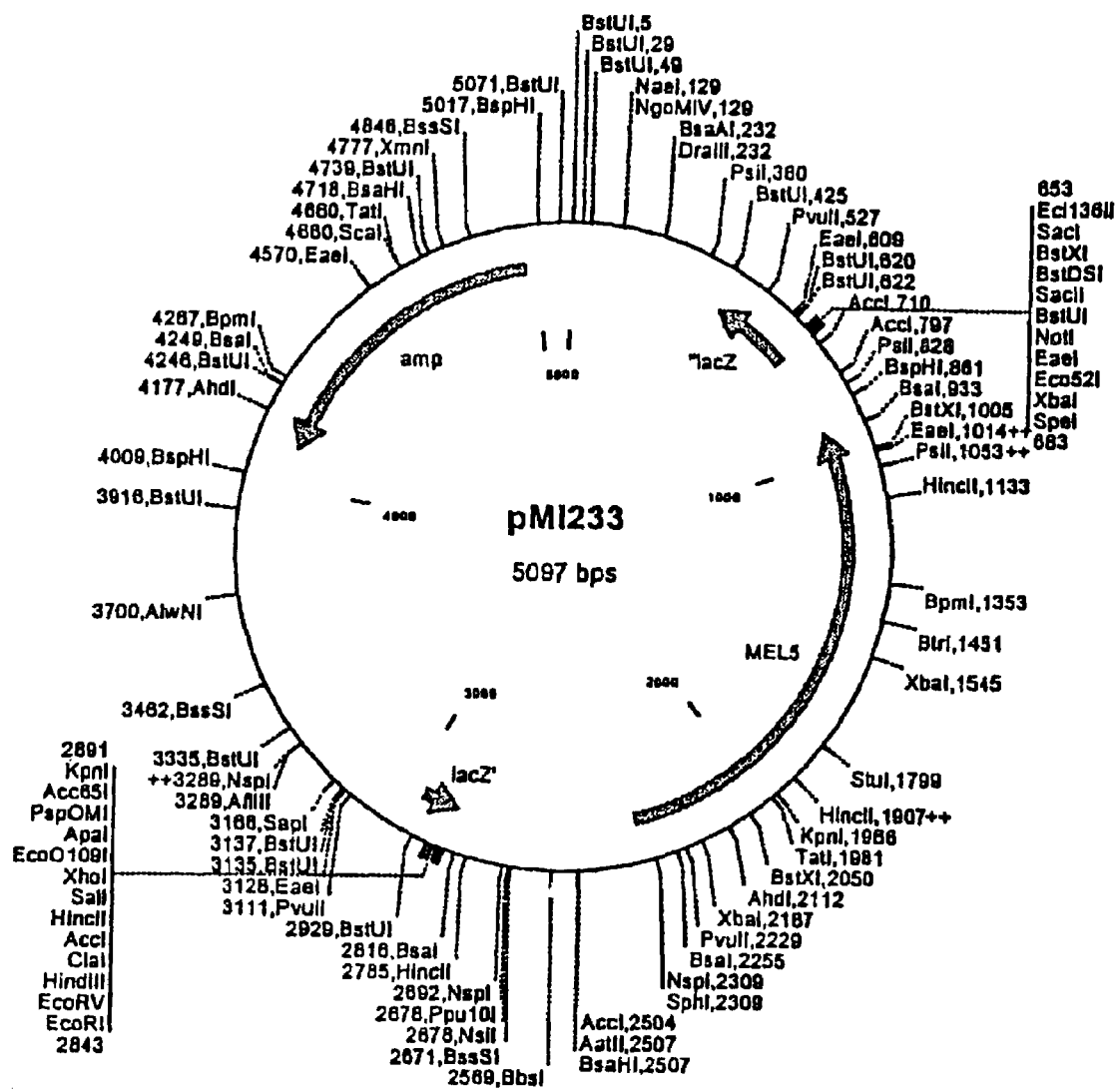
Figure 23E:
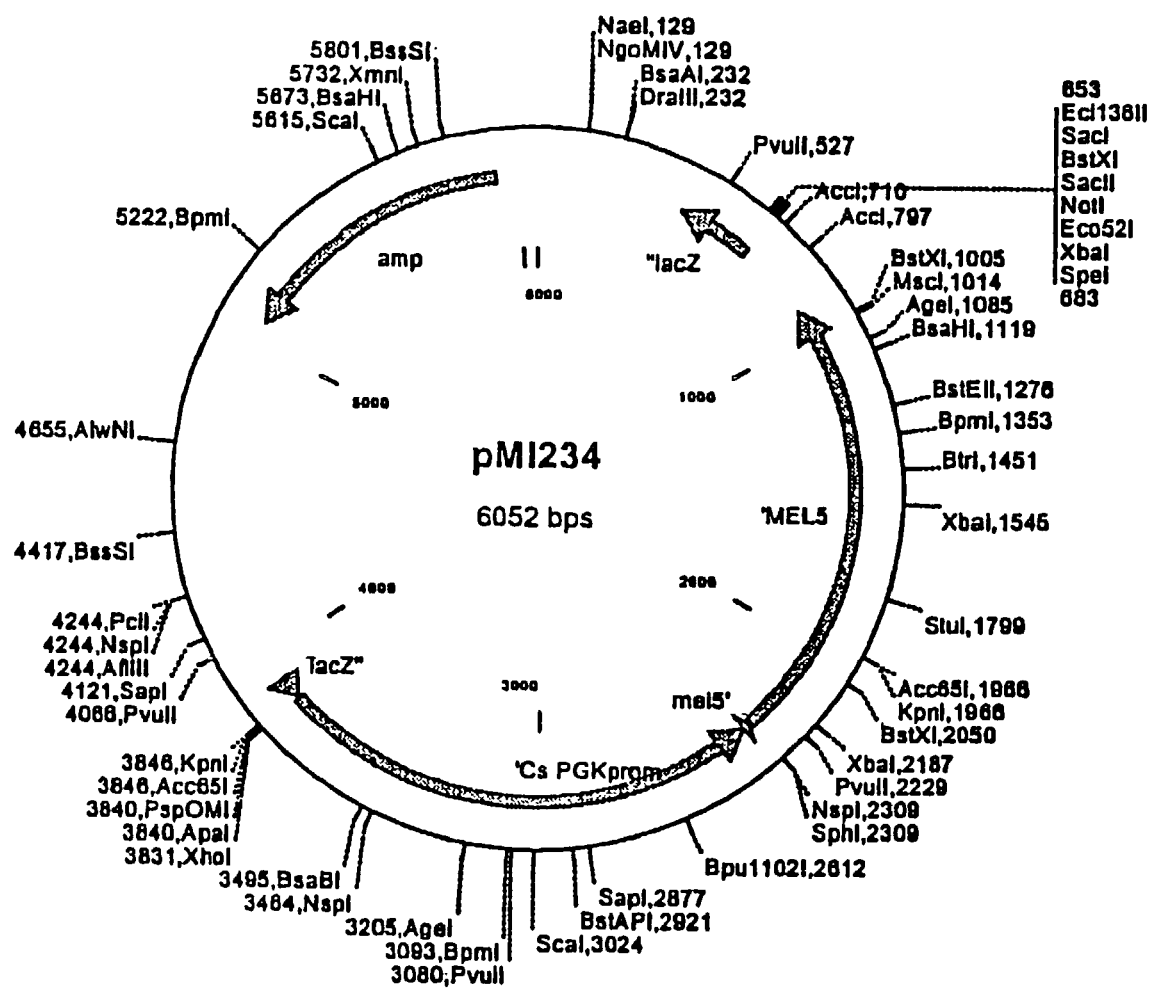
Figure 23C:
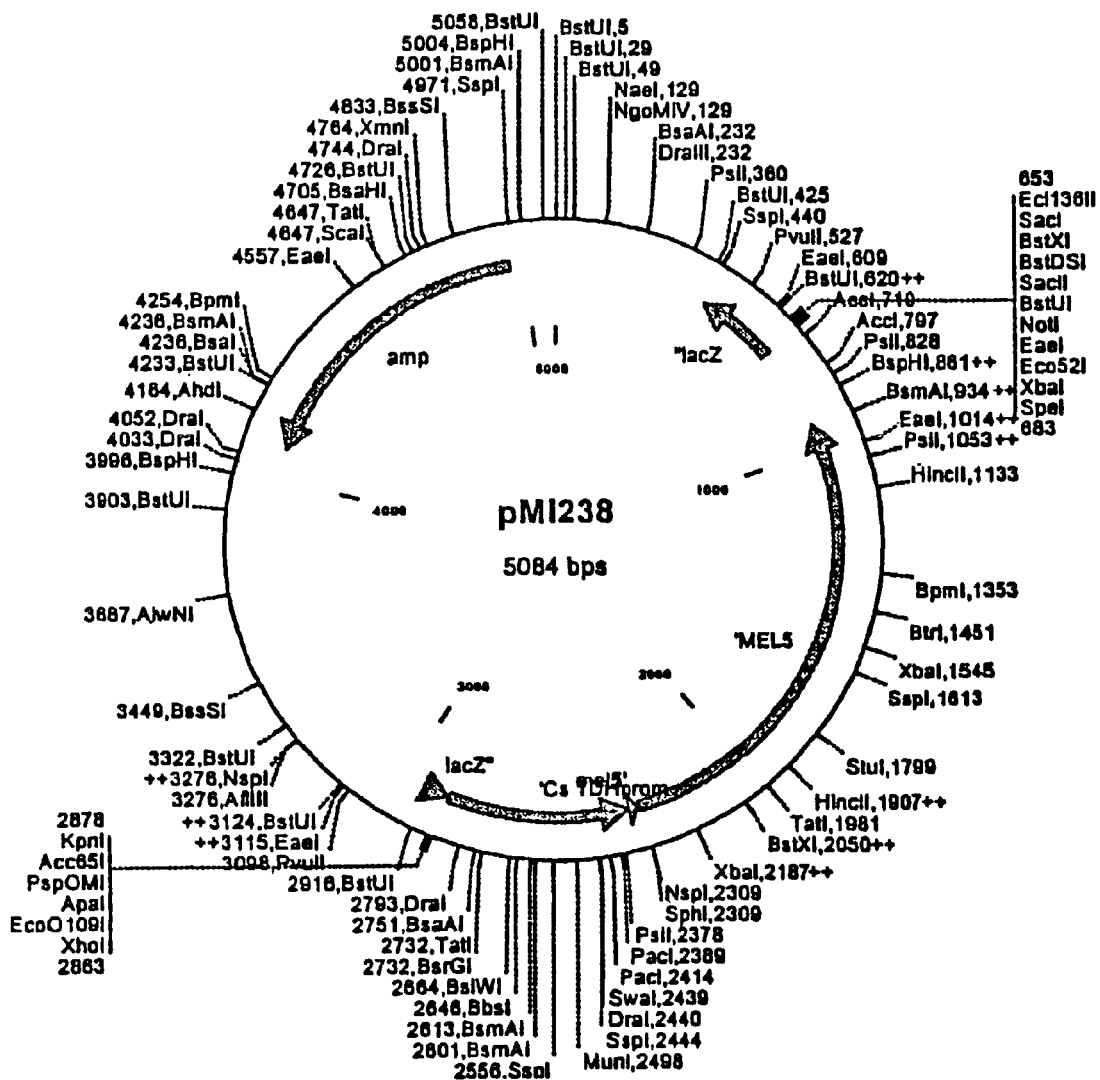

This ligation resulted in the PGK promoter and GAL10 terminator becoming operably linked to the *R. oryzae* LDH coding sequence (pVR27; FIG. 22)

pMI234 and pMI238: In order to develop a positive selection for *C. sonorensis* transformants, the *S. cerevisiae* MEL5 gene (Naumov et al., 1990, MGG 224: 119–128; Turakainen et al., 1994, *Yeast* 10: 1559–1568; Genbank Accession No. Z37511) was obtained as the 2160 bp EcoRI-SpeI fragment from plasmid pMEL5-39 and ligated to pBluescript II KS(−) (Stratagene) digested with EcoRI and SpeI. The EcoRI site in the MEL5 gene is located 510 bp upstream of the initiator ATG, and the SpeI site is located 250 bp downstream of the stop codon of MEL5. The resulting plasmid was designated pMI233 (FIG. 23C).

The 1500 bp PGK1 promoter of *C. sonorensis* was amplified with primers having the sequence: GCG AT CTCGAGA AAG AAA CGA CCC ATC CAA GTG ATG (SEQ ID No. 5) and TGG ACTAGT ACA TGCATGCGG TGA GAA AGT AGA AAG CAA ACA TTG TAT ATA GTC TTT TCT ATT ATT AG (SEQ ID No. 42) using DNA from the PGK1 lambda clone isolated above as template. The 3' primer can create a fusion between the *C. sonorensis* PGK1 promoter and *S. cerevisiae* MEL5, since it corresponds to nucleotides present in the PGK1 promoter immediately upstream of the open reading frame and nucleotides corresponding to the 5' end of MEL5 open reading frame. The resulting amplified fragment was digested with restriction enzymes SphI and XhoI and ligated to plasmid pMI233 (FIG. 23C) digested with SphI and XhoI. The resulting construct in the plasmid contains *C. sonorensis* PGK1 promoter upstream of and operatively linked to the MEL5 open reading frame, and is identified as pMI234 in FIG. 5.

In a similar fashion, a 650 bp of the *C. sonorensis* TDH1 promoter was amplified with primers having the sequence: GCG ATCTCGAGA AAA TGT TAT TAT TAT AAC ACT ACA C (SEQ ID No. 3) and TGG ACTAGT ACA TGCATGCGG TGA GAA AGT AGA AAG CAA ACA TTT TGT TTG ATT TGT TTG TTT TGT TTT TGT TTG (SEQ ID No. 43) using DNA from the TDH1 lambda clone isolated above as the template. The 3' primer can create a fusion between *C. sonorensis* TDH1 promoter and *S. cerevisiae* MEL5, since it corresponds to nucleotides present in the TDH1 promoter immediately upstream of the open reading frame and nucleotides corresponding to the 5' end of MEL5 open reading frame. The amplified fragment was digested with SphI and XhoI and ligated to plasmid pMI233 (FIG. 23C) digested with SphI and XhoI. The resulting plasmid, identified as pMI238 in FIG. 6, contains *C. sonorensis* TDH1 promoter upstream of and operatively linked to the MEL5 open reading frame.

pMI246 and pMI247: Plasmid pMI205 was used to produce a plasmid containing the MEL5 gene as a selectable marker and the LDH gene for enabling production of lactic acid in *C. sonorensis*. In the resulting plasmid, the zeocin resistance gene in pMI205 was replaced by the *L. helveticus* LDH gene.

A 1329 bp NcoI-BamHI fragment of pVR1 containing the LDH gene and the CYC1 terminator was ligated to the 3413 bp NcoI-BamHI fragment of pMI205 (FIG. 23B) bringing the *L. helveticus* LDH gene under control of the *C. albicans* PGK1 promoter; the resulting plasmid was named pM214. In a second step the *C. albicans* PGK1 promoter was replaced by the *C. sonorensis* PGK1 promoter. The *C. sonorensis* PGK1 promoter was isolated by amplification from an isolated lambda clone as described above using primers having the sequence: GCG ATCTCGAGA AAG AAA CGA CCC ATC CAA GTG ATG (SEQ ID No. 5) and ACT TGG CCATGG TAT ATA GTC TTT TCT ATT ATT AG (SEQ ID No. 44), and the PCR product was digested with XhoI and NcoI and ligated into pMI214 digested with XhoI and NcoI. This plasmid was designated pMI277 and is shown in FIG. 19.

The LDH expression cassette from pMI227 and MEL5 marker cassette from pMI234 were combined into the same vector by ligating a 3377 bp AvrII-NheI fragment of pMI227 (FIG. 23A) with SpeI-digested pMI234 (FIG. 23C). The resulting plasmid was designated pMI246 and is shown in FIG. 8.

The LDH expression cassette from pMI227 and the MEL5 marker cassette from pMI238 were combined into the same vector by ligating a 3377 bp AvrII-NheI fragment of pMI227 with SpeI-digested pMI238. The resulting plasmid was designated pM1247 and is shown in FIG. 9.

In one embodiment, the invention provides recombinant nucleic acid constructs comprising a nucleotide sequence that encodes a polypeptide useful for the biosynthesis of an organic product, which is operatively linked to a promoter that is functional in the genera *Candida*.

In related embodiments the nucleotide sequence encodes a lactate dehydrogenase gene. In preferred embodiments, the lactate dehydrogenase gene is heterologous to the *Candida* yeast cell into which it is introduced. In most preferred embodiments the lactate dehydrogenase gene is from a microorganism such as, for example, a bacterium or fungus, and the organic product produced according to the methods of the invention is lactic acid (or lactate).

Typically, the methods of the invention for producing lactic acid can yield (based on grams of lactic acid produced/gram of a carbohydrate substrate consumed) about 60% or more, preferably about 70% or more, more preferably about 80% or more, and most preferably about 90% or more, when the carbohydrate substrate is a hexose, for example, glucose.

The methods of the invention for producing lactic acid can result in lactic acid titers of about 75 grams/L or more, preferably about 90 grams/L or more, and most preferably about 100 grams/L or more. The cells of the invention have a specific productivity of lactic acid production (in terms of grams of lactic acid produced/gram of dry cell weight per hour) of about 0.20 or more, preferably about 0.30 or more, and most preferably about 0.50 or more, when a hexose carbohydrate substrate, such as glucose, is used for production.

In one embodiment, the Crabtree-negative cells of the invention can catabolize starch, either naturally or because of a genetic modification. In additional embodiments, the cells are genetically modified to catabolize cellulosics through the addition of such molecules as fungal-based cellulases.

In related embodiments, the cells of the invention can metabolize sugars other than glucose or other monosaccharide hexoses, in particular pentoses including the non-limiting examples of xylose and L-arabinose.

The Crabtree-negative cells of the invention are preferably selected from the *Candida* strains *C. sonorensis, C. methanosorbosa, C. diddensiae, C. parapsilosis, C. naeo-* dendra, *C. krusei*, *C. blankii*, and *C. entomophila*. In preferred embodiments the cells *C. sonorensis* and *C. methanosorbosa* cells.

Methods for isolating organic products produced by the cells of the invention are well known in the art. In particular, methods for separating lactic acid from a fermentation mixture, including low pH fermentation mixtures, are disclosed by Eyal et al. (International Patent Application, Publication No. WO 99/19290, published Apr. 22, 1999). Such methods for isolating lactic acid include extraction, adsorption, distillation/vaporization, separation via a membrane, crystallization, and phase splitting. (See also: Vickroy, 1985, *Comprehensive Biotechnology,* (Moo-Young, ed.), Volume 3, Chapter 38 Pergamon Press, Oxford; Datta et al., 1995, *FEMS Microbiol. Rev.* 16: 221–231; U.S. Pat. Nos. 4,771,001; 5,132,456; 5,510,526; and 5,420,304).

Fermentation Conditions

Various fermentation processes can be used with the various aspects of the instant invention. (See, e.g., Wolf, 1996, *Nonconventional Yeasts in Biotechnology,* Springer-Verlag Berlin, and Walker, 2000, *Yeast Physiology and Biotechnology,* John Wiley & Sons, England). Those of skill in the art will recognize that fermentation conditions can be varied to improve various aspects of the fermentation, including product yield, culture productivity, and culture health (among others), depending on the specific host organism and desired product. It is particularly advantageous to use the favorable characteristics of *Candida* in adjusting the fermentation conditions. Thus, the pH can have a range during various stages of processing from about 2.5 to about 9.0. Oxygen levels can vary from about 0% to about 100% (relative to the oxygen content found in air), as measured in the atmosphere above the medium or dissolved in the medium. Oxygen levels can be measured or calculated by any common methods including partial pressure, $O_2$ electrode, volume/volume, or gas flow rate (VVM). Temperature ranges can span from about ambient temperature (23° C.) to about 40° C. and above (e.g. to about 45° C.).

Preferred fermentation conditions include maintenance of a pH range from about 4 to about 5. It is especially preferred to maintain a pH of about 5 during biomass production and during lactic acid production. Preferably, the pH is maintained throughout the entirety of the fermentation process by automated addition of a base, for example $Ca(OH)_2$. The temperature during biomass production is preferably maintained at about 35° C. Preferably the biomass is produced under aerobic conditions wherein the culture medium is preferably agitated and supplied an airflow, until an adequate cell mass for lactic acid production is attained. During production of lactic acid, the agitation rate and airflow are preferably slowed, relative to their rate during biomass production.

The following data was generated from three different fermenter cultivations on glucose medium under the preferred conditions detailed above.

| | | | | | Overall yield and productivity | | | | | |
|---|---|---|---|---|---|---|---|---|---|---|
| | | CDW | | | LA | Glu | Yield | | Productivity | |
| Batch | Strain | (g/l) | pH* | Base | g/L | (final) | (%) | Time/h | g/l/h | g/g-cell/h |
| 602 | C40/288-34 | 5.1 | 5 | Ca(OH)2 | 73 | 0 | 81 | 34 | 2.15 | 0.42 |
| 802 | C40/288-34 | 5 | 5/4 | Ca(OH)2 | 49 | 3 | 70 | 90 | 0.54 | 0.11 |
| 902 | C40/288-34 | | 4/4 | Ca(OH)2 | | | | | | |

*pH during biomass production/pH during lactate production

| | | | | Yield and productivity in lactate production phase | | | | | | |
|---|---|---|---|---|---|---|---|---|---|---|
| | | CDW | | Glu | Glu | LA | LA | | Yield | Productivity |
| Batch | Strain | (g/l) | pH | (init.) | (final) | (init.) | (final) | Time/h | (%) | g/l/h g/g-cell/h |
| 602 | C40/288-34 | 5.1 | 5 | 63 | 0 | 12.5 | 73 | 21.5 | 96 | 2.81 0.55 |
| 802 | C40/288-34 | 5 | 4 | 58 | 3 | 2 | 49 | 77 | 87 | 0.61 0.12 |
| 902 | C40/288-34 | | 4 | | | | | | | |

The following examples serve to illustrate certain embodiments of the invention and do not limit it in scope or spirit.

EXAMPLES

Example 1

G418 Resistance Vectors and Use of G418 for Selection of *C. sonorensis* Transformants Vectors conferring G418 resistance on transformed yeast cells, which permit selection of yeast cell transformants comprising a recombinant nucleic acid construct encoding a protein useful for synthesis of an organic product, were prepared as follows. The G418 resistance marker was cloned to be under the transcriptional control of either the *C. sonorensis* PGK1 or TDH1 promoter and the constructs were designated as pMI268 (FIG. 2) and pMI269 (FIG. 3), respectively. The *S. cerevisiae* GAL10 terminator was used in both cases.

The G418 resistance gene was amplified by polymerase chain reaction (PCR) using the Dynazyme EXT Polymerase (Finnzymes, Espoo, Finland) using a pair of oligonucleotide primers having the sequence: CTAG<u>TCTAGA</u> ACA ATG AGC CAT ATT CAA CGG GAA ACG (G418 5'; SEQ ID NO:1) and CGC <u>GGATCC</u> GAA TTC TTA GAA AAA CTC ATC GAG CAT CAA ATG (G418 3'; SEQ ID NO:2). The plasmid pPIC9K (obtained from Invitrogen) was used as template. PCR was performed by initially incubating the reaction mixture for 5 min at 95° C., followed by 29 cycles of 45 sec at 95° C., 45 sec at 55° C., and 2 min at 72° C., with a final incubation for 5 min at 72° C. The PCR product was digested with restriction enzymes BamHI and XbaI and an 800 bp fragment was isolated. This fragment was ligated to the 4226 bp BamHI-XbaI fragment of pNC101 (obtained from Eric Jarvis at NREL). Plasmid pNC101 was constructed from the phosphoglycerate kinase promoter (PGK) and the GAL10 terminator sequences from *S. cerevisiae*, using standard cloning techniques (see, e.g., Sambrook et al., Ld.). This plasmid also harbors an LDH gene from *K. thermotolerans* inserted between XbaI and EcoRI sites, which, along with a BamHI site, are contained in a polylinker region found between the yeast promoter and terminator sequences. This plasmid permits expression of various genes or selectable markers, under the control of the yeast promoter and terminator.

The plasmid resulting from these manipulations contains the G418 resistance gene between the *S. cerevisiae* PGK1 promoter and the *S. cerevisiae* GAL10 terminator, and was named pMI260. The structure of this plasmid is shown schematically in FIG. 1.

The 600 bp TDH1 promoter of *C. sonorensis* was amplified by PCR using the Dynazyme EXT Polymerase with a pair of oligonucleotide primers having the sequence: GCG ATC TCG AGA AAA TGT TAT TAT AAC ACT ACA C (5441; SEQ ID NO:3) and CTAGTCTAGATT TGT TTG ATT TGT TTG TTT TGT TTT TGT TTG (Cs1; SEQ ID NO:4) using pMI238 as a template (see above "Vectors and Host Cells"; shown in FIG. 6). PCR was performed by initially incubating the reaction mixture for 5 min at 95° C., followed by 29 cycles of 45 sec at 95° C., 45 sec at 55° C., 2 min at 72° C., with a final incubation for 5 min at 72° C. The PCR product was made blunt ended with Klenow polymerase and each of the 4 dNTPs and then digested with the restriction enzyme XbaI. The resulting 600 bp fragment was ligated with the 4216 bp PstI (made blunt ended with T4 polymerase)-XbaI fragment of pMI260. The resulting plasmid contains the G418 resistance gene operatively linked to the *C. sonorensis* TDH1 promoter and the *S. cerevisiae* GAL10 terminator and was named pMI269. The structure of this plasmid is shown schematically in FIG. 3.

The 1500 bp *C. sonorensis* PGK1 promoter was amplified by PCR using the Dynazyme EXT Polymerase with a pair of oligonucleotide primers having the sequence: GCG ATC TCG AGA AAG AAA CGA CCC ATC CAA GTG ATG (5423; SEQ ID NO:5) and CTA GTC TAG ATG TAT ATA GTC TTT TCT ATT ATT AG (Cs2;SEQ ID NO:6) using pMI234 as the template (see above "Vectors and Host Cells"; FIG. 5). PCR was performed by initially incubating the reaction mixture for 5 min at 95° C., followed by 29 cycles of 45 sec at 95° C., 45 sec at 55° C., 2 min at 72° C., with a final incubation for 10 min at 72° C. The 1500 bp PCR product fragment was made blunt ended with Klenow polymerase and each of the 4 dNTPs and then digested with the restriction enzyme XbaI. The 1500 bp PGK1 promoter fragment was ligated with the 4216 bp PstI (made blunt ended with T4 polymerase)-XbaI fragment of pMI260. The resulting plasmid contains the G418 resistance gene operatively linked to the *C. sonorensis* PGK1 promoter and the *S. cerevisiae* GAL10 terminator, and was named pMI268. The structure of this plasmid is shown schematically in FIG. 2.

The two constructs pMI268 and pMI269 were digested with restriction enzymes SalI and NotI and transformed into *C. sonorensis* using the chemical method according to Gietz et al (1992, *Nucleic Acids Res.* 20:1425). This transformation technique was used throughout these Examples, and is described briefly as follows.

Cells from an overnight culture of *C. sonorensis* grown to an $OD_{600}$ of 0.8–1.5 were collected by centrifugation, and were washed first with an excess of a solution of 10 mM Tris-HCl, 1 mM EDTA (pH 7.5), followed by washing with an excess of a solution of 100 mM lithium acetate (LiAc), 10 mM Tris-HCl, 1 mM EDTA (pH 7.5), and then resuspended in 2 mL of a solution of 100 mM LiAc, 10 mM Tris-HCl, 1 mM EDTA (pH 7.5). Cells were mixed (about 50 µL of the 2 mL suspension) with about 10 µg of transforming DNA and 300 µL of a solution of 40% PEG4000, 100 mM LiAc, 10 mM Tris-HCl, 1 mM EDTA (pH 7.5). The cells were incubated at 30° C. for 30 min with slow shaking. Dimethyl sulfoxide (DMSO; 40 µL) was added and the cells were incubated in a 42° C. water bath for 15 min. The cells were collected by centrifugation, washed with an excess of a solution of 10 mM Tris-HCl, 1 mM EDTA (pH 7.5), resuspended and incubated at 30° C. in YPD medium (comprising 10 g/L yeast extract, 20 g/L peptone and 20 g/L glucose) for 3–7 h. Optionally, the YPD incubation can be continued overnight.

Before applying selection the cells were incubated in liquid YPD for at least 3 h or overnight. The transformants were grown on YPD agar plates (comprising 10 g/L yeast extract, 20 g/L peptone, 20 g/L glucose and 2% agar) supplemented with G418 antibiotic at a concentration of either 100 µg/mL or 200 µg/mL. The plates were incubated at 30° C. for 2–5 days and the transformants were then restreaked onto fresh selection plates. Southern analysis of total DNA isolated from the G418 resistant colonies showed that the G418 resistance gene was integrated in the genome of the transformants.

These results showed that the G418 resistance gene can be expressed from the constructs prepared as described herein and is a suitable selection for *C. sonorensis* transformation.

Example 2

Hygromycin Resistance (hgh) Vectors and Use of Hygromycin B for Selection of *C. sonorensis* Transformants Vectors conferring hygromycin resistance on transformed yeast cells, which permit selection of yeast cell transformants comprising a recombinant nucleic acid construct encoding a protein useful for synthesis of an organic product, were prepared as follows. The hygromycin resistance marker (*E. coli* hph) was cloned under the transcriptional control of either the *C. sonorensis* PGK1 and TDH1 promoter and the constructs were designated as pMI270 (FIG. 4) and pMI271, respectively. The *S. cerevisiae* GAL10 terminator was used in both cases.

The *E. coli* hph gene that confers resistance to hygromycin B was obtained from the plasmid pRLMex30 (Mach et al. 1994, *Curr. Genet.* 25, 567–570). pRLMex30 was linearized with the restriction enzyme NsiI and made blunt ended with T4 DNA polymerase and then digested with XbaI.

The pMI268 plasmid prepared in Example 1 was digested with EcoRI and was made blunt ended with Klenow polymerase and each of the 4 dNTPs and then digested with XbaI. The resulting 4900 bp fragment was ligated with the 1035 bp hph fragment from pRLMex30. This ligation produced a plasmid that contains the hygromycin resistance gene operatively linked to the *C. sonorensis* PGK1 promoter and the *S. cerevisiae* GAL10 terminator, and was named pMI270. The structure of this plasmid is shown schematically in FIG. 4.

The pMI269 plasmid prepared in Example 1 was digested with EcoRI and was made blunt ended with Klenow polymerase and each of the 4 dNTPs and then digested with XbaI. The resulting 4000 bp fragment was ligated with the 1035 bp hph fragment of pRLMex30. This produced a plasmid that contains the hygromycin resistance gene operatively linked to the *C. sonorensis* TDH1 promoter and the *S. cerevisiae* GAL10 terminator, and was named pMI271. The structure of this plasmid is shown schematically in FIG. 7.

Yeast cells were transformed using the chemical method according to Gietz et al. (1992, *Nucleic Acids Res.* 20: 1425) as described in Example 1 above. The two constructs pMI270 and pMI271 were digested with the restriction enzymes XhoI and NotI. The transformation mixture was incubated in YPD at 30° C. for 3 h before plating onto selective plates. The transformants were grown at 30° C. for 2–5 days on YPD agar plates supplemented with hygromycin B (Calbiochem) at concentrations of 150–300 µg/mL. Transformants were restreaked onto fresh selection plates. The presence of the transformed DNA in the genome of the hygromycin resistant transformants was verified by PCR using a pair of oligonucleotide primers having the sequence: CCGGACTA GTT GGT ACA GAG AAC TTG TAA ACA ATT CGG (ScerGal10t; SEQ ID NO:7) and TAT AAA TAC TTA TCA TTT CCTCC (5436; SEQ ID NO:8). PCR was performed by initially incubating the reaction mixture for 3 min at 94° C., followed by 29 cycles of 45 sec at 94° C., 45 sec at 55° C., 2 min at 72° C., with a final incubation for 10 min at 72° C.

These results show that the *E. coli* hph gene can be expressed using the constructs described herein, functions in *C. sonorensis* and that hygromycin B can be used to select *C. sonorensis* transformants.

Example 3

Vectors for Expression of the *L. helveticus* LDH and for Targeted Integration of the Transformed DNA into the PDC1 Locus Vectors comprising a *L. helveticus* LDH gene for targeted integration into the *C. sonorensis* PDC1 gene locus were prepared as follows. The pMI246 vector contains the MEL5 expression cassette and the *L. helveticus* LDH expression cassette, shown schematically in FIG. 8 (see above "Vectors and Host Cells"). In order to construct a vector that enables targeted integration into the *C. sonorensis* PDC1 locus and replacement of the PDC1 protein-coding region, DNA fragments corresponding to sequences immediately upstream and downstream of the PDC1 protein-coding region were added into pMI246.

The PDC1 terminator was amplified by PCR using the Dynazyme EXT Polymerase (Finnzymes, Espoo, Finland) with oligonucleotide primers having the sequence: GGG ACT AGT GGA TCC TTG AAG TGA GTC AGC CAT AAG GAC TTA AATTCACC (Cs7; SEQ ID NO:9) and AAGGCCT TGT CGA CGC GGC CGC TTG GTT AGA AAA GGT TGT GCC AAT TTA GCC (Cs8; SEQ ID NO:10), using *C. sonorensis* genomic DNA as a template. PCR was performed by initially incubating the reaction mixture for 5 min at 95° C., followed by 29 cycles of 45 sec at 95° C., 45 sec at 55° C., 2 min at 72° C., with a final incubation for 10 min at 72° C. The 920 bp PCR product fragment was digested with restriction enzymes BamHI and NotI and the 920 bp fragment was purified and ligated with the 8900 bp BamHI-NotI fragment from pMI246. The resulting plasmid was named pMI256, and is shown schematically in FIG. 18.

The PDC1 promoter was amplified from *C. sonorensis* with a pair of oligonucleotide primers having the sequence: GGG ACG GGC CCG CGG CCG CTA CAA GTG ATT CAT TCA TTC ACT (Cs5; SEQ ID NO:11) and CCC TGG GCC CCT CGA GGA TGA TTT AGC AAG AAT AAA TTA AAA TGG (Cs6; SEQ ID NO:12) using genomic *C. sonorensis* DNA as a template. PCR was performed by initially incubating the reaction mixture for 5 min at 95° C., followed by 29 cycles of 45 sec at 95° C., 45 sec at 55° C., 2 min at 72° C., with a final incubation for 10 min at 72° C. The PCR product fragment was digested with ApaI and the 800 bp fragment was purified and ligated with the 9760 bp ApaI linearized pMI256 (see above "Vectors and Host Cells"; FIG. 18). The resulting plasmid was named pMI257, and is shown schematically in FIG. 10. pMI257 contains, in order, the *C. sonorensis* PDC1 promoter, the *C. sonorensis* PGK1 promoter operatively linked to the *S. cerevisiae* MEL5 gene, the *C. sonorensis* PGK1 promoter operatively linked to the *L. helveticus* LDH and the *S. cerevisiae* CYC1 terminator followed by the *C. sonorensis* PDC1 terminator.

pMI257 was digested with NotI to excise the 7300 bp fragment containing the MEL5 and LDH expression cassettes flanked by the PDC1 5' and 3' regions. This 7300 bp fragment was used to transform *C. sonorensis* by the method described in Example 1 above, and the transformants were screened based on expression of the MEL5 marker. The transformants were grown on YPD agar plates supplemented with the chromogenic substrate of α-galactosidase, 5-bromo-4-chloro-3-indolyl-α-D-galactopyranoside (X-α-gal; ICN Biochemicals) at a concentration of 40 µg/mL. The plates were incubated at 30° C. for 1–3 days and then transferred to 4° C. In the presence of X-α-gal yeast colonies transformed with a functional MEL5 expression cassette turned blue, whereas the untransformed colonies were white. Blue colonies were purified by restreaking them onto fresh indicator plates. The transformants originating from the transformation of *C. sonorensis* with NotI digested pMI257 were designated as 257-1 through 257-15, 257-41, 257-42, and 257-45.

Southern blot analysis of genomic DNA isolated from the pMI257 transformants was carried out with the *C. sonorensis* PDC1 probe to identify transformants in which the anticipated replacement of the PDC1 open reading frame by the transformed pMI257 DNA had occurred. The absence of a PDC1 hybridizing band in transformants 257-3, 257-9, 257-12, 257-15, and 257-41 indicated that PDC1 gene was deleted. Other pMI257 transformants and *C. sonorensis* gave a positive signal in the PDC1 hybridization. Hybridization with the *L. helveticus* LDH probe showed that the LDH gene was present in one copy in the pdc1 deletants. Transformants 257-6 257-7, and 257-8 contained two copies of the *L. helveticus* LDH randomly integrated into the genome. Other pMI257 transformants had one copy of LDH randomly integrated in the genome.

These results show that targeted integration of the transformed pMI257 DNA into the PDC1 locus occurred through homologous recombination between PDC1 promoter and terminator sequences. These results also show that PDC1 is a single copy gene in *C. sonorensis*. In addition, integration events outside the PDC1 locus occurred. In some transformants the LDH gene was integrated in more than one copy into the genome.

Example 4

Vectors for Expression of the *B. megaterium* LDH and for Targeted Integration of the Transformed DNA into the PDC1 Locus Vectors comprising a *B. megaterium* LDH gene for targeted integration into the *C. sonorensis* PDC1 gene locus were prepared as follows. In these vectors, the *L. helveticus* LDH in pMI257 was replaced by the *B. megaterium* LDH.

pMI257 was linearized with NcoI and the 5' overhangs were partially filled in with DNA polymerase I, Klenow fragment, and a mixture of dATP, dCTP, and dTTP, omitting dGTP from the reaction. This was followed by removal of the single stranded extensions by treatment with mung bean nuclease. The DNA was then digested with BamHI and the 9200 bp fragment was isolated from a 0.8% agarose gel after electrophoretic separation. Vector pVR24 containing *B. megaterium* LDH was generated from *B. megaterium* genomic DNA, and is shown in FIG. 21. The LDH gene was cloned from the genomic DNA by PCR using primers designed from accession no. M22305, and ligated into a commercially-available vector (see above "Vectors and Host Cells"). The 976 bp fragment containing the *B. megaterium* LDH was excised from pVR24. by XbaI digestion followed by fill-in of the 5' overhangs by DNA polymerase I, Klenow fragment and each of the 4 dNTPs, and digestion by BamHI. The 9200 bp NcoI (blunt)-BamHI fragment from pMI257 and the 976 bp XbaI(blunt)-BamHI fragment from pVR24 were ligated and the resulting plasmid was designated as pMI265, shown in FIG. 11. pMI265 contains, in order, the *C. sonorensis* PDC1 promoter, the *C. sonorensis* PGK1 promoter operatively linked to the *S. cerevisiae* MEL5 gene, the *C. sonorensis* PGK1 promoter operatively linked to the *B. megaterium* LDH and the *C. sonorensis* PDC1 terminator. pMI265 was digested with NotI to excise the 7300 bp fragment that consisted of the MEL5 and LDH expression cassettes flanked by the PDC1 5' and 3' regions. This 7300 bp fragment was used to transform *C. sonorensis* as described in Example 1 and the transformants were screened on YPD plates supplemented with X-α-gal at a concentration of 40 μg/mL. The transformants were grown on YPD agar plates supplemented with X-α-gal (40 μg/mL). The transformants originating from the transformation of *C. sonorensis* with NotI-digested pMI265 were designated as 265-1 through 265-60.

Southern blot analysis of genomic DNA isolated from the pMI265 transformants was carried out with the *C. sonorensis* PDC1 probe to identify transformants in which the anticipated replacement of the PDC1 open reading frame by the transformed pMI265 DNA had occurred. The absence of a PDC1 hybridizing band in transformants 265-5, 265-7, 265-15, 265-17, 265-33, 265-34, 265-35, 265-38, 265-39, 265-42, 265-43, 265-47, 265-48, 265-49, 265-51, and 265-60 indicated that the PDC1 gene was deleted. Other pMI265 transformants and untransformed *C. sonorensis* gave a positive signal for PDC1 hybridization. Hybridization with the *B. megaterium* LDH probe showed that the LDH gene was present in one copy in the pdc1 deletants. Positively PDC1-hybridizing transformants 265-14, 265-22 and 265-23 contained two copies and 265-56 contained three copies of the LDH gene randomly integrated into the genome. Other pMI265 transformants had one copy of LDH randomly integrated in the genome.

These results showed that targeted integration of the transformed pMI265 DNA into the PDC1 locus occurred through homologous recombination between PDC1 promoter and terminator sequences. These results also confirmed that PDC1 is a single copy gene in *C. sonorensis*. The transformants deleted of pdc1 were viable, indicating that PDC1 is not an essential gene in *C. sonorensis*. In addition to PDC1-deleting integrations, integration events outside the PDC1 locus occurred in certain transformants. In some transformants the LDH gene was integrated in more than one copy into the genome.

Example 5

Vectors for Expression of *R. oryzae* LDH and for Targeted Integration of the Transformed DNA into the PDC1 Locus Vectors comprising a *R. oryzae* LDH gene for targeted integration into the *C. sonorensis* PDC1 gene locus were prepared as follows. In these vectors, the *L. helveticus* LDH encoding sequences in pMI257 were replaced by *R. oryzae* LDH.

The pMI257 plasmid described in Example 3 above was linearized with NcoI and the 5' overhangs were partially filled in with DNA polymerase I, Klenow fragment, and a mixture of dATP, dCTP, and dTTP, omitting dGTP from the reaction. This was followed by removal of the single stranded extensions by treatment with mung bean nuclease. The DNA was then digested with BamHI and the 9200 bp fragment was isolated from a 0.8% agarose gel after electrophoretic separation. The coding sequence of *R. oryzae* LDH-encoding DNA was operatively linked to the *C. sonorensis* PGK1 promoter and the transcriptional terminator of the *C. sonorensis* PDC1 gene. Vector pVR 27 containing *R. oryzae* LDH was generated from *R. oryzae* genomic DNA, and is shown in FIG. 22. The LDH gene was cloned from the genomic DNA by PCR using primers designed from accession no. AF226154, and ligated into a commercially-available vector (see above "Vectors and Host Cells"). The 978 bp fragment containing the *R. oryzae* LDH was excised from pVR27 by XbaI digestion followed by fill in of the 5' overhangs by DNA polymerase I, Klenow fragment and each of the 4 dNTPs and digestion by BamHI. The 9200 bp NcoI (blunt)-BamHI fragment from pMI257 and the 978 bp XbaI(blunt)-BamHI from pVR27 were ligated and the resulting plasmid containing was designated as pMI266, shown schematically in FIG. 12. pMI266 contains, in order, the *C. sonorensis* PDC1 promoter, the *C. sonorensis* PGK1 promoter operatively linked to the *S. cerevisiae* MEL5 gene, the *C. sonorensis* PGK1 promoter operatively linked to the *R. oryzae* LDH A and the *C. sonorensis* PDC1 terminator. pMI266 was digested with NotI to excise a 7300 fragment that consisted of the MEL5 and LDH expression cassettes flanked by the PDC1 5' and 3' regions. This 7300 bp fragment was used to transform *C. sonorensis* by the method described in Example 1 above, and the transformants were screened on YPD plates supplemented with X-α-gal at a concentration of 40 μg/mL. The transformants originating from the transformation of *C. sonorensis* with NotI-digested pMI266 were designated as 266-1 through 266-13.

Southern blot analysis of genomic DNA isolated from the pMI266 transformants was carried out with the *C. sonorensis* PDC1 probe to identify transformants in which the anticipated replacement of the PDC1 open reading frame by the transformed pMI266 DNA had occurred. The absence of a PDC1 hybridizing band in transformants 266-1, 266-3, 266-4, and 266-11 indicated that PDC1 gene was deleted. In contrast, pMI266 transformants 266-2, 266-7 and 266-8 and untransformed *C. sonorensis* gave a positive signal in the PDC1 hybridization. Hybridization with the LDH probe showed that the *R. oryzae* LDH gene was present in one copy in all the transformants.

These results showed that targeted integration of the transformed pMI266 DNA into the PDC1 locus occurred through homologous recombination between PDC1 promoter and terminator sequences. In addition, integration events outside the PDC1 locus occurred.

Example 6

Vector for Replacement of PDC1 Without LDH

Vectors were prepared for replacing PDC1 without introducing exogenous LDH-encoding sequences. The pMI257 plasmid described in Example 3 above was digested with NcoI and BamHI in order to remove the LDH gene and the *S. cerevisiae* CYC1 terminator. The 5' overhangs were filled in by DNA polymerase I, Klenow fragment, and each of the 4 dNTPs. The 9200 bp fragment was purified after agarose gel electrophoresis and recircularized by incubation at a concentration of 40 ng/µL in the presence of 400 U of T4 DNA ligase (New England Biolabs) and the appropriate buffer recommended by the manufacturer. The resulting plasmid was named pMI267, and is shown schematically in FIG. 13. pMI267 contains, in order, the *C. sonorensis* PDC1 promoter, the *C. sonorensis* PGK1 promoter operatively linked to the *S. cerevisiae* MEL5 gene, and the *C. sonorensis* PDC1 terminator.

pMI267 was digested with NotI to excise the 6300 bp fragment that consisted of the MEL5 cassette flanked by the PDC1 5' and 3' regions. This 6300 bp fragment was used to transform *C. sonorensis* by the method described above in Example 1 and the transformants were screened on YPD plates supplemented with X-α-gal at a concentration of 40 µg/mL. The transformants originating from transformation of *C. sonorensis* with NotI digested pMI267 were designated as 267-1 through 267-10.

Southern blot analysis of genomic DNA isolated from the pMI267 transformants was carried out with the *C. sonorensis* PDC1 probe to identify transformants in which PDC1 open reading frame was deleted. The absence of a PDC1 hybridizing band in transformants 267-1 and 267-10 indicated that the PDC1 gene was deleted.

These results showed that targeted integration of the transformed pM1267 DNA into the PDC1 locus occurred through homologous recombination between the PDC1 promoter and terminator sequences. LDH expression was not required to maintain the viability of the pdc1-deleted strain. In addition, integration events outside the PDC1 locus occurred.

Example 7

Construction of a *C. sonorensis* Vector Containing the *B. megaterium* LDH Gene and the G418 Marker A vector comprising the G418 resistance gene and *B. megaterium* LDH gene was prepared as follows. In these vectors, the *B. megaterium* LDH expression cassette from the plasmid pMI265 and the G418 resistance marker cassette from the plasmid pMI269 were combined into the same vector. The pMI269 plasmid described in Example 1 was digested with EcoRI and the 5' overhangs were filled in by DNA polymerase I, Klenow fragment, and each of the 4 dNTPs, followed by digestion of the DNA with BamHI. The 4800 bp EcoRI(blunt)-BamHI fragment of pMI269 was ligated with 2800 bp MscI-BamHI fragment from the pMI265 plasmid described in Example 4. The resulting plasmid was named pMI278 and contains, in order, the *C. sonorensis* TDH1 promoter operatively linked to the G418 resistance gene and the MEL5 terminator followed by the *C. sonorensis* PGK1 promoter operatively linked to the *B. megaterium* LDH and the *S. cerevisiae* GAL10 terminator, and is shown schematically in FIG. 14.

Example 8

Construction of *C. sonorensis* Strains Expressing the *R. oryzae* LDH and the *B. megaterium* LDH Simultaneously The *C. sonorensis* transformant designated 266-3, in which the *R. oryzae* LDH is integrated into the pdc1 locus, was chosen as host for a second transformation with the *B. megaterium* LDH construct described in Example 4 above. Transformant 266-3 was further transformed with SalI-NotI digested pMI278 and the transformants were selected on YPD agar plates supplemented with G418 antibiotic at a concentration of 200 µg/mL. The plates were incubated at 30° C. for 2–5 days for selection; transformants were purified by restreaking onto fresh selection plates. The resulting transformants were designated as 278-1 through 278-20. The presence of the *B. megaterium* LDH in the genome of 19 of these transformants was verified by Southern blot analysis of HindIII digested yeast DNA using the *B. megaterium* LDH gene as the probe. Some of the transformants had more than one copy of the *B. megaterium* LDH integrated in the genome. Southern blot analysis was repeated with the *R. oryzae* LDH gene as a probe to verify that the *R. oryzae* LDH was still present.

This experiment showed that *C. sonorensis* could be transformed multiply and independently with different markers. In this way it was demonstrated to be possible to increase the copy number of the gene of interest (LDH) in the host genome.

Example 9

Vectors for Expression of *B. megaterium* LDH and for Targeted Integration of the Transformed DNA into the PDC2 Locus Vectors comprising a *B. megaterium* LDH gene for targeted integration into the *C. sonorensis* PDC2 gene locus were prepared as follows. *C. sonorensis* PDC2 promoter was amplified by PCR using the Dynazyme EXT polymerase and a pair of oligonucleotide primers having the sequence: GGG ACG GGC CCG CGG CCG CTT ACA GCA GCA AAC AAG TGATGCC (Cs26; SEQ ID NO:13) and CCC TGG GCC CCT CGA GTT TGA TTT ATT TGC TTT GTA AAGAGAA (Cs27; SEQ ID NO:14). The genomic copy of the *C. sonorensis* PDC2 cloned in a lambda vector was used as the template (see above). PCR was performed by initially incubating the reaction mixture for 3 min at 94° C., followed by 29 cycles of 45 sec at 94° C., 45 sec at 55° C., 2 min at 72° C., with a final incubation for 10 min at 72° C. The 1000 bp PCR product was cloned into the TOPO TA vector (Invitrogen) and the resulting plasmid was named pMI277, shown schematically in FIG. 19. The PDC2 promoter was released by EcoRI digestion and made blunt ended with the Klenow polymerase and each of the 4 dNTPs.

The pMI278 plasmid prepared as described in Example 7 was linearized by SalI and the 5' overhangs were filled in by Klenow polymerase and each of the 4 dNTPs, then ligated to the 1000 bp EcoRI (blunt) fragment of the pMI277 plasmid. The plasmid containing the insert in the desired orientation was named pMI279, shown schematically in FIG. 20.

The PDC2 terminator was amplified by PCR using the Dynazyrne EXT polymerase with a pair of oligonucleotide primers having the sequence: TGGAC<u>TAGT</u>TAG<u>ATAG</u> CAA TTC TTA CTT GAA AAA TTA ATT GAA GCA TTACC (Cs29; SEQ ID NO:15) and GGC CCG CGG CCG CTA AAT ATA ATT ATC GCT TAG TTA TTA AAA TGG (Cs30; SEQ ID NO:16), using the genomic copy of the C. sonorensis PDC2 gene cloned in a lambda vector as the template. The pdc2 terminator fragment includes part of the open reading frame corresponding to the 239 C-terminal amino acids. Translation stop codons were introduced in the PCR oligonucleotide Cs29 in all three frames upstream of the nucleotides corresponding to the last 239 C-terminal amino acids protein in the terminator fragment. PCR was performed by initially incubating the reaction mixture for 3 min at 94° C., followed by 29 cycles of 45 sec at 94° C., 45 sec at 55° C., 2 min at 72° C., with a final incubation for 10 min at 72° C. The PCR product was made blunt ended with the Klenow polymerase and each of the 4 dNTPs, and purified with a Qiaquick column (Qiagen). The PCR product was phosphorylated with T4 polynucleotide kinase and rATP at a concentration of 1 mM under standard conditions (see Sambrook et al., Id.). The 800 bp PDC2 terminator fragment was purified after agarose gel electrophoresis and ligated with NeoI (blunt) digested pMI279 that was dephosphorylated with calf intestinal phosphatase. The resulting plasmid was named pMI286 and contains, in order, the C. sonorensis PDC2 promoter, the C. sonorensis TDH1 promoter operatively linked to the G418 resistance gene and the S. cerevisiae MEL5 terminator, the C. sonorensis PGK1 promoter operatively linked to the B. megaterium LDH gene, the S. cerevisiae GAL10 terminator followed by the C. sonorensis PDC2 terminator. This construct is shown schematically in FIG. 15.

The pMI286 plasmid was digested with NotI to excise the 6400 bp fragment that consisted of the G418 resistance and LDH expression cassettes flanked by the PDC2 5' and 3' regions. This 6400 bp fragment was used to transform C. sonorensis by the method described in Example 1 above. The transformants were grown on YPD agar plates supplemented with G418 antibiotic at a concentration of 200 µg/mL. The plates were incubated at 30° C. for 2–5 days and the transformants were then restreaked onto fresh selection plates. The transformants were designated as 286-1 through 286-40.

Southern blot analysis of genomic DNA isolated from the pMI286 transformants was carried out with the C. sonorensis PDC2 probe (corresponding to nucleotides in the deleted area) to identify transformants in which B. megaterium LDH was integrated into the PDC2 locus. The absence of a PDC2 hybridizing band in transformants 286-1, 286-2, 286-4, 286-19, and 286-30 indicated that PDC2 gene was deleted. Other pMI286 transformants and untransformed C. sonorensis gave a positive signal in the PDC2 hybridization. Hybridization with the B. megaterium LDH probe showed the LDH was present in one copy in the pdc2 deletants. The frequency of targeted integration into the PDC2 locus was 15%.

These results showed that targeted integration of the transformed pMI286 DNA into the PDC2 locus occurred through homologous recombination between PDC2 promoter and PDC2 terminator sequences. These results also show that the PDC2 is a single copy gene in C. sonorensis. In addition, integration events outside the PDC2 occurred. In some transformants the LDH gene was integrated in more than one copy into the genome.

Example 10

Construction of C. sonorensis Strains Deleted of pdc1 and Disrupted in pdc2 and Harboring Two Copies of B. megaterium LDH Integrated in the Genome in the pdc1 and pdc2 Loci The C. sonorensis transformant 265-15 having B. megaterium LDH integrated in the pdc1 locus was chosen as host for a second transformation with B. megaterium LDH. Transformant 265-15 was further transformed with NotI digested pMI286 using the methods described in Example 1 above, and the transformants were selected on YPD agar plates supplemented with G418 antibiotic at a concentration of 200 µg/mL. The plates were incubated at 30° C. for 2–5 days for selection, and transformants obtained thereby were purified by restreaking them onto fresh selection plates. The transformants were designated as C44/286-1 through C44/286-40.

Disruption of the pdc2 gene was verified using the PDC2 probe (corresponding to nucleotides in the deleted area). T he absence of PDC2 hybridizing band in transformants C44/286-10, C44/286-26, C44/286-27, C44/286-28, C44/286-29, C44/286-30, C44/286-31, C44/286-32, and C44/286-33 indicated that the PDC2 gene was deleted. The presence of B. megaterium LDH in the genome in two copies in the pdc1, pdc2 double deletants was verified by Southern analysis of HindIII digested yeast DNA using the B. megaterium LDH gene as the probe.

These results showed that targeted integration of the transformed pMI286 DNA into the PDC2 locus occurred through homologous recombination between PDC2 promoter and PDC2 terminator sequences. These results also confirm that the PDC2 is a single copy gene in C. sonorensis, and that integration events outside the PDC2 locus can occur. In some transformants the LDH gene was integrated in more than one copy into the genome. The transformants simultaneously deleted of pdc1 and disrupted in pdc2 are viable.

This Example also confirmed that C. sonorensis can be transformed multiply and independently when different markers are used. In this way it is also possible to increase copy number of the gene of interest (LDH) in the host genome.

Example 11

Ethanol Production by the pdc1-pdc2-strains

Ethanol production in Candida strains bearing deletions or disruptions in the PDC1 and/or PDC2 genes was assayed as follows. Transformants designated C44/286-10, C44/286-26, and C44/286-33 and four other strains included as controls were grown in 50 mL of YP+5% glucose in 250 mL shaker flasks at 250 rpm shaking and at a temperature of 30° C. Samples were withdrawn daily and cells were removed by centrifugation. Culture supernatant samples taken 56 h after inoculation were analyzed for ethanol by the ethanol UV method of Boehringer Mannheim (Table 1). These results showed that ethanol production by the transformants deleted of both pdc1 and pdc2 ethanol is reduced more than ten-fold compared to the strains containing an intact PDC1 or PDC2 gene.

These results demonstrated that both PDC1 and PDC2 encode functional pyruvate decarboxylases, since a drastic reduction in ethanol production is only observed when both of the genes are simultaneously deleted. The results also indicated that PDC2 disruption removing approximately 60% of the PDC2 open reading frame abolished PDC2 function.

TABLE 1

Ethanol production by C. sonorensis transformants on YP + 5% glucose at 56 h of cultivation.

| strain | Genotype | ethanol g/L |
| --- | --- | --- |
| C44/286-10 | 2 copies of BmLDH, pdc1-pdc2- | 0.2 |
| C44/286-26 | 2 copies of BmLDH, pdc1-pdc2- | 0.1 |
| C44/286-33 | 2 copies of BmLDH, pdc1-pdc2- | 0.1 |
| 265-15 | 1 copy of BmLDH, pdc1- | 6 |
| 286-1 | 1 copy of BmLDH, pdc2- | 6 |
| 286-30 | 1 copy of BmLDH, pdc2- | 3 |
| 265-23 | 2 copies of BmLDH, PDC+ | 4 |

Example 12

Vector for Disruption of PDC2 Without LDH

Vectors were prepared for replacing PDC2 without introducing exogenous LDH-encoding sequences. The *B. megaterium* LDH gene was removed from the pMI286 plasmid described in Example 9 as a 1276 bp SpeI-XbaI fragment. pMI286 was digested with SpeI and the linearized molecule partially digested with XbaI. The 8100 bp SpeI-XbaI fragment was isolated after gel electrophoresis and recircularized. The resulting plasmid termed pMI287 consists, in order, of the *C. sonorensis* PDC2 promoter, the *C. sonorensis* TDH1 promoter operatively linked to the G418 resistance gene and the *S. cerevisiae* MEL5 terminator, the *C. sonorensis* PGK1 promoter followed by the *C. sonorensis* PDC2 terminator, and is shown schematically in FIG. 16.

pMI287 was digested with NotI to excise the 5100 bp fragment that consisted of the G418 expression cassette flanked by the PDC2 5' and 3' regions. This 5100 bp fragment was used to transform *C. sonorensis* by the methods described in Example 1 above. Transformants were grown on YPD agar plates supplemented with G418 antibiotic at a concentration of 200 μg/mL. The plates were incubated at 30° C. for 2–5 days and the transformants were then restreaked onto fresh selection plates.

Transformants were designated as 287-1 through 287-57. Southern blot analysis of genomic DNA isolated from the pMI287 transformants was performed using a PDC2 probe that corresponded to nucleotides in the deleted region, in order to identify successful transformants. No PDC2 hybridizing band was observed in the transformants 287-6 and 287-16, indicating that the PDC2 gene was deleted.

Example 13

Vectors for Expression of *L. helveticus* LDH and for Targeted Integration of the Transformed DNA into the PDC2 Locus In order to replace sequences encoding *B. megaterium* LDH in pMI286 by *L. helveticus* LDH-encoding DNA, the pMI286 described in Example 9 was digested with the restriction enzyme SpeI and made blunt ended with DNA polymerase I, Klenow fragment, and each of the four dNTPs and then digested with BspMI. Plasmid pMI247 shown in FIG. 9 was digested with BamHI and made blunt ended with DNA polymerase I, Klenow fragment, and each of the four dNTPs and then digested with BspMI. The 6800 bp SpeI (blunt)—BspMI fragment of pMI286 and the 2700 bp BamHI(blunt)—BspMI fragment of pMI247 were ligated. The resulting plasmid termed pMI288 consists, in order, of the *C. sonorensis* PDC2 promoter, the *C. sonorensis* TDH1 promoter operatively linked to the G418 resistance gene and the *S. cerevisiae* MEL5 terminator, the *C. sonorensis* PGK1 promoter operatively linked to the *L. helveticus* LDH gene and the *S. cerevisiae* CYC1 terminator followed by the *C. sonorensis* PDC2 terminator, and is shown schematically in FIG. 17.

pMI288 was digested with NotI to excise the 6400 bp fragment that consisted of the G418 resistance and LDH expression cassettes flanked by the PDC2 5' and 3' regions. The *C. sonorensis* transformant designated 257-3 having the *L. helveticus* LDH integrated in the pdc1 locus was chosen as host for a second transformation with *L. helveticus* LDH. Transformant 257-3 was further transformed with the 6400 bp NotI fragment of pMI288 by the methods described in Example 1 above. Transformants were selected on YPD agar plates supplemented with G418 antibiotic at a concentration of 200 μg/mL. The plates were incubated at 30° C. for 2–5 days, and transformants obtained thereby were purified by restreaking them onto fresh selection plates. These transformants were designated as C40/288-1 through C40/288-40.

Disruption of the pdc2 gene was verified using a PDC2 probe corresponding to nucleotides in the deleted area of the locus. The absence of a PDC2 hybridizing band in transformants C40/288-2, C40/288-11, C40/288-29, C40/288-34, and C40/288-38, indicated that the PDC2 gene was deleted. The presence of *L. helveticus* LDH in the genome in two copies in the pdc1, pdc2 double deletants was verified by Southern blot analysis of HindIII digested yeast DNA using the *L. helveticus* LDH gene as the probe.

These results demonstrated that targeted integration of exogenous LDH sequences into *C. sonorensis* PDC2 locus was achieved, and provided cells with disrupted PDC2 loci.

Example 14

Production of L-lactic Acid in Defined or Rich Glucose Medium in Aerobic Test Tube Cultures by *C. sonorensis* Harboring *L. helveticus* or *B. megaterium* LDH Gene Integrated into the Genome

*C. sonorensis* cells and the transformants disclosed in the Examples above (namely, 246-27, 247-11, 265-03, 265-05, 265-06, 265-07, 265-11, 265-12, 265-14, 265-15, 265-17, 265-18, 265-22, 265-23, 265-29, 265-33, 265-34, 265-35, 265-38, 265-39, 265-42, 265-43, 265-44, 265-45, 265-46, 265-47, 265-48, 265-49, 265-51, 265-52, 265-55, 265-56, 265-57, and 265-60) were cultivated in YPD medium (YP supplemented with 5% glucose and 0.5 M MES pH 5.5) or YD medium (yeast nitrogen base without amino acids supplemented with 2% glucose and 0.5 M MES pH 5.5). Two independent colonies from each transformant were inoculated into a 14 mL disposable plastic tube containing 5 mL of YPD or YD medium and cultivated with 250 rpm shaking at 30° C. Samples were withdrawn during cultivation, $OD_{600}$ measured, and cells removed by centrifugation and the culture supernatant analyzed by HPLC for lactic acid, glucose and ethanol. HPLC analyses were carried out with Waters 510 HPLC pump, Waters 717+ autosampler, and Water System Interfase Module liquid chromatography complex with refractive index detector (Waters 410 Differential refractometer) and UV-detector (Waters 2487 dual λ UV detector). An Aminex HPX-87H Ion Exclusion Column (300 mm×7.8 mm, Bio-Rad) was used and was equilibrated with 5 mM $H_2SO_4$ in water at 35° C., and samples were eluted with 5 mM $H_2SO_4$ in water at a flow rate of 0.6 mL/min. Data acquisition and control were performed using Waters Millennium software. Values are averaged from two independent samples. These results are shown in Table 2 and 3.

After 13 hours of cultivation in defined medium, transformants 246-27 and 247-11 harboring the *L. helveticus* LDH gene produced 0.1–0.4 g/L lactic acid; 1.8–3.9 g/L lactic acid was produced after 19 hours.

After 13 hours of cultivation in defined medium, transformants 265-03, 265-06, 265-11, 265-12, 265-18, 265-29, 265-44, 265-45, 265-46, 265-52, 265-55 and 265-57 harboring the *B. megaterium* LDH gene integrated in an unknown site in the genome in one copy produced 0.5–1.9 g/L lactic acid; 4.0–6.3 g/L lactic acid were produced after 19 hours.

After 13 hours of cultivation in defined medium, transformants 265-14, 265-22 and 265-23 harboring two copies of the *B. megaterium* LDH gene integrated in an unknown site in the genome produced 0.5–1.2 g/L lactic acid; 3.8–6.1 g/L lactic acid were produced after 19 hours.

After 13 hours of cultivation in defined medium, transformant 265-56 harboring three copies of the *B. megaterium* LDH gene produced 0.7 g/L lactic acid; 5.2 g/L lactic acid were produced after 19 hours.

After 13 hours of cultivation in defined medium, transformants 265-05, 265-07, 265-15, 265-17, 265-33, 265-34, 265-35, 265-38, 265-39, 265-42, 265-43, 265-47, 265-48, 265-49, 265-51 and 265-60 harboring the *B. megaterium* LDH gene integrated into the pdc1 gene locus pdc1-genotype) produced 0.4–2.7 g/L lactic acid; 3.4–7.5 g/L lactic acid were produced after 19 hours.

After 12 hours cultivation in rich medium, transformants 246-27 and 247-11 harboring the *L. helveticus* LDH gene produced 0.5–1.7 g/L lactic acid, and produced 3.7–6.1 g/L lactic acid after 17 hours. In comparison, the host strain produced 0.1 g/L lactic acid after 17 hours of cultivation.

After 12 hours cultivation in rich medium, the transformants 265-03, 265-06, 265-11, 265-12, 265-18, 265-29, 265-44, 265-45, 265-46, 265-52, 265-55 and 265-57 harboring the *B. megaterium* LDH gene produced 1.4–4.3 g/L lactic acid, and produced 7.2–9.8 g/L lactic acid after 17 hours.

After 12 hours of cultivation in rich medium, transformants 265-14, 265-22 and 265-23 harboring two copies of the *B. megaterium* LDH gene produced 2.1–1.9 g/L lactic acid, and produced 6.3–6.8 g/L lactic acid after 17 hours.

After 12 hours of cultivation in rich medium, transformant 265-56 harboring three copies of the *B. megaterium* LDH gene produced 2.6 g/L lactic acid, and produced 7.5 g/L lactic acid after 17 hours.

After 12 hours of cultivation in rich medium, the transformants 265-05, 265-07, 265-15, 265-17, 265-33, 265-34, 265-35, 265-38, 265-39, 265-42, 265-43, 265-47, 265-48, 265-49, 265-51 and 265-60 harboring the *B. megaterium* LDH gene integrated into the pdc1 gene locus (pdc1-genotype) produced 2.0–4.7 g/L lactic acid, and produced 7.1–10.7 g/L lactic acid after 17 hours.

These results show that the LDH transformants produced lactic acid when the host strain did not. *B. megaterium* and *L. helveticus* LDHs were shown to be active in *C. sonorensis*. These heterologous LDHs can thus effectively compete for pyruvate in the presence of PDC. The pdc1 deletion did not seem to have an effect on the overall yield and production of lactate. Residual glucose was higher and ethanol concentration was lower in transformants containing two (265-14, 265-22, 265-23) or three (265-56) copies A higher LDH copy number also resulted in a higher lactic acid yield from glucose, less ethanol production, and a higher ratio of lactic acid to ethanol. The biomass ($OD_{600}$) increased less in strains containing more than one copy of *B. megaterium* LDH.

TABLE 2

$OD_{600}$, residual glucose, lactic acid and ethanol production of *C. sonorensis* and LDH transformants on defined medium.

| Strain | $OD_{600}$ 13 h | $OD_{600}$ 19 h | Glucose 13 h | Glucose 19 h | Lactic acid 13 h | Lactic acid 19 h | Ethanol 13 h | Ethanol 19 h |
|---|---|---|---|---|---|---|---|---|
| *C. sonorensis* | 1.87 | 7.54 | 16.24 | 5.53 | 0.00 | 0.00 | 0.83 | 4.08 |
| 246-27 | 1.04 | 6.33 | 18.66 | 8.06 | 0.40 | 3.93 | 0.06 | 1.70 |
| 247-11 | 0.43 | 4.08 | 19.91 | 14.26 | 0.08 | 1.78 | 0.00 | 0.73 |
| 265-03 | 2.45 | 7.45 | 15.54 | 3.17 | 1.22 | 6.01 | 0.60 | 2.97 |
| 265-06 | 2.93 | 7.22 | 15.69 | 3.18 | 1.34 | 6.02 | 0.52 | 2.94 |
| 265-11 | 2.66 | 7.48 | 15.63 | 3.24 | 1.33 | 6.09 | 0.48 | 2.87 |
| 265-12 | 3.58 | 7.04 | 17.28 | 5.60 | 0.86 | 4.96 | 0.27 | 2.37 |
| 265-18 | 2.03 | 6.82 | 18.15 | 7.66 | 0.56 | 4.00 | 0.24 | 2.22 |
| 265-44 | 2.52 | 7.52 | 17.74 | 5.65 | 0.86 | 4.86 | 0.22 | 2.38 |
| 265-45 | 2.04 | 5.20 | 18.96 | 7.85 | 0.53 | 4.07 | 0.11 | 1.89 |
| 265-46 | 2.96 | 6.96 | 16.05 | 2.65 | 1.23 | 6.06 | 0.55 | 3.05 |
| 265-52 | 1.94 | 7.11 | 18.54 | 7.32 | 0.59 | 4.18 | 0.23 | 1.99 |
| 265-55 | 3.22 | 7.67 | 15.71 | 2.86 | 1.63 | 6.28 | 0.64 | 2.86 |
| 265-57 | 2.03 | 7.12 | 18.37 | 7.58 | 0.66 | 3.96 | 0.28 | 2.01 |
| 265-29 | 3.27 | 7.11 | 14.59 | 2.78 | 1.93 | 6.30 | 0.71 | 2.85 |
| 265-14 | 1.65 | 5.84 | 19.05 | 10.42 | 0.45 | 3.75 | 0.05 | 1.06 |
| 265-22 | 1.94 | 6.33 | 18.33 | 8.10 | 0.67 | 5.10 | 0.11 | 1.37 |
| 265-23 | 2.52 | 6.76 | 16.95 | 6.01 | 1.23 | 6.14 | 0.23 | 1.62 |
| 265-56 | 1.86 | 5.81 | 19.14 | 10.26 | 0.65 | 5.22 | 0.00 | 0.56 |
| 265-05 | 2.19 | 7.01 | 16.38 | 4.95 | 0.99 | 4.80 | 0.46 | 2.59 |

TABLE 2-continued

OD$_{600}$, residual glucose, lactic acid and ethanol production of
C. sonorensis and LDH transformants on defined medium.

| Strain | OD$_{600}$ 13 h | OD$_{600}$ 19 h | Glucose 13 h | Glucose 19 h | Lactic acid 13 h | Lactic acid 19 h | Ethanol 13 h | Ethanol 19 h |
|---|---|---|---|---|---|---|---|---|
| 265-07 | 2.54 | 7.25 | 16.35 | 4.35 | 1.18 | 5.32 | 0.43 | 2.78 |
| 265-15 | 2.82 | 7.47 | 15.63 | 3.09 | 1.38 | 5.70 | 0.62 | 3.09 |
| 265-17 | 1.79 | 6.41 | 18.88 | 8.66 | 0.39 | 3.50 | 0.06 | 1.86 |
| 265-33 | 3.85 | 7.89 | 13.67 | 1.74 | 2.17 | 6.53 | 0.96 | 3.55 |
| 265-34 | 3.96 | 7.85 | 12.52 | 0.15 | 2.74 | 7.50 | 1.19 | 3.51 |
| 265-35 | 2.71 | 7.58 | 16.89 | 4.82 | 0.98 | 4.84 | 0.36 | 2.68 |
| 265-38 | 2.66 | 8.20 | 17.01 | 4.56 | 1.02 | 5.25 | 0.36 | 2.80 |
| 265-39 | 2.38 | 7.71 | 17.57 | 5.76 | 0.73 | 4.63 | 0.28 | 2.45 |
| 265-42 | 2.64 | 7.50 | 17.28 | 5.34 | 0.97 | 4.98 | 0.35 | 2.44 |
| 265-43 | 1.81 | 6.79 | 18.86 | 8.94 | 0.51 | 3.44 | 0.11 | 1.78 |
| 265-47 | 2.71 | 7.41 | 17.09 | 4.30 | 0.99 | 5.18 | 0.38 | 2.68 |
| 265-48 | 2.90 | 7.66 | 16.66 | 3.86 | 1.14 | 5.47 | 0.45 | 2.81 |
| 265-49 | 2.73 | 7.42 | 16.57 | 4.07 | 1.18 | 5.26 | 0.41 | 2.67 |
| 265-51 | 2.71 | 7.66 | 16.91 | 4.06 | 1.14 | 5.35 | 0.37 | 2.71 |
| 265-60 | 2.41 | 7.71 | 17.50 | 5.54 | 0.85 | 4.63 | 0.35 | 2.48 |

Glucose, lactic acid, and ethanol concentrations in g/L

TABLE 3

OD$_{600}$, residual glucose, lactic acid, and ethanol production of
C. sonorensis and LDH transformants on rich medium.

| Strain | OD$_{600}$ 12 h | OD$_{600}$ 17 h | Glucose 12 h | Glucose 17 h | Lactic acid 12 h | Lactic acid 17 h | Ethanol 12 h | Ethanol 17 h |
|---|---|---|---|---|---|---|---|---|
| C. sonorensis | 3.78 | 13.28 | 41.37 | 22.86 | 0.00 | 0.09 | 1.90 | 10.05 |
| 246-27 | 3.10 | 7.33 | 43.81 | 32.49 | 1.68 | 6.12 | 0.63 | 3.27 |
| 247-11 | 2.13 | 5.60 | 46.38 | 38.36 | 0.52 | 3.70 | 0.11 | 2.18 |
| 265-03 | 3.63 | 8.53 | 41.70 | 28.49 | 2.07 | 7.29 | 0.95 | 4.53 |
| 265-06 | 4.13 | 9.25 | 41.76 | 26.30 | 2.75 | 7.99 | 1.32 | 5.28 |
| 265-11 | 4.08 | 9.15 | 42.47 | 28.34 | 2.27 | 7.39 | 0.98 | 4.97 |
| 265-12 | 4.55 | 9.98 | 40.67 | 25.05 | 2.81 | 8.66 | 1.55 | 5.40 |
| 265-18 | 4.73 | 10.38 | 40.85 | 23.97 | 2.61 | 8.45 | 1.53 | 5.72 |
| 265-44 | 5.35 | 10.30 | 40.09 | 23.76 | 3.60 | 9.20 | 1.82 | 6.00 |
| 265-45 | 4.68 | 9.90 | 41.41 | 26.30 | 2.55 | 8.31 | 1.37 | 5.88 |
| 265-46 | 4.43 | 10.05 | 41.66 | 27.31 | 2.33 | 7.64 | 1.26 | 5.13 |
| 265-52 | 4.10 | 9.38 | 43.35 | 29.35 | 2.48 | 7.24 | 1.01 | 4.53 |
| 265-55 | 4.80 | 9.30 | 41.63 | 29.37 | 2.92 | 8.26 | 1.13 | 4.67 |
| 265-57 | 6.28 | 11.25 | 38.24 | 21.19 | 4.30 | 9.79 | 2.25 | 6.83 |
| 265-29 | 5.20 | 9.80 | 20.87 | 23.78 | 3.67 | 9.27 | 1.69 | 5.90 |
| 265-14 | 3.25 | 6.70 | 44.57 | 34.95 | 1.57 | 6.79 | 0.33 | 2.25 |
| 265-22 | 3.25 | 6.75 | 44.27 | 34.50 | 1.49 | 6.31 | 0.31 | 2.38 |
| 265-23 | 3.15 | 6.73 | 41.97 | 33.79 | 1.89 | 6.80 | 0.42 | 2.27 |
| 265-56 | 4.25 | 8.18 | 44.51 | 33.82 | 2.57 | 7.45 | 0.58 | 2.57 |
| 265-05 | 4.75 | 10.85 | 39.74 | 23.43 | 3.02 | 8.50 | 1.73 | 6.21 |
| 265-07 | 4.15 | 10.05 | 41.68 | 26.04 | 2.26 | 7.86 | 1.36 | 5.46 |
| 265-15 | 5.05 | 9.98 | 39.47 | 22.92 | 2.77 | 8.83 | 1.84 | 6.56 |
| 265-17 | 4.53 | 10.10 | 40.66 | 24.61 | 2.75 | 7.76 | 1.38 | 5.87 |
| 265-33 | 4.63 | 10.28 | 41.42 | 24.33 | 2.42 | 8.01 | 1.40 | 5.94 |
| 265-34 | 5.00 | 9.93 | 39.60 | 24.99 | 3.09 | 8.63 | 1.75 | 5.44 |
| 265-35 | 5.73 | 11.33 | 36.08 | 19.29 | 4.74 | 10.66 | 2.94 | 7.24 |
| 265-38 | 4.98 | 10.45 | 40.58 | 25.53 | 2.64 | 7.99 | 1.42 | 5.65 |
| 265-39 | 4.33 | 10.45 | 41.49 | 27.30 | 2.41 | 7.79 | 1.24 | 5.08 |
| 265-42 | 6.08 | 11.15 | 37.74 | 21.15 | 4.37 | 9.68 | 2.32 | 6.79 |
| 265-43 | 4.23 | 9.60 | 41.10 | 29.83 | 2.02 | 7.20 | 0.90 | 4.61 |
| 265-47 | 4.08 | 9.43 | 42.66 | 28.06 | 2.32 | 7.40 | 1.18 | 5.12 |
| 265-48 | 4.43 | 10.23 | 42.48 | 27.89 | 2.28 | 7.10 | 1.27 | 5.00 |
| 265-49 | 5.20 | 10.20 | 39.29 | 25.17 | 3.18 | 8.55 | 1.86 | 5.94 |
| 265-51 | 4.48 | 10.15 | 42.28 | 26.89 | 2.34 | 7.72 | 1.30 | 5.60 |
| 265-60 | 4.38 | 9.45 | 42.56 | 28.13 | 2.41 | 7.66 | 1.13 | 5.11 |

Glucose, lactic acid, and ethanol concentrations in g/L.

Example 15

Production of L-lactic Acid in Defined or Rich Glucose Medium in Aerobic Test Tube Cultures by C. sonorensis Harboring L. helveticus, B. megaterium or R. oryzae LDH Gene Integrated into the Genome C. sonorensis cells and the transformants disclosed above (namely, 246-27, 247-11, 265-39, 265-5, 265-15, 265-44, 266-1, 266-2, 266-4, 266-6, 266-7, 266-8, 266-11, 278-2, 278-3, 278-4, 278-6, 278-7, 278-8, 278-9, 278-11, 278-12, 278-13, 278-14, 278-15, 278-17, 278-18, 278-19, 278-20, 257-3, 257-5, 257-6, 257-8, 257-8, 257-9, 257-10, 257-11, and 257-12) were cultivated in YPD (YP supplemented with 5% glucose and 0.5 M MES pH 5.5) or YD-medium (yeast nitrogen base without amino acids supplemented with 2% glucose and 0.5 M MES pH 5.5). A colony from each transformant was inoculated into a 14 mL disposable plastic tube containing 5 mL of YPD or YD medium and cultivated with 250 rpm shaking at 30° C. Samples were withdrawn during cultivation at time points 12 and 17 hours, $OD_{600}$ measured, and cells harvested by centrifugation and the culture supernatant analyzed by HPLC as described above for lactic acid, glucose and ethanol. HPLC analyses were carried out as detailed above in Example 14. These results are shown in Tables 4 and 5.

After 12 hours of cultivation in defined medium, transformants harboring the L. helveticus LDH gene produced 0.1–0.7 g/L lactic acid. In rich medium 0.9–2.7 g/L lactic acid was produced by these cells.

After 12 hours of cultivation in defined medium, transformants harboring the B. megaterium LDH gene produced 0.1–0.5 g/L lactic acid. In rich medium 1.9–3.2 g/L lactic acid was produced by these cells.

After 12 hours of cultivation in defined medium, transformants harboring the R. oryzae LDH gene produced 0.2–0.6 g/L lactic acid. In rich medium 0.9–2.7 g/L lactic acid was produced by these cells.

After 12 hours of cultivation in defined medium, transformants harboring both the R. oryzae LDH gene integrated into pdc1 gene locus and the B. megaterium LDH gene produced 0.1–0.9 g/L lactic acid. In rich medium 1.0–3.3 g/L lactic acid was produced by these cells.

After 17 hours of cultivation in defined medium, transformants harboring the L. helveticus LDH gene produced 0.9–2.1 g/L lactic acid. In rich medium 6.6–9.9 g/L lactic acid was produced by these cells.

After 17 hours of cultivation in defined medium, transformants harboring the B. megaterium LDH gene produced 0.8–1.7 g/L lactic acid. In rich medium 8.7–11.0 g/L lactic acid was produced by these cells.

After 17 hours of cultivation in defined medium, transformants harboring the R. oryzae LDH gene produced 0.7–1.3 g/L lactic acid. In rich medium 7.3–9.5 g/L lactic acid was produced by these cells.

After 17 hours of cultivation in defined medium, transformants harboring both the R. oryzae LDH gene integrated into pdc1 gene locus and the B. megaterium LDH gene produced 0.7–3.0 g/L lactic acid. In rich medium 5.0–10.7 g/L lactic acid was produced by these cells.

These results showed that all three heterologous LDHs were active in C. sonorensis and could be used for producing lactic acid. These LDHs can effectively compete for pyruvate in the presence of PDC. Expression of any of these LDH genes reduced glucose utilization, growth and ethanol production, especially in rich medium. The reduction in glucose utilization rate and growth were strongest in strains containing L. helveticus LDH and mildest in strains containing R. oryzae LDH, while B. megaterium LDH transformants showed intermediate behavior. The effects were masked by the presence of the B. megaterium LDH in the transformants containing LDHs of two origins.

TABLE 4

$OD_{600}$, residual glucose, lactic acid, and ethanol production of C. sonorensis and LDH transformants on defined medium.

| Strain | $OD_{600}$ 12 h | $OD_{600}$ 17 h | Glucose 12 h | Glucose 17 h | Lactic acid 12 h | Lactic acid 17 h | Ethanol 12 h | Ethanol 17 h |
|---|---|---|---|---|---|---|---|---|
| C. sonorensis | 3.78 | 7.65 | 15.07 | 6.86 | 0.00 | 0.00 | 1.16 | 3.20 |
| 246-27 | 1.56 | 4.95 | 19.10 | 13.41 | 0.22 | 0.99 | 0.00 | 1.02 |
| 247-11 | 2.16 | 5.35 | 17.82 | 10.40 | 0.43 | 1.40 | 0.22 | 1.59 |
| 265-39 | 2.30 | 6.05 | 17.88 | 10.08 | 0.45 | 1.73 | 0.28 | 1.78 |
| 265-5 | 1.04 | 3.85 | 19.96 | 14.50 | 0.13 | 0.83 | 0.00 | 0.82 |
| 265-15 | 1.68 | 5.20 | 18.40 | 11.45 | 0.33 | 1.45 | 0.11 | 1.46 |
| 265-44 | 1.62 | 5.00 | 18.38 | 12.55 | 0.27 | 1.36 | 0.09 | 1.62 |
| 266-1 | 3.22 | 7.80 | 15.68 | 6.68 | 0.48 | 1.27 | 0.87 | 2.93 |
| 266-2 | 3.52 | 7.75 | 15.49 | 7.42 | 0.60 | 1.19 | 0.82 | 2.65 |
| 266-3 | 1.80 | 6.55 | 18.07 | 10.53 | 0.22 | 0.71 | 0.28 | 1.95 |
| 266-4 | 2.58 | 7.00 | 17.10 | 9.00 | 0.33 | 1.00 | 0.48 | 2.83 |
| 266-7 | 2.84 | 7.95 | 16.38 | 7.50 | 0.43 | 1.32 | 0.67 | 2.66 |
| 266-8 | 1.96 | 6.45 | 17.77 | 10.30 | 0.28 | 1.20 | 0.35 | 2.08 |
| 266-11 | 3.00 | 7.50 | 15.64 | 7.14 | 0.47 | 1.28 | 0.82 | 2.87 |
| 278-2 | 1.78 | 5.25 | 18.31 | 11.97 | 0.40 | 2.27 | 0.10 | 1.17 |
| 278-3 | 1.62 | 4.35 | 18.52 | 13.85 | 0.29 | 1.17 | 0.00 | 0.86 |
| 278-4 | 1.72 | 5.00 | 18.43 | 12.63 | 0.40 | 1.89 | 0.00 | 0.94 |
| 278-6 | 2.24 | 6.10 | 17.59 | 10.39 | 0.45 | 1.57 | 0.25 | 1.74 |
| 278-7 | 1.98 | 5.80 | 17.70 | 11.00 | 0.41 | 1.65 | 0.21 | 1.56 |
| 278-8 | 2.76 | 6.45 | 15.96 | 8.65 | 0.89 | 2.55 | 0.46 | 2.27 |
| 278-9 | 1.78 | 4.35 | 18.21 | 13.43 | 0.26 | 0.90 | 0.00 | 0.92 |
| 278-11 | 2.80 | 6.80 | 16.02 | 8.83 | 0.53 | 2.36 | 0.54 | 2.13 |
| 278-12 | 1.96 | 5.80 | 17.31 | 10.71 | 0.36 | 1.31 | 0.18 | 1.57 |
| 278-13 | 2.30 | 6.25 | 17.01 | 9.22 | 0.51 | 1.97 | 0.29 | 1.99 |
| 278-14 | 1.84 | 5.65 | 17.77 | 10.69 | 0.50 | 2.11 | 0.12 | 1.46 |
| 278-15 | 1.46 | 4.00 | 18.78 | 14.66 | 0.25 | 1.03 | 0.00 | 0.52 |

TABLE 4-continued

OD$_{600}$, residual glucose, lactic acid, and ethanol production of
C. sonorensis and LDH transformants on defined medium.

| Strain | OD$_{600}$ 12 h | OD$_{600}$ 17 h | Glucose 12 h | Glucose 17 h | Lactic acid 12 h | Lactic acid 17 h | Ethanol 12 h | Ethanol 17 h |
|---|---|---|---|---|---|---|---|---|
| 278-17 | 2.38 | 6.60 | 16.92 | 8.60 | 0.63 | 2.01 | 0.37 | 2.05 |
| 278-18 | 2.26 | 5.75 | 17.44 | 10.27 | 0.70 | 3.02 | 0.16 | 1.65 |
| 278-19 | 2.62 | 6.60 | 16.87 | 9.06 | 0.54 | 1.69 | 0.35 | 2.01 |
| 278-20 | 1.34 | 3.75 | 19.17 | 15.66 | 0.14 | 0.70 | 0.00 | 0.34 |
| 257-3 | 2.20 | 5.60 | 17.62 | 10.57 | 0.45 | 1.45 | 0.24 | 1.69 |
| 257-5 | 2.44 | 6.35 | 17.55 | 10.38 | 0.45 | 1.62 | 0.25 | 2.15 |
| 257-6 | 2.10 | 5.70 | 17.88 | 10.58 | 0.72 | 2.12 | 0.12 | 1.34 |
| 257-8 | 1.58 | 4.50 | 18.70 | 13.21 | 0.31 | 1.64 | 0.00 | 1.03 |
| 257-9 | 1.34 | 4.60 | 19.56 | 13.93 | 0.14 | 0.86 | 0.00 | 0.98 |
| 257-10 | 2.88 | 6.90 | 16.22 | 8.18 | 0.67 | 1.60 | 0.52 | 2.39 |
| 257-11 | 1.24 | 4.05 | 19.64 | 14.99 | 0.10 | 0.98 | 0.00 | 0.94 |
| 257-12 | 2.16 | 6.10 | 17.74 | 10.53 | 0.39 | 1.46 | 0.23 | 1.73 |

Glucose, lactic acid and ethanol concentrations in g/L.

TABLE 5

OD$_{600}$, residual glucose, lactic acid, and ethanol production of
C. sonorensis and LDH transformants on rich medium.

| Strain | OD$_{600}$ 12 h | OD$_{600}$ 17 h | Glucose 12 h | Glucose 17 h | Lactic acid 12 h | Lactic acid 17 h | Ethanol 12 h | Ethanol 17 h |
|---|---|---|---|---|---|---|---|---|
| C. sonorensis | 8.36 | 18.20 | 37.48 | 11.41 | 0.29 | 0.34 | 4.06 | 14.58 |
| 246-27 | 2.50 | 7.75 | 45.77 | 32.83 | 1.09 | 6.94 | 0.60 | 3.40 |
| 247-11 | 3.76 | 8.50 | 42.59 | 29.53 | 2.36 | 9.39 | 1.18 | 4.53 |
| 265-39 | 5.76 | 11.05 | 38.25 | 18.56 | 3.22 | 10.97 | 2.57 | 7.65 |
| 265-5 | 4.20 | 10.85 | 42.29 | 23.69 | 2.04 | 9.03 | 1.53 | 6.42 |
| 265-15 | 4.82 | 10.65 | 41.50 | 22.52 | 2.09 | 9.67 | 1.88 | 7.38 |
| 265-44 | 3.98 | 9.80 | 42.74 | 25.44 | 1.91 | 8.73 | 1.49 | 6.07 |
| 266-1 | 7.34 | 15.95 | 35.67 | 5.47 | 2.49 | 8.13 | 3.99 | 14.28 |
| 266-2 | 6.12 | 15.45 | 38.62 | 11.72 | 2.15 | 7.79 | 2.96 | 11.97 |
| 266-3 | 6.74 | 16.65 | 38.31 | 9.83 | 2.03 | 7.38 | 3.19 | 12.88 |
| 266-4 | 10.18 | 16.55 | 27.26 | 0.00 | 4.11 | 9.53 | 6.72 | 16.93 |
| 266-7 | 7.72 | 16.05 | 34.83 | 4.54 | 2.79 | 8.49 | 4.56 | 14.76 |
| 266-8 | 7.16 | 16.60 | 36.67 | 6.56 | 2.34 | 7.93 | 4.03 | 14.27 |
| 266-11 | 6.30 | 16.15 | 38.99 | 10.97 | 1.90 | 7.34 | 2.95 | 13.06 |
| 278-2 | 4.40 | 9.90 | 42.30 | 28.67 | 2.42 | 9.24 | 1.29 | 5.40 |
| 278-3 | 3.70 | 8.75 | 42.95 | 27.58 | 1.59 | 7.45 | 1.41 | 5.71 |
| 278-4 | 3.88 | 9.30 | 43.39 | 27.92 | 2.11 | 7.60 | 1.06 | 4.86 |
| 278-6 | 3.84 | 10.20 | 43.69 | 24.57 | 1.60 | 8.22 | 1.21 | 6.34 |
| 278-7 | 4.44 | 11.10 | 41.90 | 23.21 | 2.16 | 8.64 | 1.62 | 7.79 |
| 278-8 | 4.56 | 10.90 | 40.59 | 23.41 | 2.59 | 10.06 | 1.67 | 6.92 |
| 278-9 | 3.76 | 8.25 | 43.22 | 27.87 | 1.71 | 7.31 | 1.46 | 5.64 |
| 278-11 | 4.70 | 12.65 | 41.29 | 19.13 | 2.00 | 7.60 | 1.97 | 8.58 |
| 278-12 | 4.64 | 10.70 | 41.99 | 23.98 | 1.85 | 9.43 | 1.54 | 7.13 |
| 278-13 | 5.90 | 10.80 | 38.64 | 18.92 | 3.20 | 10.74 | 2.34 | 8.20 |
| 278-14 | 4.22 | 8.05 | 42.35 | 30.46 | 3.23 | 9.77 | 1.38 | 3.31 |
| 278-15 | 2.94 | 5.40 | 44.64 | 35.52 | 1.84 | 6.61 | 0.60 | 2.24 |
| 278-17 | 5.22 | 10.45 | 39.23 | 19.69 | 3.28 | 10.51 | 2.61 | 7.65 |
| 278-18 | 2.48 | 5.30 | 46.55 | 37.17 | 1.04 | 5.01 | 0.63 | 2.56 |
| 278-19 | 4.64 | 11.10 | 41.03 | 21.87 | 2.52 | 10.17 | 2.00 | 7.47 |
| 278-20 | 3.22 | 7.90 | 44.53 | 30.92 | 1.59 | 6.55 | 1.10 | 3.38 |
| 257-3 | 3.74 | 7.95 | 43.93 | 29.12 | 1.97 | 8.75 | 1.02 | 4.21 |
| 257-5 | 3.86 | 8.45 | 43.67 | 28.38 | 2.19 | 8.96 | 1.24 | 4.51 |
| 257-6 | 3.06 | 6.00 | 45.26 | 36.88 | 1.90 | 8.03 | 0.50 | 1.63 |
| 257-8 | 3.42 | 6.20 | 44.21 | 34.58 | 2.67 | 8.18 | 0.57 | 1.98 |
| 257-9 | 4.02 | 8.20 | 43.16 | 28.31 | 2.24 | 9.16 | 1.22 | 4.41 |
| 257-10 | 4.60 | 10.00 | 42.66 | 25.14 | 2.09 | 9.69 | 1.54 | 5.36 |
| 257-11 | 2.70 | 8.00 | 45.80 | 33.33 | 0.85 | 6.57 | 0.49 | 3.45 |
| 257-12 | 4.48 | 9.60 | 42.09 | 26.58 | 2.40 | 9.91 | 1.47 | 4.55 |

Glucose, lactic acid and ethanol concentrations in g/L.

Example 16

Production of L-lactic Acid in Defined Glucose Medium with or without Buffering in Microaerobic Shake Flask Cultures by C. sonorensis Harboring B. megaterium or R. oryzae LDH Gene Integrated into the Genome The C. sonorensis transformants harboring the B. megaterium LDH gene (namely 265-23 and 265-55) or the R. oryzae LDH gene (266-8) were cultivated in defined glucose medium. Precultures were grown in YD medium (yeast nitrogen base without amino acids supplemented with 5% glucose and 0.5 M MES pH 5.5), cells collected by centrifugation and resuspended in 50 mL of YD medium (yeast nitrogen base without amino acids supplemented with 10% glucose) to an $OD_{600}$ of 15 for the cultivation experiments. Yeasts were cultivated in 250 mL Erlenmeyer flasks with or without 4 g $CaCO_3$ with 100 rpm shaking at 30° C. Samples were withdrawn during cultivation, $OD_{600}$ measured from the cultures without $CaCO_3$, and cells harvested by centrifugation and the culture supernatant analyzed for L-lactic acid (by the L-lactic acid UV method of Boehringer Mannheim, Roche) and glucose (by the glucose/GOD-Perid method of Boehringer Mannheim, Roche). These results are shown in Table 6.

After 24 hours of cultivation, transformant 265-55 harboring B. megaterium LDH gene produced 35.7 g/L lactic acid with $CaCO_3$ buffering and 6.16 g/L lactic acid without buffering when the pH dropped to 2.75. Transformant 265-23 harboring two copies of B. megaterium LDH gene produced 38.2 g/L lactic acid with $CaCO_3$ buffering and 6.81 g/L lactic acid without buffering when the pH dropped to 2.68 (24 hours of cultivation). Transformant 266-8 harboring R. oryzae LDH gene produced 35.4 g/L lactic acid with $CaCO_3$ buffering and 3.05 g/L lactic acid without buffering when the pH dropped to 2.83 (24 hours of cultivation).

These results demonstrated that in the presence of $CaCO_3$ at pH 6.5, lactic acid production and glucose utilization were higher than in unbuffered conditions below pH 3. Higher lactic acid titers were reached in the presence of $CaCO_3$.

TABLE 6

$OD_{600}$, residual glucose (g/L), and lactic acid (g/L) production of LDH transformants on defined medium. "C" indicates the presence of $CaCO_3$ in the cultivation.

| Strains | 0 h | 4 h | 8 h | 12 h | 24 h |
|---|---|---|---|---|---|
| 265-55, $OD_{600}$ | 16.1 | 15.7 | 14.1 | 13.1 | 12.2 |
| 265-23, $OD_{600}$ | 15.9 | 14.6 | 12.6 | 10.2 | 12.3 |
| 266-8, $OD_{600}$ | 17.6 | 17.4 | 14.9 | 13.0 | 14.5 |
| 265-55 C, $OD_{600}$ | 17.4 | n.d. | n.d. | n.d. | n.d. |
| 265-23 C, $OD_{600}$ | 14.0 | n.d. | n.d. | n.d. | n.d. |
| 266-8 C, $OD_{600}$ | 17.7 | n.d. | n.d. | n.d. | n.d. |
| 265-55, glucose g/L | 125.4 | 105.1 | 99.08 | 99.52 | 85.01 |
| 265-23, glucose g/L | 109.4 | 100.8 | 92.16 | 77.31 | 70.93 |
| 266-8, glucose g/L | 109.8 | 81.27 | 87.98 | 62.02 | 51.11 |
| 265-55 C, glucose g/L | 106.6 | 91.94 | 93.03 | 78.08 | 49.83 |
| 265-23 C, glucose g/L | 86.66 | 110.6 | 73.13 | 75.00 | 46.56 |
| 266-8 C, glucose g/L | 105.1 | 101.0 | 73.13 | 75.66 | 41.48 |
| 265-55, lactic acid g/L | 0.67 | 3.35 | 4.33 | 5.58 | 6.16 |
| 265-23, lactic acid g/L | 0.69 | 3.52 | 4.53 | 5.76 | 6.81 |
| 266-8, lactic acid g/L | 0.67 | 3.43 | 4.58 | 4.22 | 3.05 |
| 265-55 C, lactic acid g/L | 0.57 | 6.92 | 12.21 | 18.73 | 35.73 |
| 265-23 C, lactic acid g/L | 0.64 | 7.26 | 13.28 | 17.90 | 38.18 |
| 266-8 C, lactic acid g/L | 0.35 | 5.01 | 10.36 | 15.76 | 35.36 |

Example 17

Intracellular Lactic Acid in $CaCO_3$-buffered and Unbuffered Cultivation

Cell pellets from C. sonorensis transformants harboring the B. megaterium LDH gene (namely 265-23 and 265-55) or the R. oryzae LDH gene (266-8) cultivated in defined glucose medium, as described above in Example 16, were analyzed to determine intracellular lactic acid concentration. Samples (2 mL) were withdrawn during cultivation at 8 h and 24 h, $OD_{600}$ measured and cells harvested by centrifugation. The supernatant was discarded and each of the pellets was washed with 1 mL of ice-cold 10 mM $K_2HPO_4$/$KH_2PO_4$, pH 7.5, supplemented with 2 mM EDTA. Washed cell pellets were resuspended in 0.5 mL of the same buffer and stored at −70° C. Samples were thawed and washed (1 mL) once in 1 M Tris-HCl, pH 9.0, and centrifuged at 13,000 rpm for 1 min. The pellet was suspended into 1 mL ice cold 5% trichloroacetic acid (TCA) and vortexed 1 min. After vortexing, the sample was kept on ice for about 30 min. After incubation on ice, the sample was vortexed for 1 min and centrifuged at 13,000 rpm for 30 min at 4° C. Lactic acid levels were measured in the collected supernatant. Lactic acid concentration was analyzed from the sample by using an enzymatic method (L-lactic acid UV method, Boehringer Mannheim, Roche) or by HPLC (as in Example 14). Intracellular concentration of lactic acid was calculated as follows:

1. The Intracellular Volume of the Cells (in the Sample):

Dry weight of the culture (g/L)*volume of the sample (L)*2 mL/g cell=cell volume (mL).

Cell volume is converted into liters by multiplying by 0.001. One gram of cell (dry weight) corresponds to 2 mL cell volume (Gancedo & Serrano, 1989, "Energy Yielding Metabolism," in The yeasts. (Rose & Harrison, eds.), Vol 3. Academic Press: London).

2. The Lactic Acid Amounts in the Cells:

Measured lactic acid concentration (g/L)*volume of used 5% TCA (L)=lactic acid amount (g) in the sample. To calculate lactic acid concentration in the cell: divide lactic acid amount in the sample (g) by cell volume (L).

After 24 hours of cultivation transformant 265-55 harboring the B. megaterium LDH gene had an intracellular concentration of 28.2 g/L lactic acid with $CaCO_3$ buffering and 7.2 g/L of lactic acid without buffering. Transformant 265-23 harboring two copies of the B. megaterium LDH gene had an intracellular concentration of 46.1 g/L lactic acid with $CaCO_3$ buffering and 8.2 g/L of lactic acid without buffering, after 24 hours of cultivation. Transformant 266-8 harboring R. oryzae LDH gene had an intracellular concentration of 45.4 g/L of lactic acid with $CaCO_3$ buffering and 4.9 g/L of lactic acid without buffering (24 hours cultivation). These results are shown in Table 7.

These results showed that after 8 h of cultivation intracellular lactic acid levels were twice as high as extracellular levels in transformants 265-55 and 265-23 when grown in unbuffered culture. At 8 h of cultivation for the other transformants, the difference between intra- and extracellular levels was small, about 10%. When $CaCO_3$ was included in the cultures, the intracellular and extracellular lactic acid levels in all strains were higher than cultures without $CaCO_3$. The intra- and extracellular lactic acid concentrations in all strains increased from 8 to 24 h in the $CaCO_3$-buffered culture. The intracellular lactic acid concentrations in the unbuffered cultures are similar at 8 h and at 24 h. The intracellular lactic acid levels of strain 266-8 are lower than the levels of the other strains.

TABLE 7

Intracellular lactic acid concentration (g/L). "C" indicates the presence of CaCO₃ in the cultivation.

| Transformant | 8 h | 24 h |
|---|---|---|
| 265-55 | 10.42 | 7.16 |
| 265-23 | 10.18 | 8.16 |
| 266-8 | 4.77 | 4.87 |
| 265-55 C | 11.38 | 28.15 |
| 265-23 C | 11.85 | 46.11 |
| 266-8 C | 8.53 | 45.40 |

Example 18

Enzyme Activities of Lactate Dehydrogenase and Pyruvate Decarboxylase in *C. sonorensis* Harboring *L. helveticus* or *B. megaterium* LDH Gene Integrated into the Genome The *C. sonorensis* transformants (namely, 246-27, 247-11, 257-3, 257-12, 257-6, 247-9, 246-27, 247-11, 265-39, 265-15, 265-44, 265-55, 265-23, 265-22, 265-56, 278-14, 278-17, 286-4, 286-30, and 286-1) were cultivated in 50 mL of YD-medium (yeast nitrogen base without amino acids supplemented with 5% glucose and 0.5 M MES pH 5.5), in 250 mL Erlenmeyer flasks with 250 rpm shaking to an $OD_{600}$ of 10 at 30° C. Cells were harvested by centrifugation and the culture supernatant was analyzed by HPLC. Cell samples to be used for enzyme activity measurements (2 mL) were collected by centrifugation and washed with 1 mL of ice-cold 10 mM $K_2HPO_4/KH_2PO_4$, pH 7.5 supplemented with 2 mM EDTA. Washed cell pellets were resuspended in 0.5 mL of the same buffer and stored at −70° C. Samples were thawed at room temperature and washed (1 mL) once in sonication buffer (100 mM $KH_2PO4/K_2HPO_4$, pH 7.5 supplemented with 2 mM $MgCl_2$ and 10 mM DTT). Washed samples were resuspended in 0.5 mL of sonication buffer and homogenized with 0.5 mL of glass beads with a Bead Beater homogenizer for 1 minute. After homogenization samples were centrifuged at 14,000 rpm for 30 min at 4° C. Supernatant samples were collected and lactate dehydrogenase activity was determined spectrophotometrically ($A_{340}$) with Cobas MIRA automated analyzer at 30° C. in sodium acetate buffer (50 mM Na-acetate pH 5.2) (*Lactobacillus helveticus* LDH) or in imidazole buffer (40 mM imidazole-HCl, pH 6.5) (*Bacillus megaterium* LDH) containing 0.4 mM NADH, 5 mM fructose-1,6-diphosphate, 1 mM glyoxylic acid and 2 mM pyruvate. The protein concentrations were determined by the Lowry method (Lowry et al., 1951, *J. Biol. Chem.* 193: 265–275). Bovine serum albumin (Sigma) was used as a protein standard. Pyruvate decarboxylase activity was determined spectrophotometrically ($A_{340}$) with Cobas MIRA automated analyzer at 30° C. in imidazole buffer (40 mM imidazole-HCl pH 6.5) containing 0.2 mM NADH, 50 mM $MgCl_2$, 0.2 mM thiamin pyrophosphate (cocarboxylase), 90 units of ADH and 50 mM pyruvate. 1 U of enzyme activity was defined as the amount of activity converting 1 μmol of NADH to $NAD^+$ per min. These results are shown in Table 8.

This Example demonstrated that intracellular LDH activity correlated with the copy number of the LDH genes in the genome. The calculated LDH activity in strains harboring one copy of the *L. helveticus* LDH was 8 U/mg total cellular protein, and the activity in strains harboring two copies was 15 or 35 U/mg total cellular protein. Lactic acid titers and yields from glucose were greater in the strains containing multiple copies of the LDH gene, however the ethanol titers were lower than in strains containing only one copy of the LDH gene. Calculated LDH activity in strains harboring one copy of the *B. megaterium* LDH was 2–3 U/mg total cellular protein, the activity in strains harboring 2 copies was 10 U/mg, and the activity in strains harboring 3 copies was 40 U/mg.

Pyruvate decarboxylase activity was typically 2–4 U/mg total cellular protein in strains containing an intact PDC2 gene. When pdc2 was disrupted, PDC activity dropped below 0.4 U/mg total cellular protein. If both pdc1 and pdc2 were deleted or disrupted (strain C44/286-10) PDC activity decreased to 0.07 U/mg total cellular protein.

TABLE 8

LDH and PDC enzyme activities; glucose, lactic acid, and ethanol concentrations; lactic acid yield in the culture supernatant measured from cultures grown on YD-medium. n.d.: not determined. 1x, 2x, and 3x indicate the LDH gene copy number.

| Strain | Genotype | LDH U/mg total cellular protein | PDC U/mg total cellular protein | Glucose g/L | Lactic acid g/L | Ethanol g/L | lactic acid yield (%) |
|---|---|---|---|---|---|---|---|
| 246-27 | 1xLhLDH, PDC+ | 8.01 | 3.82 | 31.8 | 4.73 | 2.63 | 26.00 |
| 247-11 | 1xLhLDH, PDC+ | 7.00 | 3.58 | 30.7 | 5.10 | 2.90 | 26.44 |
| 257-3 | 1xLhLDH, pdc1− | 8.70 | 3.81 | 29.6 | 5.76 | 2.96 | 28.25 |
| 257-12 | 1xLhLDH, pdc1− | 8.00 | 2.85 | 34.1 | 3.60 | 2.19 | 22.64 |
| 257-6 | 2xLhLDH, PDC+ | 15.0 | 3.73 | 34.1 | 5.79 | 1.31 | 36.51 |
| 247-9 | 2xLhLDH, PDC+ | 35.2 | 9.69 | 33.1 | 7.87 | 0.64 | 46.57 |
| 278-14 | 1xRo + 2xBmLDH, pdc1− | 5.99 | 3.59 | 28.6 | 5.50 | 3.37 | 25.71 |
| 278-17 | 1xRo + 1xBmLDH, pdc1− | 0.48 | 2.46 | 33.84 | 4.11 | 0.61 | 25.43 |
| 265-39 | 1xBmLDH, pdc1− | 2.73 | 2.89 | 31.99 | 7.03 | 1.82 | 39.03 |
| 265-15 | 1xBmLDH, pdc1− | 2.00 | 1.86 | 33 | 8.28 | 0.92 | 48.71 |
| 265-44 | 1xBmLDH, PDC+ | 3.48 | 3.42 | 33.33 | 7.89 | 1.02 | 47.33 |
| 265-55 | 1xBmLDH, PDC+ | 1.81 | 1.15 | 28.75 | 3.56 | 4.5 | 16.75 |

TABLE 8-continued

LDH and PDC enzyme activities; glucose, lactic acid, and ethanol
concentrations; lactic acid yield in the culture supernatant
measured from cultures grown on YD-medium. n.d.: not
determined. 1x, 2x, and 3x indicate the LDH gene copy number.

| Strain | Genotype | LDH U/mg total cellular protein | PDC U/mg total cellular protein | Glucose g/L | Lactic acid g/L | Ethanol g/L | lactic acid yield (%) |
|---|---|---|---|---|---|---|---|
| 265-23 | 2xBmLDH, PDC+ | 8.56 | 0.95 | 36.95 | 5.51 | 3.36 | 42.22 |
| 265-22 | 2xBmLDH, PDC+ | 11.1 | 2.37 | 28.97 | 7.13 | 2.45 | 33.90 |
| 265-56 | 3xBmLDH, PDC+ | 40.7 | 5.01 | 29.38 | 7.02 | 2.24 | 34.04 |
| 286-4 | 1xBmLDH, pdc2− | 0.43 | 0.22 | 34.6 | 3.13 | 0.59 | 20.32 |
| 286-30 | 1xBmLDH, pdc2− | 2.51 | 0.13 | 28.63 | 3.25 | 0.44 | 15.21 |
| 286-1 | 1xBmLDH, pdc2− | 3.28 | 0.35 | 28.71 | 3.5 | 0.48 | 16.44 |
| C44/ 286-10 | 2xBmLDH, pdc1−, pdc2− | 9.30 | 0.07 | n.d. | n.d. | n.d. | n.d. |

Example 19

Production of L-lactic Acid in Defined Glucose Medium by C. sonorensis Harboring the L. helveticus, B. megaterium or R. oryzae LDH Encoding Gene or Both B. megaterium and R. oryzae LDH Genes Integrated into the Genome C. sonorensis cells and the transformants (namely 266-7, 266-8, 246-27, 247-11, 257-3, 257-12, 257-6, 247-9, 265-39, 265-15, 265-44, 265-55, 265-23, 265-22, 265-56, 266-3, 278-14, 278-17, 286-4, 286-30, 286-1) were cultivated in YD medium (yeast nitrogen base without amino acids, pH 5.5, supplemented with 5% glucose and 0.5 M MES), and collected by centrifugation. The cells were resuspended in 50 mL of YD (yeast nitrogen base without amino acids supplemented with 10% glucose) to an $OD_{600}$ of 15 for the cultivation experiments. The cells were cultivated in 250 mL Erlenmeyer flasks containing 4 g $CaCO_3$ with 100 rpm shaking at 30° C. Samples were withdrawn during cultivation, the cells were harvested by centrifugation, and the growth medium was analyzed for lactic acid, glucose, and ethanol, by HPLC as described above (Example 14). These results are shown in Tables 9–13.

The maximal lactic acid titers in the culture supernatants were typically reached at 72 h or later in the cultivation after all glucose had been consumed. The maximal lactic acid titers and yields reached as classified on the basis of the different genetic backgrounds were as follows:

1 copy of R. oryzae LDH (strain 266-7): 81 g/L and 79% yield at 96 h
1 copy of B. megaterium LDH (strain 265-55): 85 g/L and 82% yield at 96 h
1 copy of L. helveticus LDH (strain 257-3): 85 g/L and 84% yield at 96 h
2 copies of B. megaterium LDH (strain 265-22): 87 g/L and 84% yield at 72 h
3 copies of B. megaterium LDH (strain 265-56): 83 g/L and 80% yield at 72 h
2 copies of L. helveticus LDH (strain 247-9): 90 g/L and 89% yield at 72 h
1 copy of R. oryzae LDH and 1 copy of B. megaterium LDH (strain 278-17): 79 g/L and 76% yield at 72 h
1 copy of R. oryzae LDH and 2 copies of B. megaterium LDH (strain 278-14): 89 g/L and 86% yield at 96 h After all glucose was consumed a calcium lactate precipitate was formed in the following cultures: strains 246-27, 247-11, 265-39, 265-15, 265-44, 265-23, 265-22, 278-14, 278-17, 286-4, 286-30, and 286-1. The precipitate formation also indicated that very high lactic acid titers were obtained.

These results demonstrated that C. sonorensis overexpressing L. helveticus, R. oryzae or B. megaterium LDH reached high final lactic acid titers (>80 g/L) and yields (>80%) from glucose in $CaCO_3$ buffered defined medium at pH 6.5. L. helveticus and B. megaterium LDH transformants performed essentially equally well, and better than R. oryzae LDH transformants that gave slightly lower lactic acid titers and yields. LDH copy number especially affected byproduct formation: a higher LDH copy number and LDH activity resulted in less ethanol and acetate production. Both L. helveticus and B. megaterium LDH transformants produced less ethanol and acetate than R. oryzae LDH transformants. Other measured byproducts, including glycerol and pyruvate were present in negligible amounts, and did not significantly differ between the PDC+, pdc1-or pdc2-genotypes.

TABLE 9

Maximal lactic acid titers and yields and ethanol and acetate production by C. sonorensis LDH transformants in $CaCO_3$ buffered cultivation on defined medium. 1x, 2x, and 3x indicate the LDH gene copy number.

| LDH genotype | Highest LA yield g/g used glucose | Highest LA titer g/L | EtOH g/L | acetate g/L | hrs | Ca-lactate ppte. | strain | PDC |
|---|---|---|---|---|---|---|---|---|
| 1xRoLDH | 0.76 | 79 | <0.02 | 2 | 120 | no | 266-3 | pdc1− |
| 1xRoLDH | 0.77 | 78 | 0.9 | 5 | 96 | no | 266-11 | pdc1− |

TABLE 9-continued

Maximal lactic acid titers and yields and ethanol and acetate production by *C. sonorensis* LDH transformants in CaCO₃ buffered cultivation on defined medium. 1x, 2x, and 3x indicate the LDH gene copy number.

| LDH genotype | Highest LA yield g/g used glucose | Highest LA titer g/L | EtOH g/L | acetate g/L | hrs | Ca-lactate ppte. | strain | PDC |
|---|---|---|---|---|---|---|---|---|
| 1xRoLDH | 0.78 | 81 | 0.4 | 4 | 96 | no | 266-7 | PDC+ |
| 1xRoLDH | 0.77 | 80 | 0.7 | 5 | 96 | no | 266-8 | PDC+ |
| 1xBmLDH | 0.82 | 85 | 0.0 | <0.01 | 72 | yes | 265-39 | pdc1− |
| 1xBmLDH | 0.82 | 85 | <0.02 | <0.01 | 72 | yes | 265-15 | pdc1− |
| 1xBmLDH | 0.80 | 83 | <0.02 | <0.01 | 72 | yes | 265-44 | PDC+ |
| 1xBmLDH | 0.82 | 85 | <0.02 | <0.01 | 96 | yes | 265-55 | PDC+ |
| 1xBmLDH | 0.77 | 80 | <0.02 | <0.01 | 72 | yes | 286-4 | pdc2− |
| 1xBmLDH | 0.77 | 80 | <0.02 | <0.01 | 72 | yes | 286-30 | pdc2− |
| 1xBmLDH | 0.73 | 76 | 0.2 | <0.01 | 48 | yes | 286-1 | pdc2− |
| 1xLhLDH | 0.79 | 80 | <0.02 | <0.01 | 120 | no | 246-27 | PDC+ |
| 1xLhLDH | 0.79 | 80 | <0.02 | <0.01 | 144 | no | 247-11 | PDC+ |
| 1xLhLDH | 0.84 | 85 | <0.02 | <0.01 | 96 | no | 257-3 | pdc1− |
| 1xLhLDH | 0.81 | 82 | <0.02 | <0.01 | 144 | no | 257-12 | pdc1− |
| 1xLhLDH | 0.81 | 84 | <0.02 | <0.01 | 72 | yes | 246-27 | PDC+ |
| 1xLhLDH | 0.82 | 85 | <0.02 | <0.01 | 72 | yes | 247-11 | PDC+ |
| 2xBmLDH | 0.80 | 83 | <0.02 | <0.01 | 72 | yes | 265-23 | PDC+ |
| 2xBmLDH | 0.84 | 87 | <0.02 | <0.01 | 72 | yes | 265-22 | PDC+ |
| 3xBmLDH | 0.80 | 83 | <0.02 | <0.01 | 72 | no | 265-56 | PDC+ |
| 2xLhLDH | 0.77 | 78 | <0.02 | <0.01 | 120 | no | 257-6 | PDC+ |
| 2xLhLDH | 0.89 | 90 | <0.02 | <0.01 | 72 | no | 247-9 | PDC+ |
| 1xRoLDH+ 1xBmLDH | 0.76 | 79 | <0.02 | <0.01 | 72 | yes | 278-17 | pdc1− |
| 1xRoLDH+ 2xBmLDH | 0.86 | 89 | <0.02 | <0.01 | 96 | yes | 278-14 | pdc1− |

TABLE 10

Glucose g/L at different time points. n.d. = not determined; * = calcium lactate precipitate.

| Strain | 0 h | 4 h | 8 h | 12 h | 24 h | 48 h | 72 h | 96 | 120 h | 144 h |
|---|---|---|---|---|---|---|---|---|---|---|
| *C. sonorensis* | 100.04 | 81.49 | 73.03 | 66.6 | 59.77 | 41.03 | 31.81 | 31.19 | 16.21 | 0.41 |
| *C. sonorensis* | 99.33 | 83.46 | 75.43 | 69.44 | 57.14 | 46.84 | 38.55 | 41.97 | 29.81 | 20.78 |
| 266-3 | 99.79 | 83.58 | 79.35 | 73.54 | 57.52 | 43.14 | 33.63 | 36.48 | 29 | 17.12 |
| 266-11 | 101.71 | 79.68 | 74.38 | 65.46 | 39.54 | 2.29 | 0.00 | 0.00 | 0.00 | 0.00 |
| 266-7 | 98.72 | 82.13 | 74.22 | 64.9 | 44.61 | 17.3 | 1.29 | 0.00 | 0.00 | 0.00 |
| 266-8 | 100.01 | 82.07 | 71.6 | 62.67 | 42.13 | 15.63 | 0.87 | 0.00 | 0.00 | 0.00 |
| 246-27 | 100.32 | 85 | 77.22 | 74.09 | 58.28 | 33.65 | 23.01 | 13.99 | 0.00 | 0.00 |
| 247-11 | 101.89 | 84.23 | 76.25 | n.d. | 58.09 | 33.9 | 22.68 | 8.28 | 0.00 | 0.00 |
| 257-3 | 104.51 | 84.1 | 73.31 | n.d. | 53.18 | 27.2 | 16.14 | 0.00 | 0.00 | 0.00 |
| 257-12 | 99.69 | 81.74 | 77.63 | n.d. | 52.95 | 29.22 | 15.69 | 2.55 | 0.00 | 0.00 |
| 257-6 | 101.32 | 84.78 | 78.34 | 72.66 | 60.85 | 40.53 | 34.2 | 17.44 | 0.00 | 0.00 |
| 247-9 | 100.78 | 85.97 | 77.99 | 68.14 | 50.65 | 9.7 | 0.00 | 0.00 | 0.00 | 0.00 |
| 246-27 | 69.69 | 82.04 | 64.32 | 57.84 | 34.01 | 0.00 | 0.00 | * | | |
| 247-11 | 98.29 | 83.26 | 79.02 | 62.51 | 45.27 | 10.76 | 0.00 | 0.00 | * | |
| *C. sonorensis* | 95.67 | 80.28 | 72.24 | 56.24 | 39.83 | 16.38 | 0.26 | 0.00 | 0.00 | 0.00 |
| *C. sonorensis* | 91.63 | 81.42 | 69.91 | 61.29 | 47.36 | 30.73 | 19.69 | 7.91 | 0.00 | 0.00 |
| 265-39 | 96.51 | 83.44 | 79.68 | 40.33 | 44.55 | 13.96 | 0.00 | * | | |
| 265-15 | 94.7 | 89.05 | 74.6 | 65.28 | 37.52 | 6.58 | 0.00 | * | | |
| 265-44 | 95.32 | 86.01 | 72.89 | 65.3 | 49.24 | 12.38 | 0.00 | 0.00 | * | |
| 265-55 | 91.56 | 90.02 | 70.48 | 68.18 | 49.91 | 24.81 | 4.06 | 0.00 | 0.00 | 0.00 |
| 265-23 | 93.34 | 84.3 | 73.42 | 64.48 | 45.73 | 9.2 | 0.00 | * | | |
| 265-22 | 92.13 | 85.92 | 70.78 | 65.54 | 46.82 | 8.19 | 0.00 | * | | |
| 265-56 | 91.85 | 89.76 | 73.76 | 69.46 | 54.69 | 24.35 | 0.00 | 0.00 | 0.00 | 0.00 |
| 266-3 | 90.68 | 86.01 | 70.34 | 63.32 | 35.98 | 0.00 | 0.00 | 0.00 | 0.00 | 0.00 |
| 278-14 | 92.44 | 89.84 | 74.84 | 67.31 | 50.96 | 20.31 | 0.00 | 0.00 | * | |
| 278-17 | 97.57 | 88.18 | 71.68 | 61.92 | 43.86 | 6.90 | 0.00 | * | | |
| 286-4 | 96.11 | 85.80 | 71.01 | 63.90 | 45.67 | 6.08 | 0.00 | * | | |
| 286-30 | 92.22 | 83.59 | 68.22 | 61.48 | 40.07 | 0.42 | 0.00 | * | | |
| 286-1 | 96.42 | 84.21 | 68.06 | 60.66 | 46.22 | 0.00 | * | | | |

TABLE 11

Lactic acid g/L;

| Strain | 0 h | 4 h | 8 h | 12 h | 24 h | 48 h | 72 h | 96 h | 120 h | 144 h |
|---|---|---|---|---|---|---|---|---|---|---|
| C. sonorensis | 0.00 | 0.00 | 0.00 | 0.00 | 0.00 | 0.00 | 0.00 | 0.18 | 0.00 | 0.00 |
| C. sonorensis | 0.00 | 0.00 | 0.00 | 0.00 | 0.00 | 0.00 | 0.00 | 0.48 | 0.00 | 0.00 |
| 266-3 | 0.34 | 3.15 | 6.27 | 9.41 | 20.34 | 29.26 | 39.2 | 44.51 | 45.82 | 50.54 |
| 266-11 | 0.46 | 5.5 | 12.27 | 18.65 | 37.6 | 65.04 | 77.75 | 77.71 | 76.81 | 77.69 |
| 266-7 | 0.46 | 5.7 | 11.88 | 17.64 | 35.15 | 57.11 | 74.23 | 80.88 | 76.81 | 78.78 |
| 266-8 | 0.48 | 5.87 | 12.04 | 18.21 | 36.34 | 58.92 | 75.07 | 80.45 | 74.72 | 77.76 |
| 246-27 | 0.48 | 5.37 | 10.16 | 15.16 | 28.75 | 40.7 | 58.15 | 70.84 | 80.06 | 77.72 |
| 247-11 | 0.49 | 5.38 | 10.27 | n.d. | 29.24 | 45.05 | 58.11 | 76.73 | 79.92 | 80.27 |
| 257-3 | 0.57 | 6.64 | 12.34 | n.d. | 34.72 | 52.53 | 71.92 | 85.71 | 81.50 | 80.98 |
| 257-12 | 0.51 | 5.76 | 11.46 | n.d. | 32.55 | 51.57 | 56.12 | 81.15 | 80.02 | 82.48 |
| 257-6 | 0.55 | 5.82 | 10.09 | 14.02 | 24.78 | 38.11 | 53.13 | 66.47 | 78.03 | 77.82 |
| 247-9 | 0.63 | 5.44 | 11.46 | 16.50 | 35.7 | 57.83 | 89.75 | 89.66 | 88.58 | 88.47 |
| 246-27 | 0.26 | 8.74 | 15.51 | 23.23 | 43.69 | 76.83 | 84.09 | * | | |
| 247-11 | 0.32 | 6.71 | 14.17 | 17.98 | 37.32 | 73.23 | 85.56 | 84.08 | * | |
| C. sonorensis | 0.00 | 0.00 | 0.00 | 0.00 | 0.00 | 0.00 | 0.00 | 0.00 | 0.00 | 0.00 |
| C. sonorensis | 0.00 | 0.00 | 0.00 | 0.00 | 0.00 | 0.00 | 0.00 | 0.00 | 0.00 | 1.49 |
| 265-39 | 0.18 | 6.85 | 14.67 | 12.27 | 40.22 | 69.97 | 85.02 | * | | |
| 265-15 | 0.23 | 7.43 | 13.78 | 19.78 | 40.3 | 76.86 | 85.17 | * | | |
| 265-44 | 0.21 | 6.91 | 11.63 | 17.11 | 33.47 | (37.27) | 83.02 | 70.25 | * | |
| 265-55 | 0.24 | 7.05 | 10.97 | 17.46 | 32.41 | 59.35 | 79.00 | 85.32 | 78.81 | 87.49 |
| 265-23 | 0.2 | 7.49 | 13.28 | 19.27 | 37.36 | 69.74 | 83.44 | * | | |
| 265-22 | 0.22 | 7.26 | 12.65 | 19.67 | 38.60 | 74.97 | 87.36 | * | | |
| 265-56 | 0.18 | 6.58 | 10.50 | 15.82 | 30.69 | 55.16 | 83.20 | 76.95 | 80.08 | 78.47 |
| 266-3 | 0.14 | 5.77 | 11.34 | 17.43 | 39.25 | 75.38 | 75.31 | 74.41 | 79.04 | 72.06 |
| 278-14 | 0.16 | 6.77 | 11.60 | 17.36 | 34.13 | 66.85 | 87.54 | 89.33 | * | |
| 278-17 | 0.25 | 7.51 | 12.62 | 18.58 | 38.91 | 78.41 | 79.16 | * | | |
| 286-4 | 0.23 | 6.02 | 10.91 | 17.13 | 37.77 | 75.62 | 79.59 | * | | |
| 286-30 | 0.28 | 7.95 | 13.52 | 20.08 | 39.68 | 80.22 | 81.63 | * | | |
| 286-1 | 0.39 | 8.33 | 14.44 | 21.51 | 36.82 | 75.68 | * | | | | n.d. = not determined;
* = calcium lactate precipitate.

TABLE 12

Ethanol g/L. Values below the detection limit (0.02 g/L) are not shown.

| Strain | 0 h | 4 h | 8 h | 12 h | 24 h | 48 h | 72 h | 96 h | 120 h | 144 h |
|---|---|---|---|---|---|---|---|---|---|---|
| C. sonorensis | 0.48 | 2.84 | 5.5 | 7.71 | 11.29 | 14.86 | 13.33 | 15.91 | 17.29 | 20.75 |
| C. sonorensis | 0.4 | 2.52 | 4.88 | 6.77 | 10.37 | 0.82 | 11.34 | 11.8 | 10.47 | 11.4 |
| 266-3 | 0.29 | 0.81 | 1.43 | 2.05 | 3.14 | 0.27 | 1.5 | 0.47 | | |
| 266-11 | 0.36 | 0.93 | 1.53 | 2.28 | 3.85 | 3.46 | 2.21 | 0.94 | | |
| 266-7 | 0.33 | 0.89 | 1.34 | 1.92 | 2.92 | 2.38 | 1.65 | 0.35 | | |
| 266-8 | 0.4 | 1.05 | 1.72 | 2.43 | 3.38 | 2.29 | 2.06 | 0.72 | | |
| 246-27 | | 0.21 | 0.26 | 0.21 | 0.12 | | | | | |
| 247-11 | | 0.2 | 0.17 | n.d. | | | | | | |
| 257-3 | 0.12 | 0.12 | 0.17 | n.d. | | | | | | |
| 257-12 | 0.09 | 0.11 | 0.14 | n.d. | | | | | | |
| 257-6 | | | | | | | | | | |
| 247-9 | | | | | | | | | | |
| 246-27 | 0.05 | 0.18 | 0.21 | | | | | | | |
| 247-11 | 0.06 | 0.14 | 0.12 | | | | | | | |
| C. sonorensis | 0.56 | 4.1 | 7.38 | 6.41 | 10.67 | 15.91 | 18.11 | 16.19 | 13.53 | 20.9 |
| C. sonorensis | 0.54 | 3.66 | 6.58 | 5.21 | 8.05 | 9.48 | 11.51 | 12.05 | 10.88 | 13.13 |
| 265-39 | 0.09 | 0.21 | 0.15 | | | 0.03 | | | | |
| 265-15 | 0 | 0.23 | 0.26 | 0.02 | 0.15 | | | | | |
| 265-44 | 0 | 0.16 | | | | | | | | |
| 265-55 | 0 | 0.13 | | | | | | | | |
| 265-23 | | | | | | | | | | |
| 265-22 | | 0.14 | | | | | | | | |
| 265-56 | | | | | | | | | | |
| 266-3 | 0.27 | 1.38 | 1.18 | 1.65 | 2.15 | 2.13 | 1.52 | 0.47 | | |
| 278-14 | | | | | | | | | | |
| 278-17 | | 0.31 | 0.1 | 0.13 | 0.09 | 0.03 | | | | |
| 286-4 | | 0.22 | 0.15 | 0.21 | 0.29 | 0.37 | | | | |
| 286-30 | | 0.24 | 0.1 | 0.17 | 0.21 | 0.23 | | | | |
| 286-1 | | 0.23 | 0.09 | 0.14 | | 0.16 | | | | | n.d. = not determined.

TABLE 13

| | Lactic acid (g/g glucose consumed). | | | | | | | | | |
|---|---|---|---|---|---|---|---|---|---|---|
| | 0 h | 4 h | 8 h | 12 h | 24 h | 48 h | 72 h | 96 h | 120 h | 144 h |
| C. sonorensis | 0.00 | 0.00 | 0.00 | 0.00 | 0.00 | 0.00 | 0.00 | 0.00 | 0.00 | 0.00 |
| C. sonorensis | 0.00 | 0.00 | 0.00 | 0.00 | 0.00 | 0.00 | 0.00 | 0.01 | 0.00 | 0.00 |
| 266-3 | 0.28 | 0.18 | 0.29 | 0.34 | 0.47 | 0.51 | 0.58 | 0.69 | 0.64 | 0.60 |
| 266-11 | 0.00 | 0.26 | 0.46 | 0.52 | 0.61 | 0.66 | 0.77 | 0.77 | 0.76 | 0.77 |
| 266-7 | 0.20 | 0.30 | 0.44 | 0.49 | 0.62 | 0.68 | 0.74 | 0.80 | 0.76 | 0.78 |
| 266-8 | 0.48 | 0.31 | 0.41 | 0.48 | 0.62 | 0.69 | 0.75 | 0.80 | 0.74 | 0.77 |
| 246-27 | 0.71 | 0.34 | 0.43 | 0.56 | 0.67 | 0.60 | 0.75 | 0.81 | 0.79 | 0.77 |
| 247-11 | 0.00 | 0.32 | 0.41 | n.d. | 0.68 | 0.67 | 0.74 | 0.83 | 0.79 | 0.79 |
| 257-3 | 0.00 | 0.39 | 0.45 | n.d. | 0.73 | 0.71 | 0.85 | 0.85 | 0.81 | 0.80 |
| 257-12 | 0.39 | 0.30 | 0.49 | n.d. | 0.68 | 0.72 | 0.66 | 0.82 | 0.79 | 0.82 |
| 257-6 | 0.00 | 0.36 | 0.45 | 0.49 | 0.62 | 0.63 | 0.80 | 0.80 | 0.77 | 0.77 |
| 247-9 | 2.86 | 0.36 | 0.50 | 0.50 | 0.71 | 0.63 | 0.89 | 0.89 | 0.88 | 0.88 |
| 246-27 | 0.01 | 0.40 | 0.39 | 0.50 | 0.65 | 0.74 | 0.81 | * | | |
| 247-11 | 0.06 | 0.32 | 0.57 | 0.43 | 0.64 | 0.79 | 0.82 | 0.81 | * | |
| C. sonorensis | 0.00 | 0.00 | 0.00 | 0.00 | 0.00 | 0.00 | 0.00 | 0.00 | 0.00 | 0.00 |
| C. sonorensis | 0.00 | 0.00 | 0.00 | 0.00 | 0.00 | 0.00 | 0.00 | 0.00 | 0.00 | 0.01 |
| 265-39 | 0.02 | 0.33 | 0.60 | 0.19 | 0.68 | 0.78 | 0.82 | * | | |
| 265-15 | 0.02 | 0.50 | 0.47 | 0.51 | 0.61 | 0.79 | 0.82 | * | | |
| 265-44 | 0.02 | 0.38 | 0.37 | 0.44 | 0.61 | (0.41) | 0.80 | 0.68 | * | |
| 265-55 | 0.02 | 0.50 | 0.33 | 0.49 | 0.60 | 0.75 | 0.79 | 0.82 | 0.76 | 0.84 |
| 265-23 | 0.02 | 0.38 | 0.43 | 0.49 | 0.64 | 0.74 | 0.80 | * | | |
| 265-22 | 0.02 | 0.40 | 0.38 | 0.51 | 0.68 | 0.78 | 0.84 | * | | |
| 265-56 | 0.01 | 0.46 | 0.35 | 0.46 | 0.62 | 0.69 | 0.80 | 0.72 | 0.77 | 0.75 |
| 266-3 | 0.01 | 0.32 | 0.34 | 0.43 | 0.58 | 0.72 | 0.72 | 0.74 | 0.76 | 0.69 |
| 278-14 | 0.01 | 0.48 | 0.40 | 0.47 | 0.64 | 0.80 | 0.84 | 0.86 | * | |
| 278-17 | 0.04 | 0.47 | 0.39 | 0.44 | 0.65 | 0.81 | 0.76 | * | | |
| 286-4 | 0.03 | 0.33 | 0.33 | 0.43 | 0.65 | 0.77 | 0.77 | * | | |
| 286-30 | 0.02 | 0.39 | 0.38 | 0.47 | 0.62 | 0.77 | 0.78 | * | | |
| 286-1 | 0.05 | 0.42 | 0.40 | 0.50 | 0.64 | 0.73 | * | | | | n.d. = not determined;
* = calcium lactate precipitate.

Example 20

Production of L-lactic Acid in Defined Glucose Medium in Nitrogen Sparged Tubes by *C. sonorensis* Harboring *L. helveticus* or *R. oryzae* LDH Encoding Gene Integrated into the Genome Production of L-lactic acid in transformed *C. sonorensis* cells was demonstrated as follows. *C. sonorensis* cells and the transformants harboring the *L. helveticus* LDH gene (namely, 246-14, 246-14, 246-18, 246-23, 246-27, 247-7, 247-8, 247-11, and 257-3) or the *R. oryzae* LDH gene (266-3 and 266-4) were cultivated in YD medium (yeast nitrogen base without amino acids supplemented with 12% glucose and 0.4 M MES pH 5.5). Precultures were grown in 50 mL of YD medium (yeast nitrogen base without amino acids supplemented with 6.5% glucose and 0.4 M MES, pH 5.5) in 250 mL Erlenmeyer flasks with 250 rpm shaking at 30° C. Cells were collected by centrifugation and washed once with 0.9% NaCl, then resuspended in 50 mL of YD medium to an $OD_{600}$ of 11 for the cultivation experiments. Yeasts were cultivated in 50 mL disposable plastic tubes sparged with nitrogen with 250 rpm shaking at 30° C. ((nearly) anaerobic conditions). Samples were withdrawn during cultivation, and after that the tubes were sparged with nitrogen. $OD_{600}$ was measured, and cells harvested by centrifugation and the culture supernatant analyzed by HPLC as described above for lactic acid, glucose and ethanol. These results are shown in Tables 14–20.

After 94 hours of cultivation the transformants harboring *L. helveticus* LDH gene produced 6.9–7.2 g/L lactic acid (equivalent to 66–84% yield) and 1–1.4 g/L ethanol, whereas the host strain produced 0.1 g/L lactic acid and 40 g/L ethanol. The transformants harboring *R. oryzae* LDH gene produced 7.2–8.8 g/L lactic acid (equivalent to 13–18% yield) and 17–28 g/L ethanol after 94 hours of cultivation. Glucose consumption and ethanol production by the *R. oryzae* LDH transformants were faster than those of the *L. helveticus* transformants.

These results showed that *C. sonorensis* transformed with *L. helveticus* LDH or *R. oryzae* LDH produced lactic acid from glucose in nitrogen sparged tube cultures.

TABLE 14

| | Lactic acid g/g glucose consumed | | | | |
|---|---|---|---|---|---|
| Strains | 0 h | 27 h | 46 h | 70 h | 94 h |
| 247-7 | 0 | 0.93 | 1.04 | 0.90 | 0.75 |
| 247-8 | 0 | 1.09 | 0.98 | 0.90 | 0.66 |
| 247-11 | 0 | 0.84 | 0.91 | 0.88 | 0.80 |
| 246-14 | 0 | 1.02 | 1.02 | 0.91 | 0.78 |
| 246-18 | 0 | 1.08 | 0.91 | 0.77 | 0.71 |
| 246-23 | 0 | 0.89 | 0.94 | 0.87 | 0.84 |
| 246-27 | 0 | 0.83 | 0.95 | 0.88 | 0.83 |
| C. sonorensis | 0 | 0.00 | 0.00 | 0.00 | 0.00 |
| 266-3 | 0 | 0.37 | 0.22 | 0.17 | 0.13 |
| 266-4 | 0 | 0.32 | 0.26 | 0.22 | 0.18 |
| 257-3 | 0 | 1.00 | 0.88 | 0.93 | 0.76 |

Example 21

Production of L-lactic Acid in Rich Glucose Medium without Buffering in Microaerobic Shake Flask Cultures by *C. sonorensis* Harboring *L. helveticus* or *B. megaterium* LDH Gene Integrated into the Genome Production of L-lactic acid in transformed *C. sonorensis* cells was demonstrated as follows. The *C. sonorensis* transformants harboring the *B. megaterium* LDH gene (namely, 265-23 and 286-1) and *L. helveticus* LDH gene (246-27 and 247-11) disclosed above were cultivated in 50 mL of YD medium (yeast nitrogen base without amino acids supplemented with 5% glucose and 0.5 M MES, pH 5.5) in 250 mL Erlenmeyer flasks with 250 rpm shaking at 30° C. Cells were collected by centrifugation and then resuspended in 50 mL of YP supplemented with 5% glucose to an $OD_{600}$ of 15 for the cultivation experiments. Cells were cultivated in 250 mL Erlenmeyer flasks with 100 rpm shaking at 30° C. Samples were withdrawn during cultivation, $OD_{600}$ measured, and cells were harvested by centrifugation. The culture supernatant analyzed for L-lactic acid (by the L-lactic acid UV method of Boehringer Mannheim, Roche), for glucose (by the glucose/GOD-Perid method of Boehringer Mannheim, Roche), for acetate (by the acetic acid UV method of Boehringer Mannheim, Roche), and for ethanol (by the ethanol UV method of Boehringer Mannheim, Roche). These results are shown in Tables 15–20.

Transformants 246-27 and 247-11 harboring *L. helveticus* LDH gene integrated randomly into the yeast genome (PDC+ genotype) produced 7.8–9.0 g/L lactic acid (equivalent to 24–29% yield) after 24 hours of cultivation. The transformant 286-1 harboring *B. megaterium* LDH gene integrated into the pdc2 gene locus (pdc2-genotype) produced 8.9 g/L lactic acid (equivalent to 31% yield) after 24 hours of cultivation. Transformant 265-23 harboring two copies of *B. megaterium* LDH gene integrated randomly into genome (PDC+ genotype) produced 9.1 g/L lactic acid (equivalent to 30% yield) after 24 hours of cultivation. After 24 hours of cultivation the transformants harboring *B. megaterium* LDH gene produced 8.9–9.1 g/L lactic acid, equivalent to 30–31% yield from glucose. Transformants harboring the *L. helveticus* LDH gene produced 7.8–9.0 g/L lactic acid, which is equivalent to 24–29% yield from glucose. Although some glucose was unconsumed at 24 h, all glucose was eventually consumed (at 120 h). No further increase in lactic acid concentration occurred after 24 h, however. Glucose consumption by all strains was very similar. The pH of the culture medium was between 3.4–3.8 during this experiment. The transformant 265-23 containing two copies of *B. megaterium* LDH produced less ethanol and acetate early in the cultivation whereas the pdc2-transformant 286-1 produced less ethanol and acetate towards the end of the cultivation than the other strains.

These results demonstrated that *C. sonorensis* transformed with *L. helveticus* LDH or *B. megaterium* LDH was capable of producing lactic acid from glucose under microaerobic conditions at low pH up to 9 g/L.

TABLE 15

Absorbance $OD_{600}$

| Strain | 0 h | 4 h | 8 h | 12 h | 24 h | 48 h | 72 h | 96 h | 120 h |
|---|---|---|---|---|---|---|---|---|---|
| 265-23 | 17.40 | 16.1 | 15.2 | 15.30 | 18.40 | 15.4 | 13.6 | 14.8 | 17.8 |
| 286-1 | 15.80 | 16.4 | 15.6 | 15.30 | 20.40 | 16.2 | 16.5 | 20.1 | 25.0 |
| 246-27 | 16.20 | 15.9 | 15.8 | 16.90 | 18.20 | 15.1 | 14.1 | 17.0 | 23.7 |
| 247-11 | 15.80 | 15.4 | 16.3 | 15.40 | 18.60 | 15.8 | 13.4 | 16.1 | 23.3 |

TABLE 16

Glucose g/L in different time points

| Strain | 0 h | 4 h | 8 h | 12 h | 24 h | 48 h | 72 h | 96 h | 120 h |
|---|---|---|---|---|---|---|---|---|---|
| 265-23 | n.d. | n.d. | n.d. | 27.1 | 19.51 | 10.2 | 8.4 | 6.7 | 2.8 |
| 286-1 | n.d. | n.d. | n.d. | 25.5 | 21.6 | 13.2 | 8.1 | 0.9 | 0.0 |
| 246-27 | n.d. | n.d. | n.d. | 25.3 | 18.0 | 9.9 | 6.8 | 2.3 | 0.0 |
| 247-11 | n.d. | n.d. | n.d. | 24.6 | 18.9 | 11.2 | 7.3 | 2.4 | 0.0 |

TABLE 17

Lactic acid g/L

| Strain | 0 h | 4 h | 8 h | 12 h | 24 h | 48 h | 72 h | 96 h | 120 h |
|---|---|---|---|---|---|---|---|---|---|
| 265-23 | 0.46 | 4.41 | 6.31 | 7.57 | 9.10 | 6.49 | 6.04 | 5.78 | 4.35 |
| 286-1 | 0.46 | 4.62 | 5.57 | 7.57 | 8.85 | 7.43 | 5.55 | 5.68 | 5.01 |
| 246-27 | 0.49 | 4.38 | 5.23 | 7.75 | 7.75 | 6.96 | 5.97 | 7.12 | 5.86 |
| 247-11 | 0.49 | 4.35 | 5.18 | 7.40 | 8.97 | 8.18 | 6.08 | 7.39 | 5.06 |

TABLE 18

Ethanol g/L

| Strain | 0 h | 4 h | 8 h | 12 h | 24 h | 48 h | 72 h | 96 h | 120 h |
|---|---|---|---|---|---|---|---|---|---|
| 265-23 | 0.28 | 0.55 | 0.82 | 1.50 | 3.62 | 6.29 | 7.47 | 8.12 | 6.45 |
| 286-1 | 0.25 | 0.77 | 1.14 | 1.57 | 3.84 | 5.43 | 6.23 | 6.96 | 4.50 |
| 246-27 | 0.31 | 0.72 | 1.22 | 1.97 | 4.14 | 6.47 | 7.33 | 7.43 | 5.48 |
| 247-11 | 0.33 | 0.70 | 1.16 | 1.64 | 4.04 | 6.44 | 7.50 | 7.76 | 6.06 |

TABLE 19 pH

| Strain | 0 h | 4 h | 8 h | 12 h | 24 h | 48 h | 72 h | 96 h | 120 h |
|---|---|---|---|---|---|---|---|---|---|
| 265-23 | 5.11 | 3.79 | 3.66 | 3.55 | 3.41 | 3.58 | 3.69 | 3.7 | 3.66 |
| 286-1 | 4.98 | 3.73 | 3.62 | 3.58 | 3.38 | 3.54 | 3.57 | 3.51 | 3.66 |
| 246-27 | 5.09 | 3.74 | 3.66 | 3.57 | 3.41 | 3.53 | 3.68 | 3.63 | 3.62 |
| 247-11 | 5.05 | 3.73 | 3.57 | 3.53 | 3.43 | 3.49 | 3.54 | 3.6 | 3.61 |

TABLE 20

Acetate g/L

| Strain | 0 h | 4 h | 8 h | 12 h | 24 h | 48 h | 72 h | 96 h | 120 h |
|---|---|---|---|---|---|---|---|---|---|
| 265-23 | 0.1 | 0.4 | 0.9 | 1.1 | 2.8 | 5.5 | 6.1 | 4.7 | 1.2 |
| 286-1 | 0.1 | 0.5 | 1.1 | 1.3 | 2.8 | 3.8 | 2.1 | 1.3 | 0.1 |
| 246-27 | 0.1 | 0.5 | 1.1 | 1.4 | 3.0 | 5.0 | 4.6 | 1.4 | 0.0 |
| 247-11 | 0.1 | 0.5 | 1.0 | 1.2 | 2.7 | 4.4 | 4.1 | 1.4 | 0.0 |

Example 22

Production of L-lactic Acid in a Bioreactor in Rich Glucose Medium by *C. sonorensis* Harboring *B. megaterium* LDH Gene Integrated into the Genome

*C. sonorensis* transformants designated 265-55, 286-30 and 265-15, described above, were cultivated in aerobic bioreactors. Batch cultivation was performed at 35° C. in a laboratory bioreactor (Biostat CT-DCU3, Braun, Germany) with a working volume of 2 L. During the production phase the pH was maintained at 5.0±0.1 or increased to 6.0±0.1 after 48 hours of cultivation by automated addition of 5 M potassium hydroxide (KOH). Biomass was produced with YP medium supplemented with 150 g/L glucose. The biomass production phase was inoculated with 20 mL of culture stored in 23% (w/v) glycerol at −80° C. to an initial $OD_{600}$ of 0.7–1. The bioreactor was flushed with 100% air at a flow rate of 1.0 L/min and stirred at 800 rpm during this phase. After 23.5 hours of cultivation 10–21 g/L cell mass was produced (dry weight) (equivalent to 0.2–0.3 g dry weight per used gram of glucose). After the 24 hour biomass production, the bioreactor was emptied and cells were collected by centrifugation (4000 rpm, 20° C., 10 min). The medium for lactate production (YP supplemented with 100 g/L glucose) was pumped into the bioreactor and was inoculated with the cells collected from the biomass production phase, to a density corresponding to 5 g/L dry weight. The bioreactor was flushed with 10% air-90% nitrogen gas at a flow rate of 1.0 L min$^{-1}$ and stirred at 500 rpm.

Samples were withdrawn during cultivation. For each sample, dry cell weight was determined, the $OD_{600}$ was measured, and the cells were harvested by centrifugation. Culture supernatants were analyzed by HPLC as described above for lactic acid, glucose, ethanol, and acetate. These results are shown in Tables 21 and 22.

The transformant harboring the *B. megaterium* LDH gene integrated randomly into the genome (265-55, PDC+ genotype) produced 28 g/L lactic acid (equivalent to 67% yield) at pH 5.0, after 52 hours of cultivation in the lactate production phase. The same transformant produced 28 g/L lactic acid (equivalent to 60% yield) at pH 6.0 after 72 hours of cultivation in the production phase.

The transformant harboring the *B. megaterium* LDH gene integrated into the pdc1 gene locus (265-15, pdc1-genotype) produced 23 g/L lactic acid (equivalent to 66% yield) at pH 5.0 after 51 hours of cultivation in the lactate production phase.

The transformant harboring the *B. megaterium* LDH gene integrated into the pdc2 gene locus (286-30, pdc2-genotype) produced 27 g/L lactic acid (equivalent to 54% yield) at pH 5.0 after 46 hours of cultivation in the lactate production phase.

After 46 to 52 hours of lactic acid production phase, the transformants produced 23–28 g/L lactic acid (equivalent to a 54–67% yield).

These results demonstrated that *C. sonorensis* overexpressing a heterologous lactate dehydrogenase encoding gene produced lactic acid from glucose in batch fermentation under microaerobic condition (e.g. 0%–2% $O_2$ in the atmosphere).

TABLE 21

Biomass production in bioreactor cultivations in YPD medium with 150 g/L glucose

| *C. sonorensis* transformants | Cultivation time (h) | Initial $OD_{600}$ | Final $OD_{600}$ | Glucose consumed (g/L) | Final biomass (cell dry weight g/L) |
|---|---|---|---|---|---|
| 265-55 | 23.5 | 0.68 | 90 | 96 | 20.8 |
| 265-55 | 21.5 | 0.69 | 98 | 73 | 20.5 |
| 286-30 | 23.5 | 1.01 | 42 | 65 | 21.3 |
| 265-15 | 23.5 | 0.85 | 41 | 46 | 10.0 |

TABLE 22

Lactate production with *C. sonorensis* in bioreactor cultivations in YPD medium with 100 g/L glucose. Glucose consumption, lactate concentration, and lactate yield at the time when the peak lactate concentration was achieved. * = pH was increased to 6.0 at 48 h.

| *C. sonorensis* transformants | Initial biomass (cell dry weight g/L) | Ferm. time at peak LA | Glucose consumed (g/L) | L.A. (g/L) | LA yield (g LA/g glucose used) |
|---|---|---|---|---|---|
| 265-55 | 4.5 | 52 h | 42 | 28 | 67% |
| 265-55* | 6.4 | 72 h | 47 | 28 | 60% |
| 286-30 | 4.3 | 46 h | 50 | 27 | 54% |
| 265-15 | 5.3 | 51 h | 35 | 23 | 66% |

TABLE 23

Byproduct production with *C. sonorensis* in bioreactor cultivations in YPD medium with 100 g/L glucose. Byproduct concentrations at the time when the peak lactate concentration was achieved. * = pH was increased to 6.0 at 48 h.

| *C. sonorensis* transformants | Initial biomass (dry wt. g/L) | Ferm. time at peak LA | Ethanol (g/L) | Acetate (g/L) | Glycerol (g/L) | Pyruvate (g/L) |
|---|---|---|---|---|---|---|
| 265-55 | 4.5 | 52 h | 1.9 | 4.5 | 0 | 0.71 |
| 265-55* | 6.4 | 72 h | 0.6 | 10.6 | 0 | 0.79 |
| 286-30 | 4.3 | 46 h | 2.3 | 5.0 | 0 | 0.39 |
| 265-15 | 5.3 | 51 h | 1.4 | 5.0 | 0 | 0.06 |

Intracellular Lactic Acid and Pyruvate

Intracellular lactic acid and pyruvate concentrations were determined as described above in Example 17, except that the sample volume was 1 mL and the cell pellet was washed (1 mL) in 1 M Tris-HCl, pH 9.0, centrifuged at 13,000 rpm for 1 min., and stored at −70° C. After thawing, the pellet was directly suspended into 1 mL of ice-cold 5% TCA. Intracellular pyruvate concentration was analyzed from the sample enzymatically (pyruvate kit, Sigma Diagnostics). These results are shown in Tables 24–27.

The transformant harboring the *B. megaterium* LDH gene integrated randomly into the genome (265-55, PDC+ genotype) produced 60.9 g/L of lactic acid in the cells at 52 hours of cultivation in the lactate production phase, at pH 5.0. The same transformant produced 38.7 g/L of lactic acid, at pH 6.0, at 72 hours of cultivation in the lactate production phase.

The transformant harboring the *B. megaterium* LDH gene integrated into the pdc1 locus (265-15, pdc1-genotype) produced 13.4 g/L of lactic acid in the cells at 51 hours of cultivation in the lactate production phase.

The transformant harboring the *B. megaterium* LDH gene integrated into the pdc2 locus (286-30, pdc2-genotype) produced 14.3 g/L lactic acid at 49 hours of cultivation in the lactate production phase.

The transformant harboring the *B. megaterium* LDH gene integrated randomly into the genome (265-55, PDC+ genotype) produced 0.1 g/L of pyruvate in the cells during the cultivation at pH 5.0 and at pH 6.0.

The transformant harboring the *B. megaterium* LDH gene integrated into the pdc1 locus (265-15, pdc1-genotype) or into the pdc2 locus (286-30, pdc2-genotype) produced 0.3 g/L pyruvate in the cells during the cultivations.

These results showed that deletion of pdc1 and disruption of pdc2 caused an increase in intracellular pyruvate levels. In the PDC+ strain intracellular lactic acid levels increased towards the end of the cultivations, although this trend was not as clear in the pdc1- and in the pdc2-strains.

TABLE 24

Intracellular lactate and pyruvate concentration (g/L) in the strain 265-55 (PDC+, pH 5.0)

| Time (h) | lactic acid (g/L) | pyruvate (g/L) |
|---|---|---|
| 0 | 15.9 | 0.1 |
| 3.1 | 17.0 | 0.1 |
| 6.1 | 13.9 | 0.1 |
| 9.0 | 17.9 | 0.0 |
| 20.9 | 20.9 | 0.1 |
| 24.2 | 40.6 | 0.1 |
| 27.9 | 25.2 | 0.1 |
| 44.8 | 28.4 | 0.0 |
| 49.1 | 40.3 | 0.1 |
| 51.6 | 60.9 | 0.2 |

TABLE 25

Intracellular lactate and pyruvate concentration (g/L) in the strain 265-55 (PDC+, pH 6.0))

| Time (h) | Lactic acid (g/L) | Pyruvate (g/L) |
|---|---|---|
| 0 | 10.67 | 0.2 |
| 4.7 | 11.15 | 0.1 |
| 21.1 | 12.97 | 0.2 |
| 19.4 | 95.83 | 0.2 |
| 22.4 | 23.08 | 0.1 |
| 24.5 | 24.89 | 0.1 |
| 48.3 | 39.67 | 0.1 |
| 71.7 | 38.7 | 0.1 |

TABLE 25-continued

Intracellular lactate and pyruvate concentration (g/L) in the strain 265-55 (PDC+, pH 6.0))

| Time (h) | Lactic acid (g/L) | Pyruvate (g/L) |
|---|---|---|
| 91.6 | 42.0 | 0.1 |
| 96.1 | 53.4 | 0.1 |
| 97.9 | 55.5 | 0.1 |

TABLE 26

Intracellular lactate and pyruvate concentration (g/L) in the strain 286-30 (pdc2-, pH 5.0)

| Time (h) | Lactic acid (g/L) | Pyruvate (g/L) |
|---|---|---|
| 1.7 | 14.3 | 0.4 |
| 3.1 | 15.0 | 0.1 |
| 22.2 | 24.2 | 0.2 |
| 24.5 | 26.0 | 0.2 |
| 39.1 | 15.1 | 0.3 |
| 48.7 | 14.3 | 0.3 |
| 66.7 | 45.8 | 0.4 |
| 70.5 | 43.7 | 0.5 |

TABLE 27

Intracellular lactate and pyruvate concentration (g/L) in the strain 265-15 (pdc1-, pH 5.0)

| Time (h) | Lactic acid (g/L) | Pyruvate (g/L) |
|---|---|---|
| 1.3 | 11.8 | 0.2 |
| 16.6 | 11.1 | 0.3 |
| 19.7 | 14.6 | 0.2 |
| 22.4 | 17.7 | 0.2 |
| 50.6 | 13.4 | 0.3 |
| 76.1 | 13.4 | 0.3 |
| 89.0 | 41.5 | 0.2 |
| 94.8 | 23.5 | 0.1 |

Lactate Dehydrogenase and Pyruvate Decarboxylase Activities

Lactate dehydrogenase and pyruvate decarboxylase activities were determined as follows. Samples for enzyme activity measurements (2 mL) were collected by centrifugation and the cell pellets were washed with 1 mL of ice-cold 10 mM $K_2HPO_4/KH_2PO_4$, pH 7.5 supplemented with 2 mM EDTA. Washed pellets were resuspended in 0.5 mL of the same buffer and stored at −70° C. Samples were thawed at room temperature and washed (1 mL) once in homogenization buffer (100 mM $KH_2PO_4/K_2HPO_4$, pH 7.5, supplemented with 2 mM $MgCl_2$ and 10 mM DTT). Washed samples were resuspended in 0.5 mL of homogenization buffer and homogenized with 0.5 mL of glass beads with a Bead Beater homogenizer for 1 minute. After homogenization samples were centrifuged 14,000 rpm for 30 min at 4° C. Supernatant samples were collected and lactate dehydrogenase and pyruvate decarboxylase activities were determined spectrophotometrically ($A_{340}$) as described above in example 18, except that glyoxylic acid was not used. These results are shown in Tables 28–31.

The transformant harboring *B. megaterium* LDH gene integrated randomly into the genome (265-55, PDC+ genotype) produced lactate dehydrogenase activity of 1.4 U/mg total cellular protein and pyruvate decarboxylase activity of 0.8 U/mg total cellular protein at 52 hours of cultivation in the lactate production phase at pH 5.0. The same transformant produced lactate dehydrogenase activity of 1.2 U/mg total cellular protein and pyruvate decarboxylase activity of 0.4 U/mg total cellular protein, at pH 6.0, at 72 hours of cultivation in the lactate production phase.

The transformant harboring the *B. megaterium* LDH gene integrated into the pdc1 locus (265-15, pdc1-genotype) produced lactate dehydrogenase activity of 1.5 U/mg total cellular protein and pyruvate decarboxylase activity of 0.5 U/mg total cellular protein at 51 hours of cultivation in the lactate production phase.

The transformant harboring the *B. megaterium* LDH gene integrated into the pdc2 locus (286-30, pdc2-genotype) produced lactate dehydrogenase activity of 0.7 U/mg total cellular protein and pyruvate decarboxylase activity of 0.1 U/mg total cellular protein, at 49 hours of cultivation in the lactate production phase.

These results demonstrated that LDH activity is similar in all strains that contain one copy of the *B. megaterium* LDH integrated in the genome. LDH activity was higher than PDC activity (U/mg total cellular protein) and thus LDH could compete efficiently with PDC for pyruvate. The pdc2-strain 286-30 has clearly reduced PDC activity compared with the wild type. The observed effect of the pdc1 deletion on PDC activity in the pdc1-strain 265-15 was a more gradual decrease in activity over time.

TABLE 28

Lactate dehydrogenase and pyruvate decarboxylase activities (265-55 (PDC+, pH 5.0))

| hours | LDH (U/mg total cellular protein) | PDC (U/mg total cellular protein) |
| --- | --- | --- |
| 0 | 1.9 | 0.41 |
| 3.1 | 1.83 | 0.58 |
| 6.08 | 1.78 | 0.79 |
| 8.95 | 1.74 | 0.82 |
| 20.92 | 1.6 | 0.95 |
| 24.17 | 1.92 | 0.98 |
| 27.93 | 2.13 | 0.92 |
| 44.83 | n.d. | 1 |
| 49.13 | 1.88 | 0.97 |
| 51.62 | 1.35 | 0.77 |

TABLE 29

Lactate dehydrogenase and pyruvate decarboxylase activities (265-55 (PDC+, pH 6.0))

| Hour | LDH (U/mg total cellular protein) | PDC (U/mg total cellular protein) |
| --- | --- | --- |
| 0 | 1.13 | 0.28 |
| 2.08 | 1.11 | 0.3 |
| 4.73 | 0.75 | 0.31 |
| 19.35 | 1.19 | 0.5 |
| 22.35 | 1.14 | 0.51 |
| 24.47 | 1.8 | 0.55 |
| 48.33 | 1.09 | 0.46 |
| 71.73 | 1.21 | 0.35 |
| 91.63 | 0.69 | 0.27 |
| 96.08 | n.d. | 0.22 |
| 97.88 | 1.72 | 0.23 |

TABLE 30

Lactate dehydrogenase and pyruvate decarboxylase activities (265-15 (pdc1-, pH 5.0))

| hours | LDH (U/mg total cellular protein) | PDC (U/mg total cellular protein) |
| --- | --- | --- |
| 16.63 | 0.91 | 0.52 |
| 19.65 | 1.09 | 0.57 |

TABLE 30-continued

Lactate dehydrogenase and pyruvate decarboxylase activities (265-15 (pdc1-, pH 5.0))

| hours | LDH (U/mg total cellular protein) | PDC (U/mg total cellular protein) |
| --- | --- | --- |
| 22.38 | 0.78 | 0.52 |
| 50.58 | 1.54 | 0.46 |
| 76.08 | 4.38 | 0.34 |
| 88.95 | 2.25 | 0.16 |
| 94.83 | 1.41 | 0.21 |

TABLE 31

Lactate dehydrogenase and pyruvate decarboxylase activities (286-30(pdc2-, pH 5.0))

| hours | LDH (U/mg total cellular protein) | PDC (U/mg total cellular protein) |
| --- | --- | --- |
| 1.65 | 0.82 | 0.19 |
| 3.08 | 1.09 | 0.23 |
| 22.22 | 0.78 | 0.14 |
| 24.52 | 1.56 | 0.26 |
| 39.05 | 0.85 | 0.15 |
| 48.73 | 0.72 | 0.12 |
| 66.67 | 0.17 | 0.06 |
| 70.5 | 0.26 | 0.08 |

Example 23

Anaerobic Production of L-lactic Acid in a Bioreactor in Rich Glucose Medium by *C. sonorensis* Harboring the *B. megaterium* LDH Gene Integrated into the Genome The *C. sonorensis* transformant designated 265-55 described above was cultivated in a bioreactor. Batch cultivation was carried out at 35° C. in a laboratory bioreactor (Biostat CT-DCU3, Braun, Germany) with a working volume of 2 L. Biomass was produced aerobically on YP medium supplemented with 150 g/L glucose. The biomass production phase was inoculated with 20 mL of culture stored in 23% (w/v) glycerol at −80° C. The bioreactor was flushed with 100% air at a flow rate of 1.0 L/min, and stirred at 800 rpm. The dissolved-oxygen concentration was continuously monitored with an oxygen electrode (Mettler Toledo). After 22.5 hours of biomass production the bioreactor was emptied and cells were collected by centrifugation (4000 rpm, 20° C., 10 min). Medium for lactic acid production (YP supplemented with 100 g/L glucose) was pumped into the bioreactor, and was inoculated with the centrifuged biomass to a density equivalent of 4.5 g/L cell dry weight. The bioreactor was flushed with 100% nitrogen at a flow rate of 1.0 L/min and stirred at 500 rpm. The pH was maintained at 5.0 ±0.1 by automated addition of 5 M potassium hydroxide (KOH).

Samples were withdrawn during cultivation. Cell dry weight was determined, $OD_{600}$ was measured, and cells were harvested by centrifugation. The culture supernatants were analyzed for L-lactic acid (by the L-lactic acid UV method of Boehringer Mannheim) and glucose content (by the glucose/GOD-Perid method of Boehringer Mannheim). These results are shown in Tables 32 and 33.

After 120 h of cultivation 4.7 g/L lactic acid was produced from glucose (equivalent to a 52% yield).

This example demonstrated that *C. sonorensis* overexpressing a heterologous lactate dehydrogenase was capable of producing lactic acid from glucose under anaerobic batch fermentation.

TABLE 32

Aerobic biomass production in a bioreactor cultivation
in YPD medium with 150 g/L glucose.

| C. sonorensis transformant | Cultivation time (h) | Initial OD$_{600}$ | Final OD$_{600}$ | Final biomass (cell dry weight g/L) |
|---|---|---|---|---|
| 265-55 | 22.5 | 0.77 | 74 | 20.1 |

TABLE 33

Lactic acid production with C. sonorensis overexpressing B.
megaterium LDH in anaerobic bioreactor cultivation in YPD
medium with 100 g/L glucose: glucose consumption,
lactic acid concentration and lactic acid yield.

| C. sonorensis transformant | Initial biomass (dry weight g/L) | Ferm. time | Glucose consumed (g/L) | Lactic acid (g/L) | L.A. yield (gLA/g glucose consumed) |
|---|---|---|---|---|---|
| 265-55 | 4.5 | 120 h | 9 | 4.7 | 0.52 |

Example 24

Production of L-lactic Acid in a Bioreactor in Ca(OH)$_2$-buffered Rich Glucose Medium by C. sonorensis Harboring B. megaterium LDH Gene Integrated into the Genome The C. sonorensis transformant designated 265-55 described above was cultivated by batch cultivation in a bioreactor (Biostat CT-DCU3, Braun, Germany) at 35° C. as described in Example 23. After 18.5 hours of biomass production the bioreactor was emptied and cells were collected by centrifugation (4000 rpm, 20° C., 10 min). The medium for lactic acid production (YP supplemented with 100 g/L glucose) was pumped into the bioreactor and inoculated with the centrifuged biomass to a density equivalent of 6.7 g/L cell dry weight. The bioreactor was flushed with 90% nitrogen and 10% air at a flow rate of 1.0 L/min and stirred at 500 rpm. The pH was maintained at 5.0±0.1 by automated addition of 2.5 M calcium hydroxide (Ca(OH)$_2$).

Samples were withdrawn during cultivation. Cell dry weight was determined, OD$_{600}$ was measured and cells were harvested by centrifugation. The culture supernatants were analyzed for L-lactic acid (by the L-lactic acid UV method, Boehringer Mannheim) and glucose content (by the glucose/GOD-Perid method, Boehringer Mannheim). These results are shown in Tables 34 and 35.

After 53 hours of cultivation, 26 g/L lactic acid was produced from glucose (equivalent to a 67% yield).

These results demonstrated that C. sonorensis overexpressing B. megaterium lactate dehydrogenase was capable of producing lactic acid from glucose in a microaerobic batch fermentation, (2% O$_2$) with calcium hydroxide buffering.

TABLE 34

Aerobic biomass production in a bioreactor cultivation
in YPD medium with 150 g/L glucose.

| C. sonorensis transformant | Cultivation time (h) | Initial OD$_{600}$ | Final OD$_{600}$ | Final biomass (cell dry weight g/L) |
|---|---|---|---|---|
| 265-55 | 18.5 | 2.19 | 46 | 16.5 |

TABLE 35

Lactic acid production with C. sonorensis overexpressing
B. megaterium LDH in a bioreactor cultivation in YPD
medium with 100 g/L glucose: glucose consumption,
lactic acid concentration and lactic acid yield.

| C. sonorensis transformant | Initial biomass (dry weight g/L) | Ferm. time | Glucose consumed (g/L) | Lactic acid (g/L) | L.A. yield (g L.A./g glucose consumed) |
|---|---|---|---|---|---|
| 265-55 | 6.7 | 53 h | 39 | 26 | 0.67 |

Example 25

Production of L-lactic Acid in a Bioreactor in Rich Glucose Medium by C. sonorensis Harboring L. helveticus LDH Gene Integrated into the Genome The C. sonorensis transformants designated 247-5 and 247-11 described above were cultivated by batch cultivation in a laboratory bioreactor (Biostat CT-DCU3, Braun, Germany) at 30° C. (strain 247-11) or 35° C. (strain 247-5) with a working volume of 2 L. The cultivation medium was YP supplemented with 40 g/L glucose. Precultures were grown on YPD medium to an OD$_{600}$ of 11–16, cells were collected by centrifugation and the bioreactor was inoculated to an OD$_{600}$ of 1. Cultivation continued until all glucose was consumed. The pH was maintained at 5.0±0.1 by automated addition of 5 M potassium hydroxide (KOH). The bioreactor was flushed with 5% air and 95% nitrogen gas at a flow rate of 0.5 L/min and stirred at 500 rpm. The dissolved-oxygen concentration was continuously monitored with an oxygen electrode (Mettler Toledo).

Samples were withdrawn during cultivation. Cell dry weight was determined, OD$_{600}$ was measured, and the cells were harvested by centrifugation. The culture supernatants were analyzed by HPLC as described above for lactic acid, glucose, ethanol and acetate. These results are shown in Tables 36 and 37.

After 52 to 69 hours of cultivation, the transformants produced 26–29 g/L of lactic acid (equivalent to a 67–72% yield) from glucose.

These results demonstrated that C. sonorensis overexpressing the L. helveticus lactate dehydrogenase gene was capable of producing lactic acid from glucose in a microaerobic batch fermentation.

TABLE 36

Lactate production with C. sonorensis overexpressing
L. helveticus LDH in two bioreactor cultivations in YPD
medium with 40 g/L glucose: glucose consumption, lactate
concentration and lactate yield at the end of fermentation
(all glucose used).

| C. sonorensis transformants | Initial biomass (dry weight g/L) | Ferm. time | Glucose used (g/L) | L.A. (g/L) | L.A. yield (g L.A./g glucose consumed) |
|---|---|---|---|---|---|
| 247-5 | 0.25 | 52 h | 40.0 | 28.9 | 0.72 |
| 247-11 | 0.26 | 69 h | 39.5 | 26.6 | 0.67 |

TABLE 37

Lactate production with *C. sonorensis* overexpressing *L. helveticus* LDH in two bioreactor cultivations in YPD medium with 40 g/L glucose: byproduct concentrations.

| C. sonorensis transformants | Initial biomass (dry weight g/L) | Ferm. time | Final biomass (dry wt. g/L) | Ethanol (g/L) | Acetate (g/L) | Glycerol (g/L) |
|---|---|---|---|---|---|---|
| 247-5 | 0.25 | 52 h | 1.5 | 0.76 | 0.21 | 0 |
| 247-11 | 0.26 | 69 h | 1.8 | 1.91 | 0.30 | 0 |

Example 26

Production of L-lactic Acid in Defined Xylose Medium by *C. sonorensis* Cells Harboring *L. helveticus* LDH Gene Integrated into the Genome

*C. sonorensis* cells and the transformants disclosed above (specifically, 246-1, 246-10, 247-2, and 247-5) were cultivated in YX-medium (yeast nitrogen base without ammonium sulfate and amino acids supplemented with 0.3% urea and 5% xylose). Precultures were grown in YPD-medium, cells were collected by centrifugation, washed once with YX-medium and then resuspended in 50 mL of YX medium to an $OD_{600}$ of 14–22 for the cultivation experiments. Yeast cells were cultivated in 100 mL Erlenmeyer flasks with 100 rpm shaking at 30° C. When the pH reached approximately 3.5, 0.2% solid calcium carbonate was added. Samples were withdrawn during cultivation, $OD_{600}$ measured, cells were harvested by centrifugation, and the culture supernatant was analyzed by HPLC, as described above. These results are shown in Table 38.

After 71 hours of cultivation, the transformants harboring *L. helveticus* LDH produced 3.6–5.0 g/L lactic acid, equivalent to 18–34% yield from xylose, whereas *C. sonorensis* host did not produce detectable lactic acid. The biomass increased less than 10% during the 167 hour experiment. The transformants utilized 10–30 g/L xylose and produced 4–9 g/L of lactic acid. One third of used xylose was converted into lactic acid by the transformants 246-10 and 247-5.

These results demonstrated that *C. sonorensis* overexpressing a heterologous lactate dehydrogenase gene was capable of producing lactic acid from xylose.

TABLE 38

$OD_{600}$, residual xylose and lactic acid production by *C. sonorensis* and the *L. helveticus* LDH transformants on defined xylose medium.

| Strain | 1 h | 3 h | 24 h | 48 h | 71 h | 167 h |
|---|---|---|---|---|---|---|
| C. sonorensis, $OD_{600}$ | 18.0 | 19.1 | 18.4 | 18.8 | 19.1 | 23.7 |
| 246-1, $OD_{600}$ | 22.4 | 25.7 | 24.6 | 23.9 | 23.4 | 25.3 |
| 247-2, $OD_{600}$ | 20.5 | 21.2 | 21.3 | 21.7 | 18.8 | 23.2 |
| 246-10, $OD_{600}$ | 19.5 | 19.3 | 17.3 | 18.8 | 18.4 | 16.2 |
| 247-5, $OD_{600}$ | 14.8 | 14.9 | 15.4 | 14.9 | 13.9 | 14.9 |
| C. sonorensis, xylose g/L | 45.00 | 43.99 | 40.32 | 34.95 | 26.79 | 7.22 |
| 246-1, xylose g/L | 42.67 | 42.56 | 40.53 | 35.43 | 29.79 | 13.15 |
| 247-2, xylose g/L | 44.61 | 44.45 | 41.81 | 33.63 | 23.66 | 11.18 |
| 246-10, xylose g/L | 45.21 | 44.90 | 44.01 | 38.8 | 35.44 | 33.73 |
| 247-5, xylose g/L | 45.31 | 44.74 | 42.94 | 37.81 | 30.34 | 17.75 |
| C. sonorensis, lactic acid g/L | 0 | 0 | 0 | 0 | 0 | 0 |
| 246-1, lactic acid g/L | 0.45 | 0.55 | 1.18 | 2.44 | 4.12 | 5.84 |
| 247-2, lactic acid g/L | 0.00 | 0.10 | 1.16 | 3.01 | 4.09 | 6.42 |
| 246-10, lactic acid g/L | 0.30 | 0.40 | 0.95 | 2.18 | 3.55 | 4.12 |
| 247-5, lactic acid g/L | 0.26 | 0.37 | 1.09 | 3.08 | 4.97 | 9.02 |
| C. sonorensis, lactic acid g/g DW | 0.00 | 0.00 | 0.00 | 0.00 | 0.00 | 0.00 |
| 246-1, lactic acid g/g DW | 0.07 | 0.07 | 0.16 | 0.34 | 0.59 | 0.77 |
| 247-2, lactic acid g/g DW | 0.00 | 0.02 | 0.18 | 0.46 | 0.72 | 0.92 |
| 246-10, lactic acid g/g DW | 0.05 | 0.07 | 0.18 | 0.39 | 0.64 | 0.85 |
| 247-5, lactic acid g/g DW | 0.06 | 0.08 | 0.24 | 0.69 | 1.19 | 2.02 |
| C. sonorensis, lactic acid g/used xylose g | 0.00 | 0.00 | 0.00 | 0.00 | 0.00 | 0.00 |
| 246-1, lactic acid g/used xylose g | 0.14 | 0.16 | 0.21 | 0.23 | 0.25 | 0.18 |
| 247-2, lactic acid g/used xylose g | 0.00 | 0.06 | 0.28 | 0.24 | 0.18 | 0.18 |
| 246-10, lactic acid g/used xylose g | 0.38 | 0.36 | 0.48 | 0.30 | 0.34 | 0.34 |
| 247-5, lactic acid g/used xylose g | 0.38 | 0.29 | 0.36 | 0.38 | 0.32 | 0.32 |

Example 27

Production of L-lactic Acid in Defined L-arabinose Medium by *C. sonorensis* Harboring *L. helveticus* LDH Gene Integrated into the Genome

*C. sonorensis* cells and the transformants described above (specifically 246-1, 246-10, 247-2, and 247-5) were cultivated in YA-medium (yeast nitrogen base without ammonium sulfate and amino acids supplemented with 0.3% urea and 2% L-arabinose). Precultures were grown in YPD-medium, cells were collected by centrifugation, washed once with YA-medium and resuspended on the 50 mL of YA-medium to an $OD_{600}$ of 14–20 for the cultivation experiments. Yeast cells were cultivated in 100 mL Erlenmeyer flasks with 100 rpm shaking (microaerobic conditions) at 30° C. When the pH reached approximately 3.5, 0.2% solid calcium carbonate was added. Samples were withdrawn during cultivation, $OD_{600}$ measured, the cells were harvested by centrifugation, and the culture supernatant analyzed for lactic acid and xylose by HPLC as described above. These results are shown in Table 39.

After 71 hours of cultivation the transformants harboring the *L. helveticus* LDH produced 2.3–3.2 g/L lactic acid equivalent of 14–34% yield from arabinose, whereas the control strain did not produce detectable lactic acid. The biomass increased 20–60% during the 167 h experiment. The transformants used almost all the 20 g/L arabinose initially provided and produced 3.3–4.5 g/L of lactic acid. About 20% of used arabinose was converted into lactic acid by transformants 246-10 and 247-5.

This example showed that *C. sonorensis* expressing a heterologous LDH gene produced lactic acid from arabinose.

TABLE 39

$OD_{600}$, residual xylose and lactic acid production by *C. sonorensis* and the *L. helveticus* LDH transformants on defined arabinose medium ($OD_{600}$).

| Strain | 1 h | 3 h | 24 h | 48 h | 71 h | 167 h |
|---|---|---|---|---|---|---|
| *C. sonorensis*, $OD_{600}$ | 18.2 | 19.0 | 19.0 | 20.7 | 22.1 | 29.2 |
| 246-1, $OD_{600}$ | 19.7 | 22.2 | 22.6 | 29.5 | 23.2 | 31.2 |
| 247-2, $OD_{600}$ | 18.4 | 19.1 | 19.2 | 22.1 | 23 | 27.5 |
| 246-10, $OD_{600}$ | 17.2 | 21.7 | 17.7 | 20.5 | 18.5 | 24.4 |
| 247-5, $OD_{600}$ | 14 | 14.5 | 13.9 | 14.2 | 14 | 18.2 |
| *C. sonorensis*, arabinose g/L | 19.01 | 18.11 | 16.74 | 12.79 | 9.24 | 0 |
| 246-1, arabinose g/L | 17.77 | 17.17 | 15.72 | 12.90 | 9.68 | 0 |
| 247-2, arabinose g/L | 19.20 | 19.11 | 16.40 | 11.72 | 5.78 | 0.58 |
| 246-10, arabinose g/L | 18.09 | 18.24 | 17.05 | 13.72 | 10.73 | 0.32 |
| 247-5, arabinose g/L | 18.89 | 18.52 | 17.11 | 14.67 | 2.82 | 0 |
| *C. sonorensis*, lactic acid g/L | 0.00 | 0.00 | 0.00 | 0.00 | 0.00 | 0.01 |
| 246-1, lactic acid g/L | 0.44 | 0.52 | 0.78 | 1.54 | 2.50 | 3.54 |
| 247-2, lactic acid g/L | 0.00 | 0.00 | 0.43 | 1.64 | 2.31 | 3.28 |
| 246-10, lactic acid g/L | 0.25 | 0.30 | 0.64 | 1.75 | 3.16 | 4.41 |
| 247-5, lactic acid g/L | 0.28 | 0.32 | 0.76 | 1.51 | 2.37 | 3.40 |
| *C. sonorensis*, lactic acid g/g DW | 0.00 | 0.00 | 0.00 | 0.00 | 0.00 | 0.00 |
| 246-1, lactic acid g/g DW | 0.07 | 0.08 | 0.11 | 0.17 | 0.36 | 0.38 |
| 247-2, lactic acid g/g DW | 0.00 | 0.00 | 0.07 | 0.25 | 0.34 | 0.40 |
| 246-10, lactic acid g/g DW | 0.05 | 0.05 | 0.12 | 0.28 | 0.57 | 0.60 |
| 247-5, lactic acid g/g DW | 0.07 | 0.07 | 0.18 | 0.36 | 0.57 | 0.62 |
| *C. sonorensis*, lactic acid g/used arabinose g | 0.00 | 0.00 | 0.00 | 0.00 | 0.00 | 0.00 |
| 246-1, lactic acid g/used arabinose g | 0.20 | 0.18 | 0.18 | 0.22 | 0.24 | 0.18 |
| 247-2, lactic acid g/used arabinose g | 0.00 | 0.00 | 0.12 | 0.20 | 0.16 | 0.17 |
| 246-10, lactic acid g/used arabinose g | 0.13 | 0.17 | 0.22 | 0.28 | 0.34 | 0.22 |
| 247-5, lactic acid g/used arabinose g | 0.25 | 0.21 | 0.26 | 0.28 | 0.14 | 0.17 |

Example 28

Transformation of *C. methanosorbosa* and Production of Lactic Acid by Strains Harboring *B. megaterium* LDH Integrated in the Genome

*C. methanosorbosa* was transformed with the *C. sonorensis* vector pMI278 described above for lactic acid production. pMI278 was digested with SalI and NotI. Lithium acetate transformation according to a modification of the method of Gietz et al. (1992, *Nucleic Acids Res.* 20: 1425) described above in Example 1. Cells from an overnight culture of *C. methanosorbosa* grown to $OD_{600}$=0.9–1.1 were collected by centrifugation, washed first with an excess of a solution of 10 mM Tris-HCl, 1 mM EDTA (H 7.5), and then with an excess of a solution of 100 mM LiAc/10 mM Tris-HCl, 1 mM EDTA (pH 7.5), and resuspended in 2 mL 100 mM LiAc/10 mM Tris-HCl, 1 mM EDTA (pH 7.5). 50 µL of cells was mixed with 10 µg of transforming DNA and 50 µg of heat-denatured herring sperm DNA. To the cells was added 300 µL of a 40% PEG-4000 solution in 100 mM LiAc/10 mM Tris-HCl, 1 mM EDTA (pH 7.5) and the cells were then incubated at 30° C. for 30 min with slow shaking. DMSO was then added (40 µL) and the cells were incubated in a 42° C. water bath for 15 min. Cells were collected by centrifugation, washed with an excess of a solution of 10 mM Tris-HCl, 1 mM EDTA (pH 7.5), resuspended in YPD and incubated at 30° C. overnight. Cells were spread onto solid YPD medium containing 200 µg/mL G418 and incubated at 30° C. for three to five days. Transformants were streaked onto fresh selection plates twice. The transformants were designated as Cm/278-1 through Cm/278-74.

Transformants were tested for their ability to produce L-lactic acid as follows. 5 mL of YPD in a 10 mL plastic tube was inoculated with a colony grown on G418 plates and incubated with shaking at 250 rpm at 30° C. overnight. The cells were removed by centrifugation and the supernatant was analyzed for L-lactic acid using the L-lactic acid UV method of Boehringer Mannheim. L-lactic acid was produced at 2.3–4.3 g/L. The presence of a single copy of *B. megaterium* LDH gene in the genome was verified by Southern blot analysis of HindIII digested yeast DNA using the *B. megaterium* LDH gene as the probe.

These results showed that *B. megaterium* LDH was able to function in *C. methanosorbosa* and produced lactic acid from glucose. The *B. megaterium* LDH is operatively linked to *C. sonorensis* PGK1 promoter that is able to drive expression of a heterologous gene in *C. methanosorbosa*. Furthermore, the *C. sonorensis* TDH1 promoter that is operatively linked to the G418 resistance gene is also able to function in *C. methanosorbosa*.

Example 29

Production of L-lactic Acid in Rich Glucose Medium without Buffering by *C. methanosorbosa* Harboring the *B. megaterium* LDH Gene Integrated into the Genome One of the *C. methanosorbosa* transformants disclosed above (Cm/278-1) was cultivated in YD-medium (yeast nitrogen base without amino acids supplemented with 5% glucose and 0.5 M MES pH 5.5). Cells were then collected by centrifugation and resuspended in 50 mL of YP supplemented with 5% glucose to an $OD_{600}$ of 16. Yeast cells were cultivated in 250 mL Erlenmeyer flasks with 100 rpm shaking at 30° C. Samples were withdrawn during cultivation, $OD_{600}$ was measured, the cells were harvested by centrifugation, and the culture supernatant was analyzed for L-lactic acid (by the L-lactic acid UV method of Boehringer Mannheim, Roche), glucose (by the glucose/GOD-Perid method of Boehringer Mannheim, Roche), for acetate (by the acetic acid UV method of Boehringer Mannheim, Roche), and ethanol (by the ethanol UV method of Boehringer Mannheim, Roche). These results are shown in Table 40.

After 24 hours of cultivation the transformant produced 8.1 g/L lactic acid (equivalent to 19% yield) from glucose and the pH dropped to 3.5.

These results demonstrated that *C. methanosorbosa* overexpressing a heterologous LDH produced lactic acid from glucose in rich medium at low pH.

TABLE 40

OD$_{600}$, residual glucose, lactic acid, ethanol and acetate production and pH of the culture supernatant of the strain Cm/278-1.

|  | 0 h | 4 h | 8 h | 12 h | 24 h | 48 h | 72 h | 96 h | 120 h | 144 h |
|---|---|---|---|---|---|---|---|---|---|---|
| OD$_{600}$ | 16.0 | 17.9 | 18.5 | 18.7 | 22.3 | 17.3 | 17.3 | 16.8 | 26.4 | 17.0 |
| Glucose | 41.2 | 33.2 | 21.6 | 20.4 | 8.7 | n.d. | 0.6 | 0.0 | 0.0 | 0.0 |
| Lactic acid | 0.2 | 2.9 | 4.5 | 6.7 | 8.1 | 5.8 | 5.6 | 6.9 | 6.4 | 5.6 |
| Ethanol | 0.3 | 2.2 | 5.6 | 7.4 | 10.1 | 12.2 | 11.9 | 11.0 | 9.4 | 8.3 |
| pH | 5.5 | 3.9 | 3.7 | 3.6 | 3.5 | 3.6 | 3.7 | 3.6 | 3.5 | 3.6 |
| Acetate | 0.1 | 0.2 | 0.7 | 0.9 | 2.3 | 3.5 | 4.1 | 4.2 | 3.9 | 3.8 |

Glucose, lactic acid, ethanol, and acetate all in g/L.

Example 30

Production of L-lactic Acid in CaCO$_3$-buffered Defined Glucose Medium by *C. methanosorbosa* Harboring the *B. Megaterium* LDH Gene Integrated into the Genome The transformed *C. methanosorbosa* cells disclosed above (specifically, transformants designated Cm/278-1 and Cm/278-14) and the untransformed host strain (Cm) were cultivated in YD-medium (yeast nitrogen base without amino acids supplemented with 5% glucose and 0.5 M MES, pH 5.5). The cells were then collected by centrifugation and resuspended in 50 mL of YD medium (yeast nitrogen base without amino acids supplemented with 10% glucose) to an OD$_{600}$ of 15 for the cultivation experiments. Yeast cells were cultivated in 250 mL Erlenmeyer flasks containing 4 g CaCO$_3$ with 100 rpm shaking at 30° C. The pH of the culture medium throughout the cultivation was 6.5. Samples were withdrawn during cultivation, cells harvested by centrifugation and the culture supernatant analyzed by HPLC for lactic acid, glucose and ethanol, as described above. These results are shown in Tables 41–44.

The transformants had consumed glucose at 96 hours of cultivation and had produced 63–65 g/L of lactic acid (equivalent to 63–64% yield) and 6.5–6.9 g/L of ethanol. The host strain (Cm) had used all glucose by 120 hours of cultivation and it had produced 23 g/L of ethanol and no lactic acid.

These results demonstrated that *C. methanosorbosa* cells overexpressing a heterologous LDH gene produced lactic acid from glucose in defined medium at neutral pH. High lactic acid titers, 63–65 g/L, and yields 63–64% were achieved.

TABLE 41

Glucose g/L

| Strain | 0 h | 4 h | 8 h | 12 h | 24 h | 48 h | 72 h | 96 h | 120 h |
|---|---|---|---|---|---|---|---|---|---|
| 278-1 | 99.81 | 83.83 | 80.72 | 75.18 | 63.28 | 33.17 | 16.08 | 0.0 | 0.0 |
| 278-14 | 102.07 | 85.14 | 81.51 | 75.01 | 63.01 | 33.28 | 16.36 | 0.0 | 0.0 |
| Cm | 89.18 | 87.29 | 79.69 | 72.78 | 60.28 | 36.40 | 22.56 | 2.11 | 0.0 |

TABLE 42

Lactic acid g/L

| Strain | 0 h | 4 h | 8 h | 12 h | 24 h | 48 h | 72 h | 96 h | 120 h |
|---|---|---|---|---|---|---|---|---|---|
| 278-1 | 0.25 | 1.77 | 4.19 | 6.86 | 13.24 | 33.34 | 53.18 | 63.22 | 59.54 |
| 278-14 | 0.25 | 2.31 | 4.59 | 7.00 | 13.41 | 35.49 | 54.38 | 64.98 | 64.60 |
| Cm | 0.00 | 0.00 | 0.00 | 0.00 | 0.00 | 0.00 | 0.68 | 0.40 | 0.00 |

TABLE 43

Ethanol g/L

| Strain | 0 h | 4 h | 8 h | 12 h | 24 h | 48 h | 72 h | 96 h | 120 h |
|---|---|---|---|---|---|---|---|---|---|
| 278-1 |  | 0.62 | 1.45 | 2.07 | 3.13 | 4.53 | 6.17 | 6.51 | 4.18 |
| 278-14 |  | 1.11 | 1.68 | 2.12 | 2.36 | 4.58 | 6.16 | 6.91 | 5.71 |
| Cm | 0.3 | 1.75 | 3.66 | 5.47 | 9.80 | 14.83 | 21.7 | 27.08 | 23.51 |

TABLE 44

Lactic acid g/used glucose g.

| | 0 h | 4 h | 8 h | 12 h | 24 h | 48 h | 72 h | 96 h | 120 h |
|---|---|---|---|---|---|---|---|---|---|
| 278-1 | 0.21 | 0.10 | 0.21 | 0.27 | 0.35 | 0.49 | 0.63 | 0.63 | 0.59 |
| 278-14 | 0.00 | 0.15 | 0.24 | 0.27 | 0.35 | 0.52 | 0.64 | 0.64 | 0.64 |
| Cm | 0.00 | 0.00 | 0.00 | 0.00 | 0.00 | 0.00 | 0.01 | 0.00 | 0.00 |

Example 31

Enzyme Activities of Lactate Dehydrogenase and Pyruvate Decarboxylase and Production of L-lactic Acid in Defined Glucose Medium by *C. methanosorbosa* Harboring the *B. megaterium* LDH Gene Integrated into the Genome The *C. methanosorbosa* transformants disclosed above (Cm/278-1 and Cm/278-14) were cultivated in 50 mL of YD-medium (yeast nitrogen base without amino acids supplemented with 5% glucose and 0.5 M MES, pH 5.5). Yeast cells were cultivated in 250 mL Erlenmeyer flasks with 250 rpm shaking to an $OD_{600}$ of 10 at 30° C. Samples were collected (2 mL) and cells were harvested by centrifugation. The culture supernatant was analyzed by HPLC.

For enzyme activity measurements the cell pellet was washed with 1 mL of ice-cold 10 mM $K_2HPO_4/KH_2PO_4$, 2 mM EDTA (pH 7.5). Washed pellets were resuspended with 0.5 mL of the same buffer and stored at −70° C. Samples were thawed at room temperature and washed once with 1 mL of sonication buffer (100 mM $KH_2PO_4/K_2HPO_4$, 2 mM $MgCl_2$, 10 mM DTT, pH 7.5). Washed samples were resuspended to 0.5 mL of sonication buffer and homogenized with 0.5 mL of glass beads in a Bead Beater homogenizer for 1 min. After homogenization, the samples were centrifuged at 14,000 rpm for 30 min at 4° C. Supernatant samples were collected and lactate dehydrogenase and pyruvate decarboxylase activities were determined spectrophotometrically ($A_{340}$) as described above in example 18. These results are shown in Table 45.

At 20 h of cultivation, transformants 278-1 and 278-14 produced 0.69 and 0.33 g/L lactic acid (equivalent to 7 and 4% yield from glucose), respectively. At that time point, lactate dehydrogenase activity was 0.05 and 0.16 U/mg total cellular protein, and pyruvate decarboxylase activity was 0.71 and 0.53 U/mg total cellular protein in the transformant 278-1 and 278-14, respectively.

These results demonstrated that lactate dehydrogenase activity is detected in *C. methanosorbosa* cells overexpressing a heterologous LDH gene and confirmed that the cells were capable of producing lactic acid from glucose. The lower activity could be attributed to a lower starting $OD_{600}$ and higher aeration (250 rpm), resulting in predominantly cell growth and small amount of lactate production.

TABLE 45

Intracellular LDH and PDC enzyme activities (U/mg total cellular protein) and residual glucose, lactic acid and ethanol (g/L) in the culture supernatant of *C. methanosorbosa* expressing the *B. megaterium* LDH.

| Strain | | LDH U/mg | PDC U/mg | Glucose g/L | Lactic acid g/L | Ethanol g/L |
|---|---|---|---|---|---|---|
| Cm/278-1 | Cm/BmLDH | 0.05 | 0.71 | 40.8 | 0.69 | 1.31 |
| Cm/278-14 | Cm/BmLDH | 0.16 | 0.53 | 41.9 | 0.33 | 0.92 |

Example 32

Production of Lactic Acid in Defined Xylose Medium by *C. sonorensis* Harboring the *L. helveticus* or the *B. megaterium* LDH Encoding Gene and by *C. methanosorbosa* Harboring the *B. megaterium* LDH Encoding Gene Integrated in the Genome Lactic acid was produced from xylose in $CaCO_3$ buffered cultures of *C. sonorensis* and *C. methanosorbosa* cultivated on defined medium. The cell biomass was generated either on glucose or on xylose in two stages before transfer into the xylose-containing production medium.

A) Biomass Generation on Glucose and Lactate Production on Xylose 5 mL of YP+5% glucose medium was inoculated with a yeast colony (strain C40/288-34) grown on YPD plates. The culture was incubated overnight with 250 rpm shaking at 30° C. 50 mL of YD-medium (yeast nitrogen base, no amino acids supplemented, 5% glucose, and 0.5 M MES, pH 5.5) in 250 mL Erlenmeyer flasks was inoculated into an initial $OD_{600}$ of 0.1 and incubated with 250 rpm shaking overnight at 30° C. until an $OD_{600}$ of 10 was reached. The cells were resuspended in 50 mL of YX-medium (yeast nitrogen base without amino acids supplemented with 5% xylose) to an $OD_{600}$ of 11–13. The cells were cultivated in 250 mL Erlenmeyer flasks containing 2 g $CaCO_3$ with 100 rpm shaking at 30° C. Samples were withdrawn during cultivation. The cells were removed by centrifugation, and the culture supernatant was analyzed for lactic acid and xylose by HPLC as described above (Example 14). Two independent experiments were carried out and the results are shown in Table 46.

The *C. sonorensis* transformant C40/288-34 consumed 50 g/L of xylose in 7–8 days and produced 13–16 g/L of lactic acid, corresponding to 28–32% lactic acid yield from xylose.

TABLE 46

Lactic acid production from xylose in $CaCO_3$ buffered cultivation on defined medium by glucose-grown cells. The yields were calculated at peak lactate concentration (168 or 198 h). The data are from two independent experiments.

| Strain | Genotype | Time h | Residual xylose g/L | L.A. g/L | L.A. yield from xylose g/g |
|---|---|---|---|---|---|
| C40/288-34 | 2xLhLDH pdc1−pdc2− | 168 | 0 | 13 | 0.28 |
| C40/288-34 | 2xLhLDH pdc1−pdc2− | 198 | 2.2 | 16 | 0.32 |

B) Biomass Generation on Xylose and Lactate Production on Xylose

Transformants 265-55 and 265-44 (*C. sonorensis*) harboring the *B. megaterium* LDH, transformants C40/288-34, C40/288-36, 257-3, and 246-27 (*C. sonorensis*) harboring the *L. helveticus* LDH, and transformants Cm/278-1 and Cm/278-42 (*C. methanosorbosa*) harboring the *B. megaterium* LDH were used. 50 mL of YP+5% xylose medium in a 250 mL shake flask were inoculated with a yeast colony grown on YP+2% xylose plates. The culture was incubated overnight with 250 rpm shaking at 30° C. until an $OD_{600}$ of 10 was reached, then 50 mL of YX-medium (yeast nitrogen base, no amino acids supplements, 5% xylose, and 0.5 M MES, pH 5.5) in a 250 mL Erlenmeyer flasks was inoculated to an initial $OD_{600}$ of 0.2. The cells were incubated with 250 rpm shaking overnight at 30° C. until an $OD_{600}$ of 7–10 was reached. The cells were resuspended in 50 mL of YX-medium (yeast nitrogen base, no amino acids supplements, and 5% xylose) to an $OD_{600}$ of 11–12. The cells were cultivated in 250 mL Erlenmeyer flasks containing 2 g $CaCO_3$ with 100 rpm shaking at 30° C. Samples were withdrawn during cultivation. The cells were removed by centrifugation, and the culture supernatant was analyzed for lactic acid and xylose by HPLC as described above (Example 14). The results are shown in Table 47.

*C. sonorensis* LDH transformants consumed 50 g/L of xylose, typically in 5–6 days. Maximal lactic acid titers were measured 4–5 days after transfer into $CaCO_3$-buffered xylose medium, when at least 95% of the xylose was consumed. The amount of lactic acid produced was 30–37 g/L, corresponding to a 63–76% lactic acid yield from xylose.

*C. methanosorbosa* LDH transformants consumed 50 g/L of xylose, typically in 5–6 days. Maximal lactic acid titers were measured 4–5 days after transfer into CaCO$_3$-buffered xylose medium, when at least 95% of the xylose was consumed. Transformants produced 8–14 g/L of lactic acid, corresponding to a 16–28% lactic acid yield from xylose.

TABLE 47

Lactic acid production from xylose in CaCO$_3$-buffered defined medium by cells grown on xylose. The yields were calculated at peak lactic acid concentration.

| Strain | Genotype | Time h | Residual xylose g/L | L.A. g/L | L.A. yield from xylose g/g |
|---|---|---|---|---|---|
| 265-55 | 1xBmLDH PDC+ | 96 | 1.5 | 36 | 0.74 |
| 265-44 | 1xBmLDH PDC+ | 96 | 0.9 | 37 | 0.76 |
| C40/288-34 | 2xLhLDH pdc1-pdc2- | 96 | 3.0 | 33 | 0.71 |
| C40/288-36 | 2xLhLDH pdc1-PDC2+ | 96 | 1.9 | 36 | 0.76 |
| 257-3 | 1xLhLDH pdc1-PDC2+ | 120 | 2.2 | 30 | 0.63 |
| 246-27 | 1xLhLDH PDC+ | 120 | 1.2 | 32 | 0.66 |
| C. sonorensis | PDC+ | 96 | 17.3 | 0 | 0.00 |
| Cm/278-1 | 1xBmLDH PDC+ | 120 | 1.2 | 14 | 0.28 |
| Cm/278-42 | 1xBmLDH PDC+ | 96 | 1.8 | 8 | 0.16 |
| C. methanosorbosa | PDC+ | 96 | 1.6 | 0 | 0.00 |

This Example demonstrated that the culture conditions and the history of the inoculum have a major effect on lactic acid production from xylose. When the biomass was generated on glucose, the C. sonorensis LDH transformant C40/288-34 converted xylose into lactic acid, after transfer into xylose-containing medium, at approximately 30% yield. In comparison, when the biomass was generated on xylose, the same transformant converted xylose into lactic acid with a much higher yield (63–76%), after transfer into xylose-containing medium. The xylose-grown biomass also consumed xylose faster than the glucose-grown biomass under lactic acid production conditions. The data suggests that increased lactic acid yields can be obtained when the cells are "adapted" to sugars other than glucose, for example xylose, by growth on xylose-containing medium, prior to their transfer to the xylose-containing lactic acid production medium.

Example 33

Production of L-lactic Acid in Defined Glucose Medium by C. sonorensis Comprising a Deleted pdc1 Gene and a Disrupted pdc2 Gene and Harboring the L. helveticus LDH Encoding Gene Integrated into the Genome The C. sonorensis transformants designated 257-3, C40/288-2, C40/288-34 and C40/288-11 (described above in Example 13) were cultivated and assayed as described in Example 19, with the exception that the cells were suspended to an OD$_{600}$=18 for the lactate production phase. The culture supernatant was analyzed for lactic acid, glucose, and ethanol as described above. These results are shown in Table 48.

The pdc1-strain 257-3 (where pdc1 is deleted) produced 89 g/L of lactic acid in 48 h, corresponding to a 93% yield from glucose (g/g). The pdc1-(deleted) pdc2-(where pdc2 is disrupted) strains C40/288-2, C40/288-34 and C40/288-11 produced 86–87 g/L of lactic acid in 72 h, corresponding to 89–90% yield from glucose (g/g). No ethanol was detected at these time points.

TABLE 48

Lactic acid titers and yields obtained on CaCO$_3$-buffered defined medium containing glucose, upon consumption of all glucose (initially 96 g/L).

| Strain | Genotype | Time h | L.A. g/L | L.A. yield from glucose g/g |
|---|---|---|---|---|
| 257-3 | 2xLhLDH pdc1- PDC2+ | 48 | 89 | 0.93 |
| C40/288-2 | 2xLhLDH pdc1- pdc2- | 72 | 87 | 0.90 |
| C40/288-34 | 2xLhLDH pdc1- pdc2- | 72 | 86 | 0.90 |
| C40/288-11 | 2xLhLDH pdc1- pdc2- | 72 | 86 | 0.89 |

It is to be understood that while the invention is described in conjunction with the foregoing detailed description and examples, they are intended to illustrate and not limit the scope or the spirit of the invention, which is defined by the appended claims. Other aspects, advantages, and modifications are within the scope of the claims.

We claim:

1. A genetically modified cell from genera *Candida*, comprising a recombinant expression construct comprising a nucleic acid having a nucleotide sequence encoding a lactate dehydrogenase protein, wherein the nucleic acid encodes a lactate dehydrogenase protein from *Bacillus megaterium, Lactobacillus helveticus,* or *Rhizopus oryzae,* and wherein the lactate dehydrogenase protein-encoding nucleic acid is operatively linked to a promoter functional in a yeast cell from a *Candida* species that is a *Candida sonorensis, Candida parapsilosis, Candida naeodendra, Candida methanosorbosa, Candida entomophila, Candida krusei, Candida blankii,* or *Candida diddensiae* cell wherein the cell expresses a metabolic phenotype that is the Crabtree-negative phenotype.

2. The cell of claim 1, wherein the cell further expresses reduced pyruvate decarboxylase (PDC) activity.

3. The cell of claim 2, wherein the reduced PDC activity results from deletion in at least one pyruvate decarboxylase gene.

4. The cell of claim 2, wherein the reduced PDC activity results from genetic disruption of at least one pyruvate decarboxylase gene.

5. A *Candida* cell according to claim 1, comprising a deletion at a first locus that is the pdc1 gene locus, a disruption at a second locus that is the pdc2 gene locus and insertion of two or more copies of a nucleic acid that encodes a lactate dehydrogenase protein in the cellular genome at each of the pdc1 and pdc2 loci.

6. The cell of claim 5, wherein each of the two or more copies of a nucleic acid that encodes a lactate dehydrogenase protein are operably linked to a promoter that is transcriptionally active in the *Candida* cell.

7. A *Candida* cell according to claim 1 that is genetically modified to contain non-functional or deleted pdc1 or pdc2 gene, characterized by at least a 10-fold reduction of ethanol production when cultured in the presence of a defined glucose or rich glucose medium.

8. The *Candida* cell of claim 1, wherein the cell has increased lactic acid dehydrogenase activity relative to an untransformed *Candida* cell.

* * * * *

UNITED STATES PATENT AND TRADEMARK OFFICE
CERTIFICATE OF CORRECTION

| | | |
|---|---|---|
| PATENT NO. | : 7,141,410 B2 | Page 1 of 1 |
| APPLICATION NO. | : 10/154460 | |
| DATED | : November 28, 2006 | |
| INVENTOR(S) | : Vineet Rajgarhia et al. | |

It is certified that error appears in the above-identified patent and that said Letters Patent is hereby corrected as shown below:

Column 1, line 9, after priority claim, please add the pragraph -- This invention was made with U.S. Government support under contract No. DE-FC36-00GO10598 awarded by the Department of Energy. The Government has certain rights in this invention. --

Signed and Sealed this

Twenty-fourth Day of July, 2007

JON W. DUDAS
*Director of the United States Patent and Trademark Office*